(12) United States Patent
Oulmassov et al.

(10) Patent No.: US 6,943,243 B2
(45) Date of Patent: Sep. 13, 2005

(54) CONTROL OF GENE EXPRESSION IN EUKARYOTIC CELLS

(75) Inventors: Tim N. Oulmassov, Chesterfield, MO (US); Kevin E. McBride, Davis, CA (US); Paula C. Miller, St. Louis, MO (US); John C. Anderson, Kihei, HI (US); Lyle D. Crossland, St. Louis, MO (US); Thomas H. Adams, Stonington, CT (US); Barbara A. Qurollo, Somerville, MA (US); Victoria Gavrias, North Stonington, CT (US)

(73) Assignee: Calgene LLC, Davis, CA (US)

( * ) Notice: Subject to any disclaimer, the term of this patent is extended or adjusted under 35 U.S.C. 154(b) by 40 days.

(21) Appl. No.: 10/360,123

(22) Filed: Feb. 6, 2003

(65) Prior Publication Data

US 2003/0224483 A1 Dec. 4, 2003

Related U.S. Application Data

(62) Division of application No. 09/608,958, filed on Jun. 30, 2000, now Pat. No. 6,518,066.
(60) Provisional application No. 60/195,690, filed on Apr. 7, 2000, provisional application No. 60/177,578, filed on Jan. 22, 2000, and provisional application No. 60/148,441, filed on Jul. 1, 1999.

(51) Int. Cl.$^7$ .......................... C07H 21/04; A01H 5/00; C12N 1/19; C12N 5/14
(52) U.S. Cl. .................. 536/23.1; 536/24.1; 435/419; 435/254.2; 800/295
(58) Field of Search ............................ 435/325, 419, 435/254.2; 536/23.1, 24.1; 800/14, 295

(56) References Cited

U.S. PATENT DOCUMENTS

| 5,196,318 A | 3/1993 | Baldwin et al. |
| 5,942,435 A | * 8/1999 | Wheeler ..................... 435/325 |

FOREIGN PATENT DOCUMENTS

| WO | WO 92/18614 | 10/1992 |
| WO | WO 00/09696 | 2/2000 |
| WO | WO 00/09704 | 2/2000 |

OTHER PUBLICATIONS

Doetschman, "Interpretation of Phenotype in Genetically Engineered Mice", Laboratory Animal Science, vol. 49, No. 2, 137–143 (1999).*
Anderson W., "Human gene therapy," Nature, vol. 392 (Supp), p. 25–30 (1998).
Devine J. et al, "Nucleotide sequence of the luxR and luxI genes and structure of the primary regulatory region of the lux regulon of *Vibrio fischeri* ATCC 7744," Biochemistry, p. 837–42, (1988).
Eberhard A. et al., "Analogs of the autoinducer of bioluminescence in *Vibrio fischeri*," Arch. Microbiol., p. 35–40, (1986).
Engebrecht J. and Silverman M., "Nucleotide sequence of the regulatory locus controlling expression of bacterial genes for bioluminescence," Nucleic Acids Research, vol. 15 (No. 24), p. 10455–67, (1987).
Fray R.G. et al, "Plants genetically modified to produce N–acylhomoserine lactones communicate with bacteria," Nature Biotechnology, vol. 17 (Oct.), p. 1017–20, (1999).
Fuqua C. et al., "Census and consensus in bacterial ecosystems: the luxR–luxI family of quorum–sensing transcriptional regulators," Annual Review Microbiology, p. 727–51, (1996).
Hwang I. et al., "A new regulatory element modulates homoserine lactone–mediated autoinduction of Ti plasmid conjugal transfer," J of Bacteriology, vol. 177 (No. 2), p. 449–58, (1995).
Hwang I. et al., "TraI, a luxI homologue, is responsible for production of conjugation factor, the Ti plasmid N–acylhomoserine lactone autoinducer," PNAS, vol. 91 (May), p. 4639–43, (1994).
Kaplan H.B. and Greenberg E.P., "Overproduction and purification of the luxR gene product: transcriptional activator of the *Vibrio fischeri* luminescence system," PNAS, vol. 84 (Oct.), p. 6639–43, (1987).
Palu et al, "In pursuit of new developments for gene therapy of human diseases," J of Bioctechnology, vol. 68 (1), p. 1–13, (1999).
Piper K.R. et al, "Conjugation factor of *Agrobacterium tumefaciens* regulates Ti plasmid transfer by autoinduction," Nature, vol. 362 (Apr.), p. 448–50, (1993).
Robson N.D. et al., "N–acyl–homoserine–lactone–dependent signalling and its potential biotechnological applications," Trends in Biotechnology, vol. 15 (No. 11), p. 458–64, (1997).
Schaefer A.L. et al., "Generation of cell–to–cell signals in quorum sensing: acyl homoserine lactone synthase activity of purified *Vibrio fischeri* LuxI protein," PNAS, vol. 93 (No.18), p. 9505–9509, (1996).
Shadel G.S. and Baldwin T.O., "Positive autoregulation of the *Vibrio fischeri* luxR gene," J of Biological Chemistry, vol. 267 (No. 11), p. 7696–7702, (1992).
Val D.L. and Cronan Jr. J.E., "In vivo evidence that S–adenosylmethionine and fatty acid synthase intermediates are the substrates for the LuxI family of autoinducer synthases," J of Bacteriology, vol. 180 (No. 10), p. 2644–2651, (1998).
Verma et al. "Gene therapy—promises, problems and prospects," Nature, vol. 389, p. 239–242, (1997).

* cited by examiner

Primary Examiner—Terry McKelvey
Assistant Examiner—Nancy T. Vogel
(74) Attorney, Agent, or Firm—M. Todd Rands

(57) ABSTRACT

DNA constructs and other compositions and methods for controlling gene expression in eukaryotic cells and organisms are derived from bacterial quorum sensing systems. One or more cis elements from the luxI promoter ("lux box") or a functionally similar sequence are incorporated in a eukaryotic promoter. A receptor protein from the LuxR family of transcriptional regulators, upon binding an acylated homoserine lactone (AHL) compound, interacts with the lux box, modulating the activity of the promoter.

17 Claims, 29 Drawing Sheets

| NBP | $R^1$ | $R^2$ | $R^3$ | $R^4$ | $R^5$ | $R^6$ | $R^7$ | Relative Stereochemistry |
|---|---|---|---|---|---|---|---|---|
| 6519147 | H | H | H | H | Me | H | n-Bu | cis |
| 6519146 | H | H | H | H | Me | H | n-Bu | trans |
| 6512525 | H | H | H | Me | H | H | n-Bu | --- |
| 6512568 | H | H | H | H | H | Me | n-Bu | cis |
| 6512565 | H | H | H | H | H | Me | n-Bu | trans |
| 6519137 | H | H | H | H | H | Et | n-Bu | cis |
| 6519138 | H | H | H | H | H | Et | n-Bu | trans |
| 6512586 | H | H | H | H | H | n-Bu | n-Bu | cis |
| 6512585 | H | H | H | H | H | n-Bu | n-Bu | trans |
| 6512588 | H | H | H | H | H | Ph | n-Bu | cis |
| 6512589 | H | H | H | H | H | Ph | n-Bu | trans |
| 6512600 | Me | H | H | H | H | H | n-Bu | --- |
| 6512572 | H | Me | H | H | H | H | n-Bu | --- |
| 6512591 | H | Et | H | H | H | H | n-Bu | --- |
| 6630906 | H | Bu | H | H | H | H | n-Bu | --- |
| 6512584 | H | Me | Me | H | H | H | n-Bu | --- |
| 6630903 | H | n-Hexyl | H | H | H | H | Me | --- |

SEQUENCE LISTING

<160> NUMBER OF SEQ ID NOS: 57

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
acctgtagga tcgtacaggt       20

<210> SEQ ID NO 2
<211> LENGTH: 18
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (2)...(2)

```
<223> OTHER INFORMATION: n = A,T,C or G
<220> FEATURE:
<221> NAME/KEY: misc_feature
<222> LOCATION: (11)...(11)
<223> OTHER INFORMATION: n = A,T,C or G

<400> SEQUENCE: 2
rnstgyagat ntrcasrt                                              18

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
acctgtagga tcgtacaggt                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
gaatggatca ttttgcaggt                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 5
acctgccagt tctggcaggt                                            20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
acctgcacta tagtacaggc                                            20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ccctgtaaga gttaccagtt                                            20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
```

```
ccctgtcaat cctgacagtt                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
ccctaccaga tctggcaggt                                              20

<210> SEQ ID NO 10
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 10
acgtgcagat ctgcacat                                                18

<210> SEQ ID NO 11
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 11
aagtgcagat ttgcacat                                                18

<210> SEQ ID NO 12
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 12
atgtgcagat ctgcacat                                                18

<210> SEQ ID NO 13
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 13
gtgtgcagat ctgcacac                                                18

<210> SEQ ID NO 14
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 14
aggtgcagat ctgcacct                                                18

<210> SEQ ID NO 15
<211> LENGTH: 18
<212> TYPE: DNA
```

```
<213> ORGANISM: Artificial Sequence
<220> FEATURE:
<223> OTHER INFORMATION: Synthetic Oligonucleotide

<400> SEQUENCE: 15
atttgcagat ctgcaaat                                                  18

<210> SEQ ID NO 16
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 16
atgagcagat ctgctcat                                                  18

<210> SEQ ID NO 17
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 17
atgtccagat ctggacat                                                  18

<210> SEQ ID NO 18
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 18
atgtgaagat cttcacat                                                  18

<210> SEQ ID NO 19
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 19
atgtgcggat ccgcacat                                                  18

<210> SEQ ID NO 20
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 20
atgtgcaaat ttgcacat                                                  18

<210> SEQ ID NO 21
<211> LENGTH: 18
<212> TYPE: DNA
<213> ORGANISM: Artificial Sequence
<220> FEATURE:
<223> OTHER INFORMATION: Synthetic Oligonucleotide

<400> SEQUENCE: 21
atgtgcagta ctgcacat                                                  18
```

<210> SEQ ID NO 22
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 22
atgtgcagac tgcacat                                              17

<210> SEQ ID NO 23
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 23
aacttaacct gcactatagt acaggtaaca                                30

<210> SEQ ID NO 24
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 24
aacttaacct gtaggatcgt acaggtaaca                                30

<210> SEQ ID NO 25
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 25
aacttaacct gccagttctg gcaggtaaca                                30

<210> SEQ ID NO 26
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 26
aacttaacgt gcagatctgc acataaca                                  28

<210> SEQ ID NO 27
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 27
aacttaacct gtaggatcgt acaggtaaca                                30

<210> SEQ ID NO 28
<211> LENGTH: 30
<212> TYPE: DNA
<213> ORGANISM: Artificial Sequence
<220> FEATURE:

-continued

<223> OTHER INFORMATION: Synthetic Oligonucleotide

<400> SEQUENCE: 28
aacttaacct gtaggatcgt acaggtaaca         30

<210> SEQ ID NO 29
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 29
aacttaacct gtaggatcgt acaggtaaca         30

<210> SEQ ID NO 30
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 30
aacttaacct gcactatagt acaggtaaca         30

<210> SEQ ID NO 31
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 31
aacttaacct gcactatagt acaggtaaca         30

<210> SEQ ID NO 32
<211> LENGTH: 28
<212> TYPE: DNA
<213> ORGANISM: Artificial Sequence
<220> FEATURE:
<223> OTHER INFORMATION: Synthetic Oligonucleotide

<400> SEQUENCE: 32
aacttaacgt gcagatctgc acataaca         28

<210> SEQ ID NO 33
<211> LENGTH: 28
<212> TYPE: DNA
<213> ORGANISM: Artificial Sequence
<220> FEATURE:
<223> OTHER INFORMATION: Synthetic Oligonucleotide
      32

<400> SEQUENCE: 33
aacttaacgt gcagatctgc acataaca         28

<210> SEQ ID NO 34
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 34
aacttaacct gccagttctg gcaggtaaca         30

<210> SEQ ID NO 35
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 35 aacttaaccct gccagttctg gcaggtaaca                                    30

<210> SEQ ID NO 36
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 36
tgaaaaagat aaatgccgac gacacataca gaa                                 33

<210> SEQ ID NO 37
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 37
agctttatcg atgtacttaa tttttaaagt atgg                                34

<210> SEQ ID NO 38
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 38
ggagcccata tgttttcttt tttccttgaa aat                                 33

<210> SEQ ID NO 39
<211> LENGTH: 33
<212> TYPE: DNA
<213> ORGANISM: Artificial Sequence
<220> FEATURE:
<223> OTHER INFORMATION: Synthetic Oligonucleotide

<400> SEQUENCE: 39
acgtacgatc gatccgcccg tcgcagtcac tac                                 33

<210> SEQ ID NO 40
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 40
gtagccatat ggccttggtt gacggttttc                                     30

<210> SEQ ID NO 41
<211> LENGTH: 30
<212> TYPE: DNA
<213> ORGANISM: Artificial Sequence
<220> FEATURE:
<223> OTHER INFORMATION: Synthetic Oligonucleotide

```
<400> SEQUENCE: 41
catcgatctg agaggcaaga tcagagagta                                    30

<210> SEQ ID NO 42
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 42
cttactcata tgaggaatga cggaggcttt                                    30

<210> SEQ ID NO 43
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 43
ctgcgcttca gatgaggccc agcgccgcgg                                    30

<210> SEQ ID NO 44
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 44
catatgcagc actggctgg                                                19

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 45
gtcgacctca gatgagtttc cg                                            22

<210> SEQ ID NO 46
<211> LENGTH: 12
<212> TYPE: PRT
<213> ORGANISM: Unknown
<220> FEATURE:
<223> OTHER INFORMATION: Synthetic peptide
<220> FEATURE:
<223> OTHER INFORMATION: influenza hemaglutinin epitope

<400> SEQUENCE: 46

Met Gly Tyr Pro Tyr Asp Val Pro Asp Tyr Ala His
 1               5                  10

<210> SEQ ID NO 47
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 47
aattgtagaa ataattttgt ttaactttaa gaaggagata tacc                    44
```

<210> SEQ ID NO 48
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 48
catgggtata tctccttctt aaagttaaac aaaattattt ctac                44

<210> SEQ ID NO 49
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 49
acgtaagctt cgaaattaat acgactcact ataggg                36

<210> SEQ ID NO 50
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 50 aaggag                6

<210> SEQ ID NO 51
<211> LENGTH: 6
<212> TYPE: DNA
<213> ORGANISM: Artificial Sequence
<220> FEATURE:
<223> OTHER INFORMATION: Synthetic Oligonucleotide

<400> SEQUENCE: 51 uuccuc                6

<210> SEQ ID NO 52
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 52
actgccatgg ccatttgctg tccaccagtc atgctagcca tatgtatatc tccttcttaa       60
agttaaac                68

<210> SEQ ID NO 53
<211> LENGTH: 76
<212> TYPE: DNA
<213> ORGANISM: Artificial Sequence
<220> FEATURE:
<223> OTHER INFORMATION: Synthetic Oligonucleotide

<400> SEQUENCE: 53
actgccatgg ccatttgctg tccaccagtc atgctagcca tatgtatatg aggaacttaa       60
agttaaacaa aattat                76

<210> SEQ ID NO 54

-continued

```
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 54
actgccatgg ccatttgcaa ggcaggacta atgatagcca tatgtatatc tccttcttaa      60
agttaaac                                                               68

<210> SEQ ID NO 55
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 55
actgccatgg ccatttgcaa ggcaggacta atgatagcca tatgtatatg aggaacttaa      60
agttaaac                                                               68

<210> SEQ ID NO 56
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 56
actgccatgg ccatttgctg tcggcctgac cacctagcca tatgtatatc tccttcttaa      60
agttaaac                                                               68

<210> SEQ ID NO 57
<211> LENGTH: 68
<212> TYPE: DNA
<213> ORGANISM: Artificial Sequence
<220> FEATURE:
<223> OTHER INFORMATION: Synthetic Oligonucleotide

<400> SEQUENCE: 57
actgccatgg ccatttgctg ggcagcggta gtgctagcca tatgtatatc tccttcttaa      60
agttaaac                                                               68
```

US 6,943,243 B2

CONTROL OF GENE EXPRESSION IN EUKARYOTIC CELLS

This application is a divisional of U.S. application Ser. No. 09/608,958, filed Jun. 30, 2000, now U.S. Pat. No. 6,518,066, which claims the benefit of U.S. Provisional Application No. 60/148,441 filed Jul. 1, 1999, U.S. Provisional Application No. 60/177,578 filed Jan. 22, 2000, and U.S. Provisional Application No. 60/195,690 filed Apr. 7, 2000, the entireties of which are incorporated herein by reference.

FIELD OF THE INVENTION

This invention relates to methods and compositions for regulating the expression of genes in eukaryotic cells, particularly through the use of promoters that are chemically inducible or repressible.

BACKGROUND OF THE INVENTION

A wide variety of bacterial species produce acylated homoserine lactone (AHL) derivatives that function in cell-cell communication. This signaling system is used, for example, to monitor population cell density in a process called quorum sensing. Each cell in a population produces a low basal level of the diffusible AHL via the activity of an AHL synthase, usually a member of the LuxI family of proteins. The AHL concentration increases with bacterial population density until the AHL concentration is sufficient to cause expression of various AHL-dependent genes via an AHL receptor protein, usually a member of the LuxR family of transcription regulators. In at least some species, the AHL synthase gene is inducible by AHL, leading to auto-induction of AHL synthesis. Quorum sensing systems have been described in *Vibrio fischeri* (lux bioluminescence genes), *Pseudomonas aeruginosa* (virulence genes), *Agrobacterium tumefaciens* (conjugal transfer), *Serratia liquefaciens* (swarming motility), and *Erwinia caratovora* (antibiotic production), for example. For reviews, see, e.g.: Fuqua and Greenberg, *Curr. Opinion Microbiol.* 1:183–189, 1998; and Fuqua et al., *Ann. Rev. Microbiol.* 50:727–751, 1996).

According to published studies of the LuxR-LuxI quorum sensing system of *Vibrio fischeri*, specific binding to the LuxR binding site (or "lux box") within the lux promoter sequences was not observed with either LuxR alone or bacterial RNA polymerase alone, but required the presence of both LuxR and RNA polymerase. Thus, it has been thought that inducible gene expression under the control of LuxR is possible only when bacterial RNA polymerase is also present, i.e., in bacterial cells, limiting the utility of quorum sensing systems in eukaryotic cells.

A number of systems have been described for regulating eukaryotic gene, including various promoter elements that are chemically inducible. However, there remains a need for an inducible promoter system that can be used in a variety of eukaryotic organisms, that is strictly regulated and strongly induced, and that responds to a chemical inducer that has low cytotoxicity.

SUMMARY OF THE INVENTION

We have discovered that bacterial quorum sensing systems can be used in controlling eukaryotic gene expression, whether in the nucleus or in organelles, such as chloroplasts, of a eukaryotic cell.

According to one aspect of the invention, non-naturally occurring polynucleotides are provided that incorporate elements of a bacterial quorum sensing system and that are useful for controlling or modulating gene expression in a eukaryotic cell. According to one embodiment, a polynucleotide is provided that comprises a promoter that is functional in a eukaryotic cell comprising a cis element (e.g., a lux box or similar sequence) that mediates responsiveness of the promoter to an N-acylhomoserine lactone (AHL). Such cis elements are referred to herein as AHL-response elements. Upon binding an AHL or an AHL analog, the AHL receptor binds to the AHL-response element, modulating transcription of the operably linked gene of interest. Any known AHL-response element, AHL synthase gene, or AHL receptor gene may be used in the practice of the invention. The AHL receptor gene encodes a native AHL receptor, portions of a native AHL receptor that bind to a corresponding AHL-response element), or a fusion protein that comprises a native AHL receptor (or a portion thereof that binds to a corresponding AHL-response element) fused in-frame to a eukaryotic activation or repression domain.

Another embodiment of the invention is a polynucleotide that comprises a promoter that is functional in a eukaryotic cell (the promoter optionally comprising an AHL-response element) that is operably linked to a sequence that encodes an AHL synthase or an AHL receptor.

According to one aspect of the invention, a polynucleotide is provided that comprises: a first sequence comprising a first promoter that is functional in a eukaryotic cell comprising an AHL-response element, and a second sequence comprising a second promoter that is functional in the eukaryotic cell operably linked to a sequence encoding an AHL receptor. When expressed in the cell, the AHL receptor binds to the AHL-response element and modulates transcription of the first promoter. Another embodiment of the invention is a polynucleotide comprising: a first sequence comprising a promoter that is functional in a eukaryotic cell comprising an AHL-response element; a second sequence comprising a promoter that is functional in the cell comprising an AHL-response element operably linked to a sequence encoding an AHL synthase that, when expressed in the eukaryotic cell, synthesizes an AHL; and a third sequence comprising a third promoter that is functional in the cell operably linked to a sequence encoding an AHL receptor. Binding of the AHL by the AHL receptor causes the AHL receptor to bind to the AHL-response element and modulate transcription of the first promoter. In a eukaryotic cell that provides other enzymes required for AHL biosynthesis, treatment of the cell with exogenous AHL initiates auto-induced synthesis of the AHL and consequently continued expression of the gene of interest.

According to another embodiment of the invention, eukaryotic cells are provided that comprise: a first sequence comprising a promoter that is functional in the eukaryotic cell comprising an AHL-response element operably linked to a gene of interest; and a second sequence comprising a promoter that is functional in the eukaryotic cells operably linked to a sequence encoding an AHL receptor. One or both of the promoters may be non-constitutive, such as a cell-, tissue-, or organ-, or developmental stage-specific promoter, or an inducible promoter, for example.

Another aspect of the invention relates to organellar (including plastid or mitochondrial) expression. According to one embodiment, a eukaryotic cell is provided that comprises: an organelle comprising a first sequence comprising a promoter that is functional in the organelle, the promoter comprising an AHL-response element operably linked to a gene of interest; and a nucleus, the nucleus comprising a second sequence comprising a second promoter that is functional in the nucleus, the second promoter operably linked to a sequence that encodes a polypeptide comprising (i) an organelle-transport (or targetting or transit) peptide and (ii) an AHL receptor. The AHL receptor produced by expression of the second sequence and uptake of the polypeptide by the organelle binds to the AHL-response element and modulates transcription of the first promoter upon binding of an AHL. According to an alternative embodiment, the AHL receptor is expressed in the organelle rather than being taken up by the organelle. In this embodiment, the cell comprises an organelle, which in turn comprises a first sequence comprising a promoter that is functional in the organelle comprising an AHL-response element operably linked to a gene of interest; and a second sequence comprising a promoter that is functional in the organelle operably linked to a sequence that encodes a polypeptide comprising an AHL receptor which binds to the AHL-response element and modulates transcription of the first promoter upon binding of an AHL.

According to another aspect of the invention, compositions are provided that comprise (a) an amount of an AHL or AHL analog that is effective, when applied to a cell comprising an AHL receptor and a promoter comprising an AHL-response element, to cause the AHL receptor to bind the AHL-response element and modulate transcription of the promoter, and (b) a carrier that is substantially non-toxic to the cell. In the case of compositions for application to plant cells, the carrier is a well known agronomically acceptable carrier that is substantially non-phytotoxic. Such compositions may also include one or more agronomically acceptable active or inert ingredients or additives, such as surfactants, sticking agents, etc. Any known AHL or AHL analog may be used in the practice of the invention.

According to another aspect of the invention, methods are provided for modulating the expression of a polynucleotide that comprises a first promoter that is functional in a eukaryotic cell comprising an AHL-response element, such methods comprising expressing in the eukaryotic cell an AHL receptor, and applying to the cell a composition comprising an AHL that is bound by the AHL receptor, causing the AHL receptor to modulate transcription of the first promoter.

According to another aspect of the invention, methods are provided for identifying AHLs that are bound by an AHL receptor. Such methods employ eukaryotic cells comprising a first sequence comprising (i) a first promoter that is functional in the eukaryotic cell comprising an AHL-response element operably linked to a sequence encoding a selectable or screenable marker, and (ii) a second sequence comprising a second promoter that is functional in the eukaryotic cell operably linked to a sequence encoding an AHL receptor, wherein binding of an AHL by the AHL receptor causes expression of the marker. The method involves applying to the cell a composition comprising the AHL and detecting the expression of the marker. Such cells (or organisms such as yeast or plants that comprise such cells) can be used to screen for AHL analogs that are useful for controlling gene expression. For example, a plant comprising such a construct can be used to assay for agronomically useful AHL analogs that are applied to the plant, e.g., by foliar application or by application to the soil or seed.

DETAILED DESCRIPTION OF THE INVENTION

Figure 1:
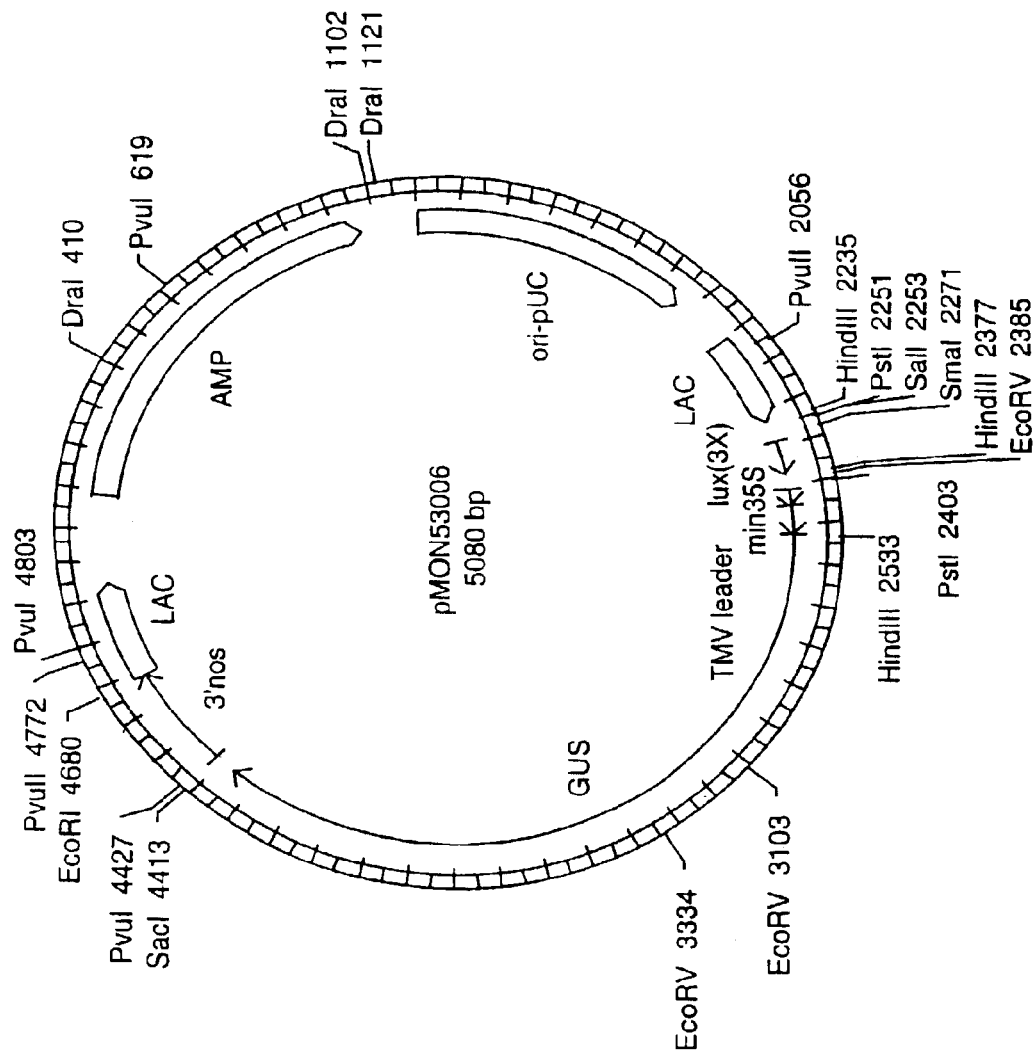
FIG. 1 provides a schematic representation of the expression construct pMON53006.

Quorum sensing systems can be used to control gene expression in any eukaryotic cell, including, but not limited to, yeast, fungi, plant, insect, amphibian, avian, and mammalian cells. Exemplary compositions and methods are described herein for expression of genes located in nuclear and organellar genomes.

According to an embodiment of the present invention, a gene of interest comprising a protein coding sequence is operably linked to a promoter that comprises an AHL-responsive element. Upon binding an AHL compound or an AHL analog, an AHL receptor binds to (or in some embodiments, dissociates from) the AHL-response element, modulating (activating, repressing, or otherwise altering) transcription of the gene of interest. This system may be better understood with reference to the quorum sensing of *Vibrio fischeri*, the best characterized example of the many prokaryotic quorum sensing systems, any of which may be used in the practice of the present invention.

*V. fischeri*, a marine bacteria, produces a diffusible autoinducer, N-3-(oxohexanoyl) homoserine lactone (referred to by the trivial name VAI-1), an AHL that accumulates in the surrounding environment during growth and that readily diffuses across the bacterial cell membrane. VAI-1 is synthesized by LuxI. LuxR is both a receptor for VAI-1 and a VAI-1-dependent transcriptional regulator that binds DNA immediately upstream of the lax promoter.

Examples of bacterial species that have quorum sensing systems with luxI-like genes ("AHL synthase") and/or luxR-like genes ("AHL receptor") are shown in Table 1 (Fugua et al., *Annu. Rev. Microbiol.* 50:727–751, 1996). Any quorum sensing system can be used in the practice of the present invention.

TABLE 1

AHL-Based Regulatory Systems

| Organism | AHL Synthase | AHL Receptor | Signal Molecule | GenBank Accession Numbers |
|---|---|---|---|---|
| *Aeromonas hydrophilia* | AhyI | AhyR | N-(butyryl)-L-homoserine lactone (BHL), N-(hexanoyl)-L-homoserine lactone (HHL) | X89469 |
| *Aeromonas salmonicida* | AsaI | AsaR | BHL, HHL | U65741 |
| *Agrobacterium tumefaciens* | TraI | TraR, TraM | N-(oxo-octanoyl)-L-homoserine lactone (OOHL) | L17024, L22207 |
| *Chromobacterium violaceum* | CviI | CviR | HHL | |
| *Enterobacter agglomerans* | EagI | EagR | N-3-(oxo-hexanoyl)-homoserine lactone (OHHL) | X74300 |
| *Erwinia carotovora* subsp. *carotovora* | CarI (ExpI) | CarR | OHHL | U17224, X72891, X74299, X80475 |
| *Erwinia chrysanthemi* | ExpI EchI | ExpR EchR | ? | X96440 U45854 |
| *Erwinia sterwartii* | EsaI | EsaR | OHHL | L32183, L32184 |
| *Escherichia coli* | ? | SdiA | ? | X03691 |
| *Nitrosomonas europaea* | ? | ? | OHHL | |
| *Obesumbacterium proteus* | OprI | OprR | OHHL | |
| *Pseudomonas aeruginosa* | LasI | LasR | N-(oxodo-decanyoyl)-L-homoserine lactone (OdDHL) | M59425, SwissProt P33883 |
| | VsmI (Rh1I) | VsmR (Rh1R) | BHL | L08962, U11811, U15644 |
| *Pseudomonas aureofaciens* | PhzI | PhzR | ? | L32729, L33724 |
| *Pseudomonas fluorescens* | PhzI | PhzR | HHL | L48616 |
| *Pseudomonas syringae* pv *tabaci* | PsyI | PsyR | ? | U39802 |
| *Ralstonia solanacearum* | SolI | SolR | ? | AF021840 |
| *Rhizobium leguminosarum* | ? | RhiR | N-(3R-hydroxy-7-cis-tetradecanoyl)-L-homoserine lactone, small bacteriocin | M98835 |
| *Rhodobacter sphaeroides* | CerI | CerR | ? | AF016298 |
| *Serratia liquifaciens* | SwrI | ? | BHL | U22823 |
| *Vibrio anguillarum* | VanI | VanR | N-(oxode-canoyl)-L-homoserine lactone (ODHL) | U69677 |

TABLE 1-continued

AHL-Based Regulatory Systems

| Organism | AHL Synthase | AHL Receptor | Signal Molecule | GenBank Accession Numbers |
|---|---|---|---|---|
| Vibrio fischeri | LuxI | LuxR | OHHL, HHL | M19039, M96844, M25752 |
|  | AinS | AinR | N-(octanoyl)-L-homoserine lactone (OHL) | L37404 |
| Vibrio harveyi | LuxLM | LuxN | N-(hydroxy-butyryl)-L-homoserine lactone (HBHL) | L13940 |
| Xenorhabdus nematophilus | ? | ? | HBHL or a close homolog | |
| Yersinia enterocolitica | YenI | YenR | OHHL, HHL | X76082 |
| Yersinia pseudotuberculosis | YepI | YepR | OHHL, HHL | |
| Yersinia ruckeri | YukI | YukR | ? | |

A number of bacteria with proteins homologous to LuxR and LuxI also produce AHL autoinducers similar or identical to VAI-1 of *V. fischeri* (Table 1). All of these signal compounds have identical homoserine lactone moieties but can differ in the length and structure of their acyl groups. LuxI and corresponding enzymes from other species catalyze the ligation of S-adenosylmethionine (SAM) and a fatty acyl chain derived from acyl-acyl carrier protein (ACP) conjugates. The substrates for AHL biosynthesis by LuxR are available in both prokaryotic and eukaryotic cells; the expression of LuxI in a eukaryotic cell is sufficient to produce VAI-1.

Analogs to natural AHL autoinducers ("AHL analogs") can also be used in the practice of the present invention. Several studies of AHL analogs have found a number of AHL analogs that have significant activity in quorum sensing systems, including: analogs of N-(3-oxohexanoyl)-L-homoserine lactone tested in LuxR (Eberhard et al., *Arch. Microbiol.* 146:35–40, 1986; Greenberg et al., J. Bacteriol. 178:2897–2901, 1996) and EsaR (Bycroft et al., *J. Antibiot.* 46:441–454, 1993) systems; analogs of N-(oxooctanoyl)-L-homoserine lactone tested in the TraR system (Winans et al., *J. Bacteriol.* 180:5398–5405, 1998); and analogs of N-(oxododecanyoyl)-L-homoserine lactone (PAI), tested in the LasB system (Iglewski et al., *J. Bacteriol.* 178:5995–6000, 1996). In general, lengthening or shortening the acyl side group by one or two carbons is the best tolerated change, with longer chains better tolerated than shorter chains. Maintaining the 3-oxo substituent is generally required for good activity, and the 1-oxo substituent enhances activity. The 1-oxo substituent is sufficient for binding but not for induction. Reducing the saturation of the acyl chain can be tolerated to some extent.

LuxR-type proteins are composed of two modules, an amino-terminal domain (residues 20–156 of LuxR) with an AHL-binding region (residues 79–120 of LuxR) and a carboxy-terminal transcription regulation domain (residues 160–250 of LuxR), which includes a helix-turn-helix DNA-binding motif (residues 190–210 of LuxR). The carboxy-terminal one-third of these proteins is homologous to DNA binding domains of the LuxR superfamily of transcriptional regulators. A general mechanism of activation for this superfamily of proteins has been proposed by which an amino-terminal domain acts negatively to prevent an interaction between the carboxy-terminal domain and target DNA binding sites. This inhibition can be relieved by the action of a ligand that is an autoinducer in the case of LuxR-type proteins or a phosphoryl group in the case of two-component regulators. Deletions of as many as 40 amino acids from the carboxyl terminus of LuxR result in proteins that remain competent for binding lux regulatory DNA but fail to activate expression of the lax operon. Therefore the region between amino acids 211 and 250 of LuxR is required for transcriptional activation subsequent to DNA binding.

LuxR binds as a homomultimer to the LuxR binding site, which has a dyad symmetry, and a region required for multimerization resides within amino acids 116 and 161 of the amino-terminal portion of the protein.

The LuxR binding site, or lux box (5'-ACCTGTAGGATCGTACAGGT-3') (SEQ ID NO:1), is a 20-nucleotide inverted repeat centered 44 nucleotides upstream of the transcription start site of the luminescence operon (Devine et al., *Proc. Natl. Acad. Sci. USA* 86:5688–5692, 1989; Gray et al., *J. Bacteriol.* 176:3076–3080, 1994). Similarly, 18-bp tra boxes are found upstream of at least three TraR-regulated promoters and are required for transcriptional activation by TraR (Fuqua and Winans, *J. Bacteriol.* 178:435–440, 1996). Similar sequences found in LasR-regulated promoters invariably overlap putative –35 elements of $\sigma^{70}$-type promoters by one nucleotide. The lux and las boxes are sufficiently similar that LuxR can activate transcription from the lasB promoter in the presence of VAI-1, and conversely, LasR can activate transcription of the luminescence operon in the presence of PAI-1 (Gray et al., *J. Bacteriol.* 176:3076–3080, 1994). A number of lux box-like sequences (also referred to herein as "AHL response elements") have been compared (Table 2). The consensus lux box-like sequence is 5'-RNSTGYAXGATNXTRCASRT-3' (SEQ ID NO:2). Synthetic AHL response elements may be produced by varying one or more nucleotides of a native lux box-like sequence. As discussed in the Examples below, when TraR is expressed in carrot cells, a promoter that includes the traA box shows a higher than expected level of basal activity. This basal activity can be significantly reduced without eliminating AHL responsiveness by replacing the traA box with a variant box in which a small number of base pairs of the traA box are altered. Synthetic AHL-responsive promoters may be produced by replacing an AHL response element from one promoter with an AHL-response element from another promoter, or by adding a native or synthetic AHL-response element to a promoter that lacks a functional AHL response element, such as a minimal promoter. In addition, two or more AHL response elements may be present in a single promoter to render the promoter responsive to more than one AHL. A promoter that comprises one or more AHL-response elements is referred to herein as an "AHL-responsive promoter."

TABLE 2

Native and Variant lux Box-Like Sequences

| Gene | lux Box-Like Sequence | |
|---|---|---|
| luxI | ACCTGTAGGATCGTACAGGT | (SEQ ID NO:3) |
| luxD | GAATGGATCATTTTGCAGGT | (SEQ ID NO:4) |

TABLE 2-continued

Native and Variant lux Box-Like Sequences

| Gene | lux Box-Like Sequence | |
|---|---|---|
| lasB | ACCTGCCAGTTCTGGCAGGT | (SEQ ID NO:5) |
| esaR | ACCTGCACTATAGTACAGGC | (SEQ ID NO:6) |
| cepI | CCCTGTAAGAGTTACCAGTT | (SEQ ID NO:7) |
| solI | CCCTGTCAATCCTGACAGTT | (SEQ ID NO:8) |
| rhlI | CCCTACCAGATCTGGCAGGT | (SEQ ID NO:9) |
| traI1 | ACGTGCA-GATC-TGCACAT | (SEQ ID NO:10) |
| traI2 | AAGTGCA-GATT-TGCACAT | (SEQ ID NO:11) |
| traA | ATGTGCA-GATC-TGCACAT | (SEQ ID NO:12) |
| traA1 | gTGTGCA-GATC-TGCACAc | (SEQ ID NO:13) |
| traA2 | AgGTGCA-GATC-TGCACcT | (SEQ ID NO:14) |
| traA3 | ATtTGCA-GATC-TGCAaAT | (SEQ ID NO:15) |
| traA4 | ATGaGCA-GATC-TGCtCAT | (SEQ ID NO:16) |
| traA5 | ATGTcCA-GATC-TGgACAT | (SEQ ID NO:17) |
| traA6 | ATGTGaA-GATC-TtCACAT | (SEQ ID NO:18) |
| traA7 | ATGTGCg-GATC-cGCACAT | (SEQ ID NO:19) |
| traA8 | ATGTGCA-aATt-TGCACAT | (SEQ ID NO:20) |
| traA9 | ATGTGCA-GtaC-TGCACAT | (SEQ ID NO:21) |
| traA-1 | ATGTGCA-GA-C-TGCACAT | (SEQ ID NO:22) |

Other promoters regulated by TraR and LasR lack these sites. For example, the lasI gene does not have a recognizable las box upstream of its promoter (Passador et al., *Science* 260:1127–1130, 1993) and yet is strongly inducible by LasR. Similarly, the traM gene of *A. tumefaciens* appears to have two half-sites upstream of its promoter rather than an orthodox tra box (Fuqua et al., *J. Bacteriol.* 177:1367–1373, 1995; Hwang et al., *J. Bacteriol.* 177:449–458, 1995) and is mildly inducible by TraR. The TraR protein also activates expression of the traR gene at a promoter that has no apparent similarity to any tra box motif. In the case of TraR promoters that have a strong similarity to the consensus tra box motifs are activated to high level expression by 3-oxooctanoyl-homoserine lactone (AAI), and more degenerate motifs are associated with lower levels of induction.

Quorum-sensing promoters may be altered to make them responsive to a different AHL autoinducer by "operator swapping," that is, by replacing lux box-like sequence(s) from the promoter with a lux box-like sequence from a different promoter. For example, a lux box sequence in one promoter may be replaced by a tra or las box sequence. AHL responsiveness can also be modified by "domain swapping," that is, by replacing an AHL-binding region of one LuxR-like protein with the AHL-binding region of another LuxR-like protein such that the DNA-binding specificity of the resulting chimeric protein is unchanged. For example, replacement of the VAI-1-binding region of LuxR with the AAI-1-binding region of TraR would cause the resulting chimeric protein to bind the lux box sequence and modulate transcriptional activity in response to binding of the autoinducer VAI-1. In addition, the activation domain of a LuxR-like protein can be replaced by another activation domain that is a well known activator of gene expression in a given host cell, such as GAL4, VP16, or other well known activator domains.

New members of the LuxR-LuxI family have been sought by screening bacteria for the release of autoinducers using an *Escherichia coli* strain containing a cloned lux regulon but lacking luxI (and therefore not synthesizing VAI-1). Similar experiments have been performed with *Agrobacterium tumefaciens* TraR regulator to screen plant pathogenic soil bacteria. These studies have demonstrated that LuxR and TraR are activated by a subset of known autoinducers. It has also been demonstrated that LuxR-like proteins such as LuxR and *Pseudomonas aeruginosa* LasR activate lux gene expression after binding derivatives of the cognate autoinducers with alterations in acyl chain length or in the carbonyl groups, for example (Eberhard et al., *Arch. Microbiol.* 146:35–40, 1986; Kuo et al., *J. Bacteriol.* 176:7558–7565, 1994; Kuo et al., *J. Bacteriol.* 178:971–976, 1996; Pearson et al., *Proc. Natl. Acad. Sci. USA* 91:197–201, 1994; Fuqua and Winans, *J. Bacteriol.* 176:2796–2806, 1994).

EsaR, ExpR, and YenR are reported to be repressors of their target genes rather than activators, and their respective autoinducers increase expression of the repressed genes.

Quorum-sensing systems would find many uses in modulating gene expression in eukaryotes. Quorum-sensing systems can be used for transcriptional activation or repression. This can be understood best by analogy to the use of the "Tet system" for modulating eukaryotic gene transcription based on specific binding of tetracycline receptor (TetR) to operator sites. Both "Tet-off" and "Tet-on" systems have been developed (Gossen and Bujard, *Proc. Natl. Acad. Sci. USA*, 89:5547–51, 1992). Originally, tight repression of the polymerase II (pol II) promoter was achieved by placing several TetR operator sites adjacent the TATA box, the binding site for a ubiquitous general transcription factor, TBP (TATA-box Binding Protein). In the absence of inducer (tetracycline or a tetracycline analogue), TetR binds to the operator sites, stearically hindering TATA-box recognition by TBP. This prevents binding of the TFIID complex (of which TBP is a central part) to the promoter and assembly of transcription initiation complex on the promoter, thus repressing initiation of transcription. After application of tetracycline, TetR dissociates from the promoter, relieving the transcriptional repression. This approach has been also shown to work in plants (Gatz, et al., *Plant J.*, 2:397–404, 1992; Gatz and Quail, *Proc. Natl. Acad. Sci. USA*, 85:1394–7, 1988) and has also been applied to regulate polIII promoters (Ulmasov et al., *Plant Mol. Biol.*, 35:417–424, 1997).

A strategy to increase the dynamic range of gene regulation via the Tet system has been described (Rossi et al., *Nat. Genet.*, 20:389–393, 1998). This strategy takes advantage the existence of (1) reverse mutants of TetR (rTetR) that bind to DNA only in the presence of the ligand (a phenotype opposite to wild type TetR), and (2) isoforms of TetR that can form homodimers (Tet repressor has a dimerization domain and is active only as a dimer), but cannot form heterodimers. By fusing class B reverse phenotype protein (rTetR$_B$) to the VP16 activation domain (to form rtTA$_B$), and class G wild type repressor (TetR$_G$) to a potent repression domain (called KRAB of human KoxI gene) creating tTR$_G$, two types of eukaryotic transcription factors were created that respond to the same chemical ligand but exert opposite effects on transcription. In the absence of the ligand, only tTR$_G$ binds upstream of the regulated minimal promoter containing tetO sites and actively represses the already low levels of basal transcription from this promoter. In the presence of ligand, (doxycycline, a tetracycline analog), tTR$_G$ dissociates from DNA, but rtTA$_B$ acquires the ability to bind DNA and activates transcription. At the same time, because class B and class G TetR proteins do not heterodimerize, no non-productive heterodimers containing both activation and repression domains can be formed. The advantage of this system over a standard Tet-On system is a lower background expression from the promoter in the absence of the inducer. A similar strategy can be employed with the quorum sensing system described herein.

A simple quorum sensing system would consist of two genes: (1) a gene of interest under the control of an AHL-responsive promoter, that is, a promoter that includes an AHL-response element (such as a lux box), and (2) a gene encoding a DNA-binding polypeptide that binds specifically to the AHL-response element, both genes having promoters that are functional in a eukaryotic cell. The DNA-binding polypeptide preferably includes AHL-binding motif (to control binding of the AHL-response element by application of an AHL) and a helix-turn-helix DNA-binding domain derived from a native AHL receptor. The DNA-binding polypeptide preferably also includes a multimerization region derived from a native AHL receptor. The DNA-binding polypeptide also includes a transcriptional activation region of a native AHL receptor (which is non-functional in eukaryotes but can be functional in chloroplasts) or a heterologous eukaryotic transcriptional activation or repression domain that is well-known in the art, except when the DNA-binding polypeptide is used for passive transcriptional repression by steric hindrance, in which case a transcriptional activation or repression domain is optional. Application of an AHL and binding of the AHL by the AHL-binding motif of the DNA-binding polypeptide causes the DNA-binding polypeptide to bind specifically to the AHL-response element. The transcriptional activation (or repression) domain of the DNA-binding polypeptide then modulates transcription of the AHL-responsive promoter until levels of the AHL in the cell fell below levels required to affect gene expression.

In the case of "passive" transcriptional repression, binding of AHL by the DNA-binding polypeptide causes it to bind to one or more AHL-response element(s) situated close to the TATA box and stearically interfere with transcriptional initiation by polII. DNA-binding fragments of the AHL receptor, or recombinant fusion polypeptides that include such a DNA binding domain and heterologous polypeptide sequences, can be used in place of the full-length AHL receptor polypeptide for such a "passive" repression system.

The quorum-sensing system can also be used for "active" repression of transcription. For example, EsaR functions as a repressor (dissociating from DNA in the presence of its ligand, 3-oxohexanoyl-homoserine lactone, C6-AHL); LuxR and some other members of its family (e.g., TraR) acquire the ability to bind DNA only in the presence of the ligand. Thus, a two-factor system regulated by C6-AHL can be produced that is analogous to the Tet system using "active" repression described above. EsaR is fused to a repression domain and LuxR to an activation domain; both respond to the same AHL but cannot heterodimerize. The only difference between the described Tet two-factor system and a two-factor system based on LuxR/EsaR is that, unlike different isoforms of TetR, EsaR and LuxR recognize slightly different cis-elements. This problem is overcome by placing both LuxR and EsaR binding sites upstream of regulated minimal promoter or by changing the DNA-binding specificity of one of these proteins via mutagenesis or by swapping DNA-binding domains.

Quorum-sensing systems can also be employed to provide a transcriptional "switch" that remains "on" indefinitely once activated by application of exogenous AHL. Examples of such switches include the following three-gene system: (1) a gene of interest under the control of an AHL-responsive promoter (e.g., a promoter that includes a lux box such as the luxI promoter); (2) an AHL synthase gene (e.g., the luxI gene) under the control of a promoter that is responsive to the same AHL; and (3) an AHL receptor gene (e.g., the luxR gene) under the control of a constitutive or tissue-specific promoter, for example. A single application of AHL to a cell transformed with the three genes (which could be included on a single DNA construct) would induce the AHL synthase to synthesize AHL, which would, in turn, induce continued expression of the gene of interest. Substrates for the production of AHL in plant cells, including S-adenosylmethionine, and either acyl-acyl carrier protein (acyl-ACP) or coenzyme A derivative, are available in plant cell plastids. Production of AHL signal molecules in plant cell plastids has been demonstrated by targeting the yenI AHL synthase gene product from *Yersinia entercolitica* to the chloroplasts of transgenic tobacco plants (Fray, et al. (1999), *Nature Biotech,* 17:1017–1020).

Cells, tissues, or organisms containing constructs in which a quorum sensing system is used to control the expression of a well-known operably-linked reporter gene, including a screenable marker such as green fluorescent protein (GFP), luciferase (luc), β-galactosidase, or β-glucuronidase, or a selectable marker such as an antibiotic resistance gene, are useful for screening for AHL analogs that are effective in modulating the expression of the linked reporter gene. Such AHL analogs could be further screened by well known methods to obtain AHL analogs that are non-toxic, display good uptake by the host cell, and have other desirable characteristics, such as agronomically useful AHL analogs, for example.

Resistance to infection by a bacterial pathogen can be achieved by expressing in a plant an AHL synthase gene that produces an AHL that affects the the pathogen's quorum sensing system. A number of species of bacteria that employ quorum sensing systems cause plant disease, for example *Pseudomonas stewartii* (stewarts wilt and leaf blight), *Erwinia carotovora* (soft rot), *Agrobacterium tumefaciens* (crown gall), and *Ralstonia solanacearum* (vascular wilt). Expression in a plant of an AHL synthase that produces an AHL used as an inducer by a bacterial pathogen would cause activation of regulated genes that would otherwise be activated only when the population density of the bacteria is high. The activated genes are ineffective and the bacteria consume energy in an non-productive process that ultimately limits its growth. As one example, N-octanoyl-L-homoserine lactone, a C8-AHL is produced by SolI of *Ralstonia solanacearum* and is a good agonist for the TraR receptor, but also for the LuxR receptor, which normally responds to a C6-substituted AHL. Other species that normally respond to the C6-AHL, such as *E. carotovora* (ExpR) and *P. stewartii* (EsaR), for example, may also be antagonized by the C8 AHL. Thus, transgenic expression of the SolI gene in a plant would confer resistance to several bacterial pathogens.

Expression of an AHL synthase gene in a plant can also be used to cause beneficial bacteria to produce antibiotics that inhibit pathogenic bacteria. For example, *Pseudomonas aureofaciens* strain 30–84, which was isolated from the roots of wheat that were resistant to take-all disease, produces a group of phenazine antibiotics. Antibiotic production by this strain is regulated by a C6-AHL. Production of the C6-AHL in plant cells by expression of the appropriate AHL synthase induces production of antibiotic production in *P. aureofaciens* and inhibits the growth of pathogenic fungi in the vicinity of the plant. (Plant-associated bacteria that employ quorum-sensing systems are reviewed in *Annu. Rev. Phytopathol.* 36:207–225, 1998.)

Definitions and Methods

The following definitions and methods are provided to better define the present invention and to guide those of ordinary skill in the art in the practice of the present invention. Unless otherwise noted, terms are to be understood according to conventional usage by those of ordinary skill in the relevant art. Definitions of common terms in molecular biology may also be found in Rieger et al., *Glossary of Genetics: Classical and Molecular*, 5th edition, Springer-Verlag: New York, 1991; and Lewin, *Genes V*, Oxford University Press: New York, 1994. The nomenclature for DNA bases as set forth at 37 CFR § 1.822 is used. The standard one- and three-letter nomenclature for amino acid residues is used.

A. Nucleic Acid Constructs

"Nucleic acid (sequence)" or "polynucleotide (sequence)" refers to single- or double-stranded DNA or RNA, i.e., a polymer of deoxyribonucleotide or ribonucleotide bases, respectively, the sequence of which is provided herein from the 5' (upstream) end to the 3' (downstream) end. Both sense and anti-sense sequences are included.

"Promoter" refers to a nucleic acid sequence located upstream or 5' to a translational start codon of an open reading frame (or protein-coding region) of a gene and that is involved in recognition and binding of RNA polymerase II and other proteins (trans-acting transcription factors) to initiate transcription. A "mammalian promoter" is a native or non-native promoter that is functional in mammalian cells, a "plant promoter" is functional in plant cells, and so on. Constitutive promoters are functional in most or all tissues of an organism throughout development. "Inducible" promoters selectively express an operably linked DNA sequence in response to the presence of an endogenous or exogenous chemical inducer.

"Modulation" of expression refers to any change in expression, including but not limited to, increase in expression (e.g., induction), decrease in expression (e.g., repression), or change in the specificity or timing of expression (e.g., from constitutive to tissue-specific), or inducibility of expression, for example.

RNA polymerase II promoters, like those of other higher eukaryotes, are comprised of several distinct elements. One such element is the TATA box or Goldberg-Hogness box, which is required for correct expression of eukaryotic genes in vitro and accurate, efficient initiation of transcription in vivo. The TATA box is typically positioned at approximately −25 to −35, that is, at 25 to 35 basepairs (bp) upstream (5') of the transcription initiation site, or cap site, which is defined as position +1 (Breathnach and Chambon, *Ann. Rev. Biochem.* 50:349–383, 1981; Messing et al., In: *Genetic Engineering of Plants*, Kosuge et al., eds., pp. 211–227, 1983). Another common element, the CCAAT box, is located between −70 and −100 bp. In plants, the CCAAT box may have a different consensus sequence than the functionally analogous sequence of mammalian promoters (the plant analogue has been termed the "AGGA box" to differentiate it from its animal counterpart; Messing et al., In: *Genetic Engineering of Plants*, Kosuge et al., eds., pp. 211–227, 1983). In addition, virtually all promoters include additional upstream activating sequences or enhancers (Benoist and Chambon, *Nature* 290:304–310, 1981; Gruss et al., *Proc. Nat. Acad. Sci. USA* 78:943–947, 1981; and Khoury and Gruss, *Cell* 27:313–314, 1983) extending from around −100 bp to −1,000 bp or more upstream of the transcription initiation site.

When fused to heterologous DNA sequences, such promoters typically cause the fused sequence to have an expression pattern that is similar to that of the gene sequence with which the promoter is normally associated. Promoter fragments that include regulatory sequences can be added (for example, fused to the 5' end of, or inserted within, another active promoter having its own partial or complete regulatory sequences (Fluhr et al., *Science* 232:1106–1112, 1986; Ellis et al., *EMBO J.* 6:11–16, 1987; Strittmatter and Chua, *Proc. Nat. Acad. Sci. USA* 84:8986–8990, 1987; Poulsen and Chua, *Mol. Gen. Genet.* 214:16–23, 1988; Comai et al., *Plant Mol. Biol.* 15:373–381, 1991). Alternatively, heterologous regulatory sequences have been added to the 5' upstream region of an inactive, truncated promoter, e.g., a promoter including only the core TATA and, sometimes, the CCAAT elements (Fluhr et al., *Science* 232:1106–1112, 1986; Strittmatter and Chua, *Proc. Nat. Acad. Sci. USA* 84:8986–8990, 1987; Aryan et al., *Mol. Gen. Genet.* 225:65–71, 1991).

Promoters are typically comprised of multiple distinct "cis-acting transcriptional regulatory elements," or simply "cis-elements," each of which appears to confer a different aspect of the overall control of gene expression (Strittmatter and Chua, *Proc. Nat. Acad. Sci. USA* 84:8986–8990, 1987; Ellis et al., *EMBO J.* 6:11–16, 1987; Benfey et al., *EMBO J.* 9:1677–1684, 1990). Such cis elements bind trans-acting protein factors that regulate transcription. Some cis elements bind more than one factor, and trans-acting transcription factors may interact with different affinities with more than one cis element (Johnson and McKnight, *Ann. Rev. Biochem.* 58:799–839, 1989). Plant transcription factors, corresponding cis elements, and analysis of their interaction are discussed, for example, in: Martin, *Curr. Opinions Biotech.* 7:130–138, 1996; Murai, In: *Methods in Plant Biochemistry and Molecular Biology*, Dashek, ed., CRC Press, 1997, pp. 397–422; and *Methods in Plant Molecular Biology*, Maliga et al., eds., Cold Spring Harbor Press, 1995, pp. 233–300.

Promoters can be manipulated to produce synthetic or chimeric promoters that combine cis elements from two or more promoters, for example, by adding a heterologous regulatory sequence to an active promoter with its own partial or complete regulatory sequences (Ellis et al., *EMBO J.* 6:11–16, 1987; Strittmatter and Chua, *Proc. Nat. Acad. Sci. USA* 84:8986–8990, 1987; Poulsen and Chua, *Mol. Gen. Genet.* 214:16–23, 1988; Comai et al., *Plant. Mol. Biol.* 15:373–381, 1991). Chimeric promoters have also been developed by adding a heterologous regulatory sequence to the 5' upstream region of an inactive, truncated promoter (also referred to as a "minimal" promoter), i.e., a promoter that includes only the core TATA and, optionally, CCAAT elements (Fluhr et al., *Science* 232:1106–1:112, 1986; Strittmatter and Chua, *Proc. Nat. Acad. Sci. USA* 84:8986–8990, 1987; Aryan et al., *Mol. Gen. Genet.* 225:65–71, 1991). Cis elements can be obtained by chemical synthesis or by cloning from promoters that includes such elements, and they can be synthesized with additional flanking sequences that contain useful restriction enzyme sites to facilitate subsequent manipulation.

A "minimal" or "basal" promoter is capable of recruiting and binding RNA polymerase II complex and its accessory proteins to permit transcriptional initiation and elongation. However, a minimal promoter lacks cis sequences that recruit and bind transcription factors that modulate (e.g., enhance, repress, confer tissue specificity, confer inducibility or repressibility) transcription.

"Native". The term "native" is used interchangeably with the terms "wild type" or "naturally occurring."

"Heterologous". A "heterologous" sequence originates from a foreign source or species or, if from the same source, is modified from its original form.

"Isolated". An "isolated" nucleic acid sequence is substantially separated or purified away from other nucleic acid sequences with which the nucleic acid is normally associated in the cell of the organism in which the nucleic acid naturally occurs, i.e., other chromosomal or extrachromosomal DNA. The term embraces nucleic acids that are biochemically purified so as to substantially remove contaminating nucleic acids and other cellular components. The term also embraces recombinant nucleic acids and chemically synthesized nucleic acids.

Substantial Nucleotide Sequence Identity. The present invention encompasses polynucleotide sequences that are substantially identical to a native polynucleotide sequence, preferably comprising only conservative amino acid substitutions to a native sequence, and more preferably retaining functional similarity. When referring to a particular AHL synthase or AHL receptor gene, for example, such substantially similar sequences are included.

A first nucleic acid displays "substantially identity" to a reference nucleic acid sequence if, when optimally aligned (with appropriate nucleotide insertions or deletions totally 20 percent or less of the reference sequence over the window of comparison) with the other nucleic acid (or its complementary strand), there is at least about 75% nucleotide sequence identity, preferably at least about 80% identity, more preferably at least about 85% identity, and most preferably at least about 90% identity over a comparison window of at least 20 nucleotide positions, preferably at least 50 nucleotide positions, more preferably at least 100 nucleotide positions, and most preferably over the entire length of the first nucleic acid. Optimal alignment of sequences for aligning a comparison window may be conducted by the local homology algorithm of Smith and Waterman, *Adv. Appl. Math.* 2:482, 1981; by the homology alignment algorithm of Needleman and Wunsch, *J. Mol. Biol.* 48:443, 1970; by the search for similarity method of Pearson and Lipman, *Proc. Natl. Acad. Sci. USA* 85:2444, 1988; preferably by computerized implementations of these algorithms (GAP, BESTFIT, FASTA, and TFASTA in the Wisconsin Genetics Software Package Release 7.0, Genetics Computer Group, 575 Science Dr., Madison, Wis.). The reference nucleic acid may be a full-length molecule or a portion of a longer molecule.

Alternatively, two nucleic acids are substantially similar if one hybridizes to the other under stringent hybridization conditions, as defined below.

Codon usage bias. In order to optimize translation of a prokaryotic gene (such as a native gene encoding an AHL synthase or AHL receptor) in a eukaryotic host cell, one or more codons of the gene may be altered to reflect the codon usage bias of the eukaryotic host cell, that is, the codons that are statistically more highly represented in the genes of that cell than in the prokaryotic gene.

"Operably Linked". A first nucleic acid sequence is "operably" linked with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter effects or mediates transcription of the gene in a cell.

"Recombinant". A "recombinant" nucleic acid is made by an artificial combination of two otherwise separated segments of sequence, e.g., by chemical synthesis or by the manipulation of isolated segments of nucleic acids by genetic engineering techniques.

Techniques for nucleic acid manipulation are well-known. See, e.g., *Molecular Cloning: A Laboratory Manual,* 2nd ed., vol. 1–3, ed. Sambrook et al., Cold Spring Harbor Laboratory Press, Cold Spring Harbor, N.Y., 1989 (hereinafter, "Sambrook et al., 1989"); *Current Protocols in Molecular Biology,* ed. Ausubel et al., Greene Publishing and Wiley-Interscience, New York, 1992 (with periodic updates) (hereinafter, "Ausubel et al., 1992). Methods for chemical synthesis of nucleic acids are discussed, for example, in Beaucage and Carruthers, *Tetra. Letts.* 22:1859–1862, 1981, and Matteucci et al.,*J. Am. Chem. Soc.* 103:3185, 1981. Chemical synthesis of nucleic acids can be performed, for example, on commercial automated oligonucleotide synthesizers.

Preparation of Recombinant or Chemically Synthesized Nucleic acids; Vectors, Transformation, Host cells. Natural or synthetic nucleic acids according to the present invention can be incorporated into recombinant nucleic-acid constructs, typically DNA constructs, capable of introduction into and replication in a host cell. Such a construct preferably is a vector that includes a replication system (autonomous replication sequence [ARS] or origin of replication [ori]) and sequences that make possible the transcription and translation of a polypeptide-encoding sequence in a given host cell.

For the practice of the present invention, conventional compositions and methods for preparing and using vectors and host cells and examples of functional combinations of host cells and vectors are discussed, inter alia, in Sambrook et al., 1989, or Ausubel et al., 1992. Promoter and other necessary vector sequences are selected so as to be functional in a particular host cell.

A number of vectors suitable for stable transfection of plant cells or for the establishment of transgenic plants have been described in, e.g., Pouwels et al., *Cloning Vectors: A Laboratory Manual,* 1985, supp. 1987); Weissbach and Weissbach, *Methods for Plant Molecular Biology,*Academic Press, 1989; and Gelvin et al., *Plant Molecular Biology Manual,* Kluwer Academic Publishers, 1990. Typically, eukaryotic expression vectors include, for example, one or more cloned genes under the transcriptional control of 5' and 3' regulatory sequences and a selectable marker. Regulatory control sequences include, but are not limited to, a promoter (including a transcription initiation start site), a ribosome binding site, an RNA processing signal, a transcription termination site, and/or a polyadenylation signal. Regulatory sequences from the 3'-untranslated region of plant genes include, for example, 3' terminator regions to increase mRNA stability of the mRNA, such as the PI-II terminator region of potato or the octopine or nopaline synthase 3' terminator regions (Thornburg et al., *Proc. Natl. Acad. Sci. USA* 84:744, 1987); An et al., *Plant Cell* 1:115 (1989). Any well known selectable marker gene may be used, including, for example, genes encoding antibiotic resistance genes (e.g., resistance to hygromycin, kanamycin, bleomycin, G418, streptomycin or spectinomycin); and herbicide resistance genes (e.g., phosphinothricin acetyltransferase). Such 5' and 3' regulatory sequences, transcription termination sequences, polyadenylation signals, selectable markers, etc. for use in other eukaryotic cells, e.g., in yeast, mammalian, or other cell types, are well known in the art.

Examples of constitutive plant promoters useful for plant gene expression include, constitutive plant promoters, including, but not limited to, the cauliflower mosaic virus (CaMV) 35S promoter, which confers constitutive, high-level expression in most plant tissues (see, e.g., Odel et al., Nature 313:810, 1985), including monocots (see, e.g., Dekeyser et al., Plant Cell 2:591, 1990; Terada and Shimamoto, Mol. Gen. Genet. 220:389, 1990); the nopaline synthase promoter (An et al., Plant Physiol. 88:547, 1988) and the octopine synthase promoter (Fromm et al., Plant Cell 1:977, 1989).

It may also be advantageous to utilize a quorum sensing system according to the present invention to regulate the expression of transgenes in organelles, including plastids such as chloroplasts and mitochondria. For example, a gene encoding a polypeptide comprising (1) a organelle (e.g., chloroplast)-targeting sequence fused in-frame with (2) an AHL receptor polypeptide (e.g., LuxR) is expressed from an expression cassette in the nuclear genome of the plant cell. The AHL receptor is targeted to the organelle by the targeting sequence and activated by the AHL inducer to modulate the activity of an AHL-responsive promoter in the organellar genome. Alternatively, a gene encoding the AHL receptor can be expressed within the organelle, e.g., by incorporation into the organellar genome, under the control of a promoter that is functional in the organelle to modulate expression of an AHL-responsive promoter in the organelle. As an option in either case, the AHL synthase (e.g., LuxI) could be expressed either in the nucleus or organelle.

The expression constructs may be prepared to direct the expression of the transcriptional regulator from the plant cell nucleus, and the DNA sequence of interest expressed from the regulatable promoter in the plant cell plastid. Such constructs may require the use of a chloroplast transit peptide (CTP), such as the CTP of the ribulose-bisphosphate carboxylase small subunit (ssuCTP), to direct the activator/repressor protein to the plant cell plastid. Methods for the regulated transcription of DNA sequences in the plastid using controlling sequences expressed from the nucleus are described for example in U.S. Pat. No. 5,576,198.

Furthermore, expression constructs may be prepared to direct the expression of both the transcriptional regulator and the DNA sequence of interest from the plant cell plastid.

Nucleic-Acid Hybridization; "Stringent Conditions"; "Specific". The nucleic-acid probes and primers of the present invention hybridize under stringent conditions to a target DNA sequence. The term "stringent conditions" is defined as conditions under which a probe or primer hybridizes specifically with a target sequence(s) and not with non-target sequences, as can be determined empirically. The term "stringent conditions" is functionally defined with regard to the hybridization of a nucleic-acid probe to a target nucleic acid (i.e., to a particular nucleic-acid sequence of interest) by the specific hybridization procedure discussed in Sambrook et al., 1989, at 9.52–9.55. See also, Sambrook et al., 1989, at 9.47–9.52, 9.56–9.58; Kanehisa, Nucl. Acids Res. 12:203–213, 1984; and Wetmur and Davidson, J. Mol. Biol. 31:349–370, 1968. Preferably, hybridization using DNA or RNA probes or primers is performed at 65° C. in 6×SSC, 0.5% SDS, 5× Denhardt's, 100 µg/mL nonspecific DNA (e.g., sonicated salmon sperm DNA) with washing at 0.5×SSC, 0.5% SDS at 65° C. Lower hybridization and/or washing temperatures may be used to identify related sequences having a lower degree of sequence similarity if specificity of binding of the probe or primer to target sequence(s) is preserved.

Regarding the amplification of a target nucleic-acid sequence (e.g., by PCR) using a particular amplification primer pair, "stringent conditions" are conditions that permit the primer pair to hybridize only to the target nucleic-acid sequence to which a primer having the corresponding wild-type sequence (or its complement) would bind and preferably to produce a unique amplification product.

Fragments, Probes, and Primers. A fragment of a nucleic acid is a portion of the nucleic acid that is less than full-length and comprises at least a minimum length capable of hybridizing specifically with a native nucleic acid under stringent hybridization conditions. The length of such a fragment is preferably at least 15 nucleotides, more preferably at least 20 nucleotides, and most preferably at least 30 nucleotides of a native nucleic acid sequence.

Nucleic acid probes and primers can be prepared based on a native gene sequence. A "probe" is an isolated nucleic acid to which is attached a conventional detectable label or reporter molecule, e.g., a radioactive isotope, ligand, chemiluminescent agent, or enzyme. "Primers" are isolated nucleic acids that are annealed to a complementary target DNA strand by nucleic acid hybridization to form a hybrid between the primer and the target DNA strand, then extended along the target DNA strand by a polymerase, e.g., a DNA polymerase. Primer pairs can be used for amplification of a nucleic acid sequence, e.g., by the polymerase chain reaction (PCR) or other conventional nucleic-acid amplification methods.

Probes and primers are generally 15 nucleotides or more in length, preferably 20 nucleotides or more, more preferably 25 nucleotides, and most preferably 30 nucleotides or more. Such probes and primers hybridize specifically to a target DNA or RNA sequence under high stringency hybridization conditions. Preferably, probes and primers according to the present invention have complete sequence similarity with a target sequence, although probes differing from a target sequence that retain the ability to hybridize to the target sequence may be designed by conventional methods.

Methods for preparing and using probes and primers are described, for example, in Sambrook et al., 1989; Ausubel et al., 1992; and Innis et al., PCR Protocols: A Guide to Methods and Applications, Academic Press: San Diego, 1990. PCR-primer pairs can be derived from a known sequence, for example, by using computer programs intended for that purpose such as Primer (Version 0.5, © 1991, Whitehead Institute for Biomedical Research, Cambridge, Mass.).

Nucleic-Acid Amplification. As used herein, "amplified DNA" refers to the product of nucleic-acid amplification of a target nucleic-acid sequence. Nucleic-acid amplification can be accomplished by any of the various nucleic-acid amplification methods known in the art, including the polymerase chain reaction (PCR). A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990.

Nucleotide-Sequence Variants of Native Nucleic Acids. Using the nucleotide and the sequence of the promoters disclosed herein, those skilled in the art can create DNA molecules that have minor variations in their nucleotide sequence.

"Variant" DNA molecules are DNA molecules containing changes in which one or more nucleotides of a native DNA sequence is deleted, added, and/or substituted, preferably while substantially maintaining promoter function, or, in the case of a promoter fragment, of affecting the transcription of a minimal promoter to which it is operably linked. Variant DNA molecules can be produced, for example, by standard DNA mutagenesis techniques or by chemically synthesizing the variant DNA molecule or a portion thereof.

One or more base pairs may be deleted from the 5' or 3' end of a promoter sequence to produce a "truncated" promoter. One or more base pairs may be inserted, deleted, or substituted internally to a promoter sequence. Promoters may be constructed in which promoter fragments or elements are operably linked, for example, by placing such a fragment upstream of a minimal promoter. Substitutions, deletions, insertions or any combination thereof can be combined to produce a final construct.

Transformation

A cell, tissue, organ, or organism into which has been introduced a foreign nucleic acid, such as a recombinant vector, is considered "transformed", "transfected", or "transgenic." A "transgenic" or "transformed" cell or organism also includes progeny of the cell or organism. In the case of plants, a "transgenic" or "transformed" cell also includes progeny produced from a breeding program employing such a "transgenic" plant as a parent in a cross and exhibiting an altered phenotype resulting from the presence and expression of a recombinant nucleic acid construct.

Any plant variety may be used in the practice of the present invention including, but not limited to monocotyledonous and dicotyledonous crop plants such as corn, soybean, wheat, rice, barley, *Brassica* (e.g., oilseed rape), cotton, flax, sunflower, safflower, sorghum, tobacco, lettuce, carrot, broccoli and cauliflower, watermelon, tomato, cantaloupe, pumpkin, etc.

Methods of Controlling Eukaryotic Gene Expression

Nucleic acid constructs as described above, particularly expression vectors that include a gene of interest that is expressed under the control of an AHL-responsive promoter, are useful in a wide variety of contexts.

In transgenic plants, for example, such constructs can be used for making male- or female-sterile plants, by using an AHL-responsive promoter to modulate the expression of a gene that affects reproductive function, for example by killing a male or female reproductive tissue, rendering a male or female reproductive tissue sensitive to damage by an exogenous chemical compound such as an herbicide or antibiotic, or interfering with normal development or function of a male or female reproductive tissue, for example. Such male- or female-sterile plants are useful for hybrid breeding. See, e.g., U.S. Pat. Nos. 5,356,799, 5,478,369, 5,633,441, 5,689,041, 5,723,763, 5,728,558, 5,728,926, 5,741,684, 5,750,867, 5,767,374; EP 329,308, 412,911; and WO 90/08828.

In transgenic plants that are transformed with vectors that include not only an AHL receptor-encoding gene and both a gene of interest and an AHL synthase-encoding gene transcribed under the control of a corresponding AHL-responsive promoter, one-time application of an appropriate AHL causes expression of the gene of interest in a continuing fashion as a result of continued synthesis of the AHL in the plant via autoinduction. Therefore, the AHL can be applied as a seed coating, or by means of a spray or other form of application at an appropriate time to stimulate AHL-responsive gene expression. Expression of the gene of interest can be restricted to a desired tissue or organ, for example, by use of a tissue- or organ-specific promoter to drive expression of the AHL receptor-encoding gene.

Formulations of AHLs for Modulation of Plant Gene Expression

The present invention encompasses formulations that include an amount of one or more AHLs that is effective to modulate the expression of a gene in a cell, e.g., a plant cell, that has been placed under the control of an AHL-responsive promoter.

Such compositions (preferably aqueous compositions), when applied to plants, are applied to foliage, to the soil, or to the water surface (e.g., in a rice field). Such compositions can also be applied as a seed treatment, for example, by soaking seeds in a liquid formulation containing the a compound according to the invention or by coating seeds with the compound.

According to another aspect of the invention, compositions are provided that include one or more compounds according to the invention and, optionally, other active and inactive ingredients. For example, the compounds of the invention can be used in combination with other active or inactive ingredients, such as plant growth regulators, herbicides, fungicides, insecticides, nematicides, and bactericides, for example.

A compound of the invention can be applied to the growth medium or to plants to be treated either by itself or as a component of a formulation that also includes an agronomically acceptable carrier and optionally other active ingredients, including other compounds of the invention. By "agronomically acceptable carrier" is meant any liquid or solid substance that can be used to dissolve, disperse, or diffuse a compound in the composition without impairing the effectiveness of the compound and which by itself has no significant detrimental effect on the soil, equipment, crops, or agronomic environment. Such compositions include liquid or solid formulations or solutions, including wettable powders, emulsifiable concentrates, dusts, granules, pellets, aerosols, flowable emulsion concentrates, suspensions, and solutions, which may be prepared according to any conventional method. A composition containing a compound of the invention can be diluted with an agronomically suitable liquid or solid carrier. Such compositions can also include one or more agronomically acceptable adjuvants such as anionic, cationic, or nonionic surface-active agents (wetting agents, spreading agents, dispersing agents, suspending agents, and emulsifying agents), conditioning agents, sticking agents, adhesives, etc. Examples of useful adjuvants can be found in "Detergents and Emulsifier's Annual" (John W. McCutcheon, Inc.)

Preferred compositions include liquids and wettable powders, preferably containing as a conditioning agent one or more surface-active agents in amounts sufficient to render the active ingredient(s) readily dispersible in water or in oil. The incorporation of a surface-active agent into the compound can enhance its efficacy. Suitable wetting agents include but are not limited to alkyl benzene and alkyl naphthalene sulfonates, sufonated fatty alcohols, amines or acid amides, long chain acid esters of sodium isothionate, esters of sodium sulfonsuccinate, sulfated or sulfonated fatty acid esters, petroleum sulfonates, sulfonated vegetable oils, ditertiary acetylenic glycols, polyoxyethylene derivatives or alkylphenyls (particulary isooctylphenol and nonylphenol) and polyoxyethylene derivatives of the nono-higher fatty acid esters of hexitol anhydrides (e.g., sorbitan). Surfactants include but are not limited to the dihexyl ester of sodium sulfonsuccinic acid, POE 20 sorbitan monolaurate, and octyllphenoxy polyethoxy ethanol. Wettable powders or dispersable granules are water-dispersible compositions containing one or more active ingredients, an inert solid extender, and one or more wetting and dispersing agents. The inert solid extenders are usually of mineral origin such as the natural clays, diatomaceous earth, salts and synthetic minerals, derived from silica and the like. Examples of such extenders include kaolinites, attapulgite clay, salts and synthetic magnesium silicate.

Compounds of the invention can be dissolved in any suitable solvent, including but not limited to one or a mixture of the following: water, alcohols, ketones, aromatic hydrocarbons, halogenated hydrocarbons, dimethylformamide, dioxane, and dimethylsulfoxide. The concentration of the active ingredient in the resulting solution can be determined empirically.

In order to produce emulsifiable concentrates, the compounds of the invention are dissolved in an organic solvent such as benzene, toluene, xylene, methylated naphthalene, corn oil, terpentine, o-dichlorobenzene, isophorone, cyclohexane, or methyl oleate, or mixtures thereof, together with a conventional emulsifying agent that allows dispersion in water, e.g., ethylene oxide derivatives of alkylphenols or long-chain alcohols, mercaptans, carboxylic acids, reactive amines, and partially esterified polyhydric alcohols. Solvent-soluble sulfates or sulfonates, such as the alkaline earth salts or amine salts of alkylbenzenesulfonates and the fatty alcohol sodium sulfates, having surface-active properties can be used as emulsifiers either alone or in conjunction with an ethylene oxide reaction product. Flowable emulsion concentrates are similarly formulated and include, in addition to the foregoing components of emulsifiable concentrates, water and a stabilizing agent such as a water-soluble cellulose derivative or a water-soluble salt of a polyacrylic acid. The concentration of the active ingredient in such emulsifiable concentrates is generally about 10% to 60% by weight and in free-flowing emulsion concentrates is generally about 10% to 75% by weight.

Wettable powders suitable for spraying are mixtures of a compound according to the invention, a finely divided solid (such as a clay, an organic silicate or carbonate, or a silica gel), and a wetting agent, sticking agent, and/or dispersing agent. The concentration of the active ingredient(s) in such powders is generally between about 20% and 98% by weight and is preferably between about 40% and 75% by weight. A dispersion agent is optionally present in an concentration of about 0.5% to 3% by weight of the composition. A wetting agent may constitute from about 0.1% to 5% by weight of the composition.

Dusts are mixtures of one or more compounds of the invention with finely divided inert organic or inorganic solids such as botanical flours, farina, diatomite, silicas, silicates, carbonates, and clays. One method for preparing a dust is to dilute a wettable powder with a finely divided carrier. A dust concentrate containing from about 20% to 80% of the active ingredient(s) can be diluted to a final concentration of about 1% to about 10% by weight of the dust.

Particulate (e.g., granular) formulations are prepared by impregnating the active ingredient(s) into a solid material, such as granular fuller's earth, vermiculite, ground corn cobs, cornmeal, seed hulls (including bran or other grain hulls), or other materials. A solution of one or more of the compounds of the invention in a volatile organic solvent is sprayed or mixed with the granular solid and the solvent is removed by evaporation. The granular material can have any suitable size, preferably from about 16 to about 60 mesh. The active ingredient generally represents about 2% to about 15% by weight of the formulation. Alternatively, the formulation can be incorporated into controlled-release particulate formulations by standard methods, e.g., by encapsulation by interfacial polymerization and coacervation; dissolving the active ingredient in a solution together with a polymer followed by solvent evaporation; by mixing the active ingredient with a wax or polymer (by mixing dry ingredients followed by melting the mixture, or by mixing the active ingredient with a molten wax or polymer, followed by solidification of the mixture), then producing particles of the mixture by prilling, milling, extrusion, spray chilling, etc. The active ingredient generally represents between about 5% and 50% of such a controlled-release formulation.

Salts of the compounds of the invention can be formulated and applied as aqueous solutions at a concentration of between about 0.05% to about 50% by weight and preferably from about 0.1% and 10% by weight and applied to crops in this form. Such solutions can be prepared as concentrates that are diluted with an aqueous solvent or other appropriate solvent to the desired concentration for use. Such solutions optionally include a surface active agent and/or one or more auxiliary materials to increase the activity of the active ingredient, such as glycerin, methylethylcellulose, hydroxyethyl cellulose, polyoxyethylenesorbitan monooleate, polypropylene glycol, polyacrylic acid, polyethylene sodium malate, or polyethylene oxide, etc. Such auxiliary materials are generally present at a concentration of about 0.1% to 5% by weight, preferably from about 0.5% to about 2% by weight of the solution. Such compositions can also optionally include an agronomically acceptable surfactant.

The compounds and formulations of the invention can be applied by conventional method, including but not limited to hydraulic sprays, aerial sprays, or dusts. For low-volume applications a solution of the compound is usually used. The optimum formulation, volume, concentration, application rate, timing of application (including stage of plant development), and method of application will depend on a variety of factors such as plant type, soil type, fertility, environmental factors, etc.

As used herein, the term "effective amount" refers to an amount of an AHL or AHL analog (or mixture including two or more AHLs or AHL analogs) in a composition that is sufficient to modulate the expression of a gene under the control of an AHL-responsive promoter, preferably an induction or reduction of expression that is at least two-fold, preferably five-fold, and more preferably at least ten-fold compared to basal activity in the absence of the AHL.

Formulations of AHLs for Modulation of Animal Gene Expression

The present invention is useful for modulating gene expression in a wide variety of animals or animal cells or tissues, including fungi (e.g., yeast such as *Saccharomyces cerevisiae*), nematodes, insects, amphibians, avians, and mammals, for example. Any conventional formulation can be used to deliver an AHL to such a cell, tissue, or organism.

EXAMPLES

Example 1

Inducers

The inducer for the control of the *Vibrio fisheri* lux system, N-(3-oxohexanoyl)-L-homoserine lactone (OHHL, also referred to as VAI-1) are synthesized or obtained from a commercial source. Methods for the production of the OHHL inducer are described by Eberhard et al., *Biochemistry* 20:2444–2449, 1981. Other AHL inducers may be obtained from commercial sources.

Example 2

Expression Constructs

2A. Nuclear Expression Constructs

A series of effector and reporter constructs are prepared to direct the expression of the LuxR and related proteins and the lux box-GUS respectively. The effector constructs contain the transcriptional regulator, and the reporter constructs contain the regulatable promoter harboring the lux box sequences.

Reporter constructs employing the iudA reporter gene (Jefferson et al., *Proc. Natl. Acad. Sci.*, 83:8447–8451, 1986) operably associated with the luxR box are prepared as described below. Double stranded oligonucleotides encoding for LuxR or homologous binding sites are cloned in multiple copies into a minimal 35S promoter-GUS reporter construct. The sequences of the oligonucleotides are as follows:

EsaR box
5'-AACTTAACCTGCACTATAGTACAGGTAACA-3' (SEQ ID NO:23)
LuxI box
5'-AACTTAACCTGTAGGATCGTACAGGTAACA-3' (SEQ ID NO:24)
LasB box
5'-AACTTAACCTGCCAGTTCTGGCAGGTAACA-3' (SEQ ID NO:25)
TraR-box
5'-AACTTAACGTGCAGATCTGCACATAACA-3' (SEQ ID NO:26)

Figure 4:
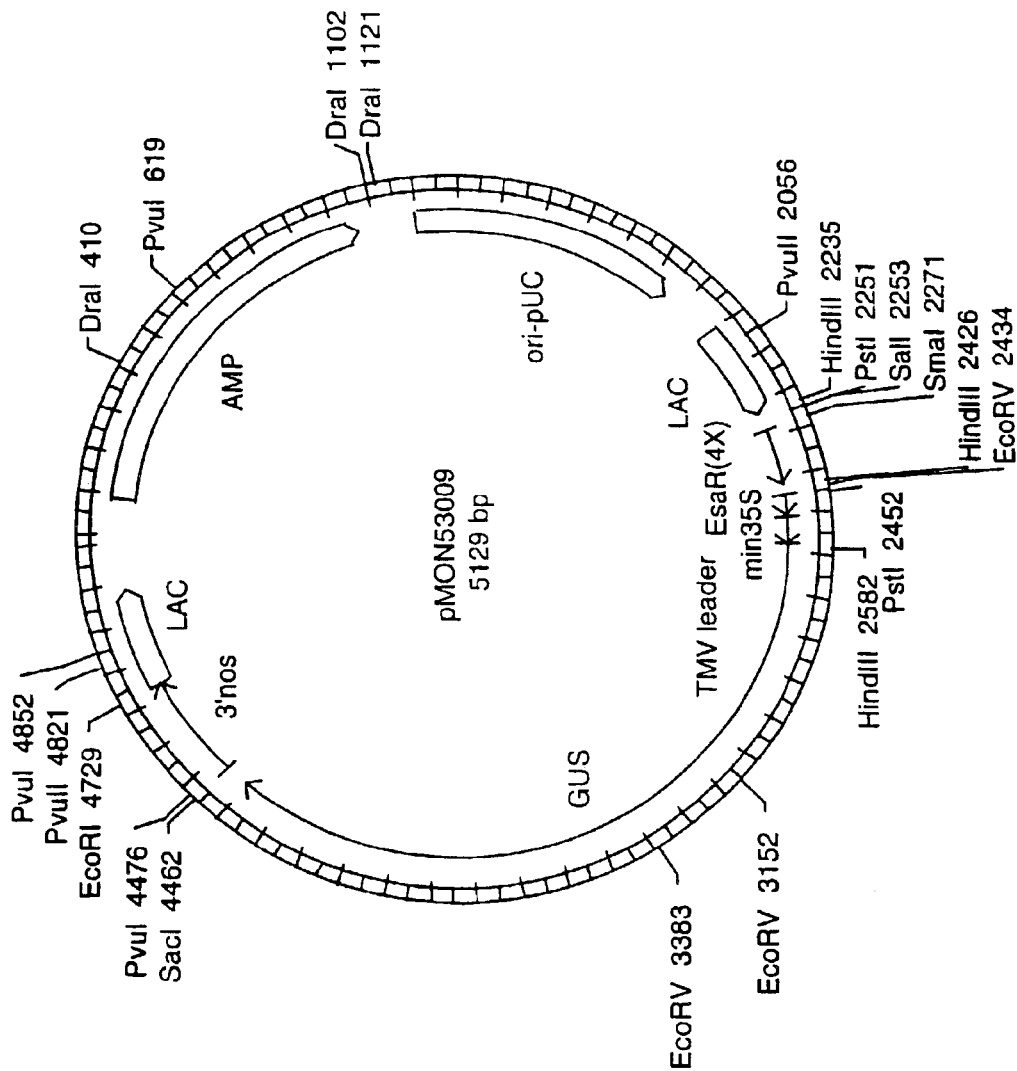
FIG. 4 provides a schematic representation of the expression construct pMON53009.

An example of the reporter construct, pMON53009, for EsaR is shown in FIG. 4. Four copies of the EsaR-box oligonucleotide are cloned upstream of the minimal (−46 truncated) CAMV 35S promoter. The minimal 35S promoter is followed by the W translational enhancer from TMV coat protein, *E. coli* β-glucuronidase iudA gene (GUS), and the 3'-untranslated region from nopaline synthase gene (3'NOS), which provides a transcriptional terminator and a polyadenylation signal. Constructs for other members of LuxR family are identical with the exception of the number of copies and the sequence of the oligonucleotide encoding for the putative binding site. The constructs are described as follows, with the sequence of the cis-element, or transcriptional regulator binding site underlined.

The construct pMON53006 contains three copies of the luxR box (5'-AACTTAACCTGTAGGATCGTACAGGTAACA-3'; SEQ ID NO:27) cloned upstream of the minimal 35S promoter (FIG. 1).

Figure 2:
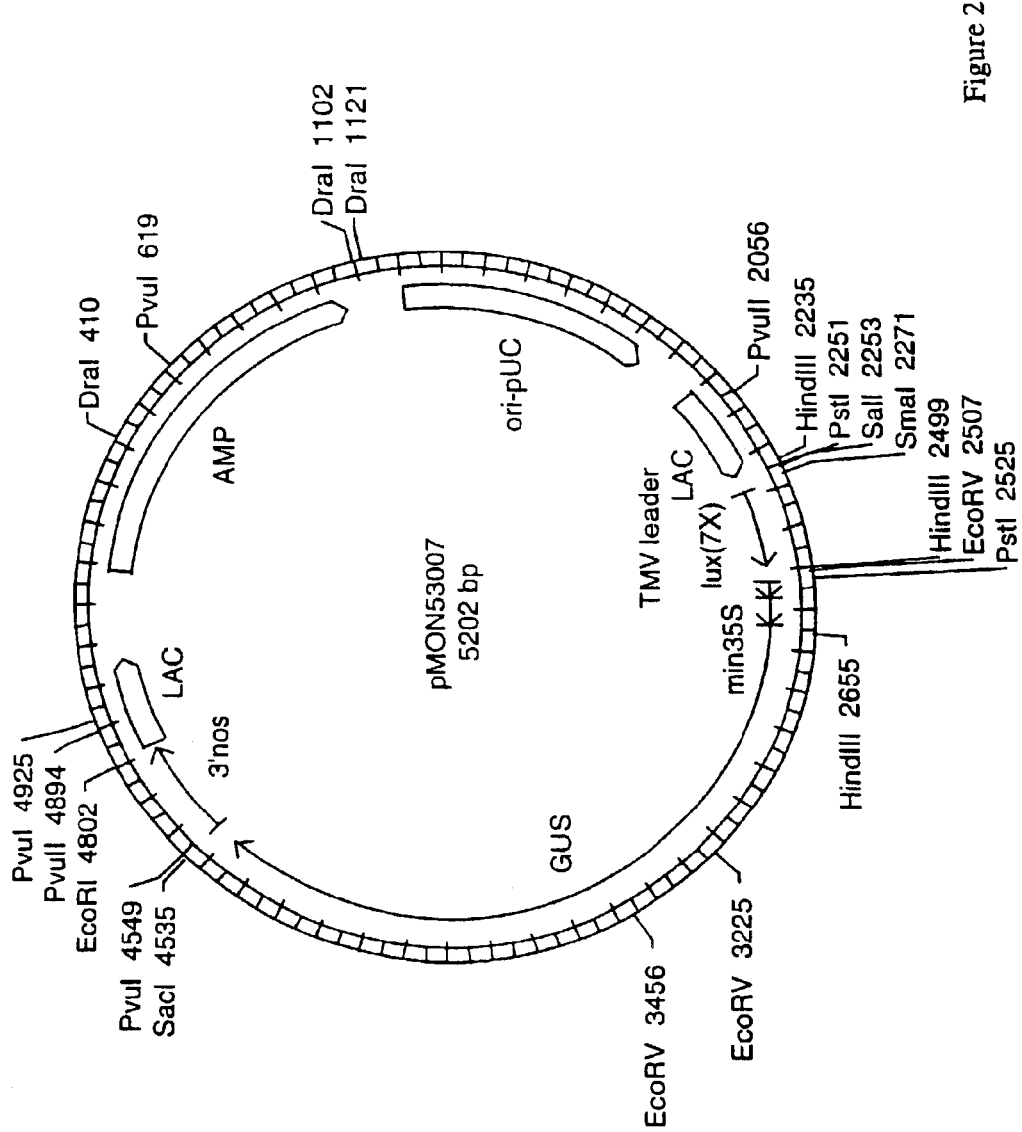
FIG. 2 provides a schematic representation of the expression construct pMON53007.

The construct pMON53007 contains seven copies of the luxR box (5'-AACTTAACCTGTAGGATCGTACAGGTAACA-3'; SEQ ID NO:28) cloned upstream of the minimal 35S promoter (FIG. 2).

Figure 3:
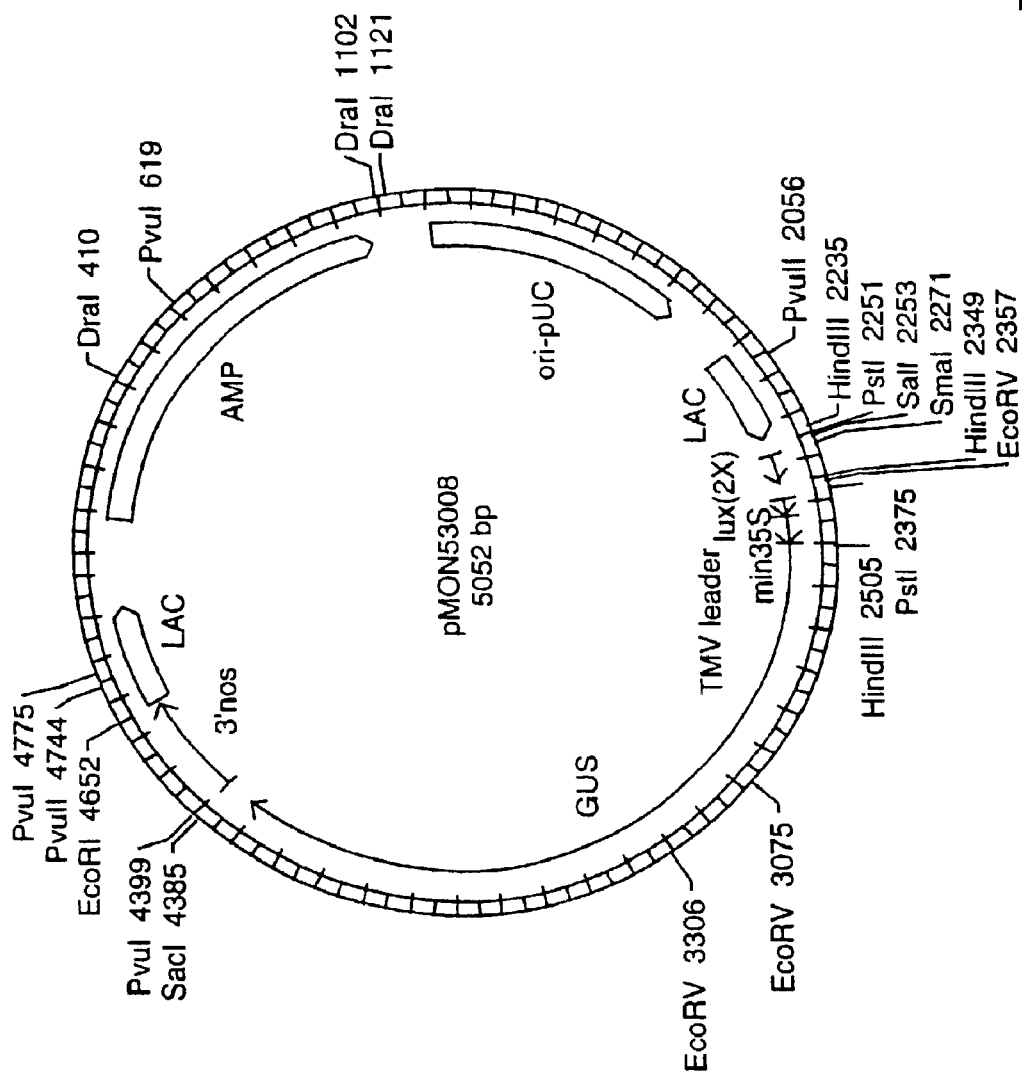
FIG. 3 provides a schematic representation of the expression construct pMON53008.
Figure 5:
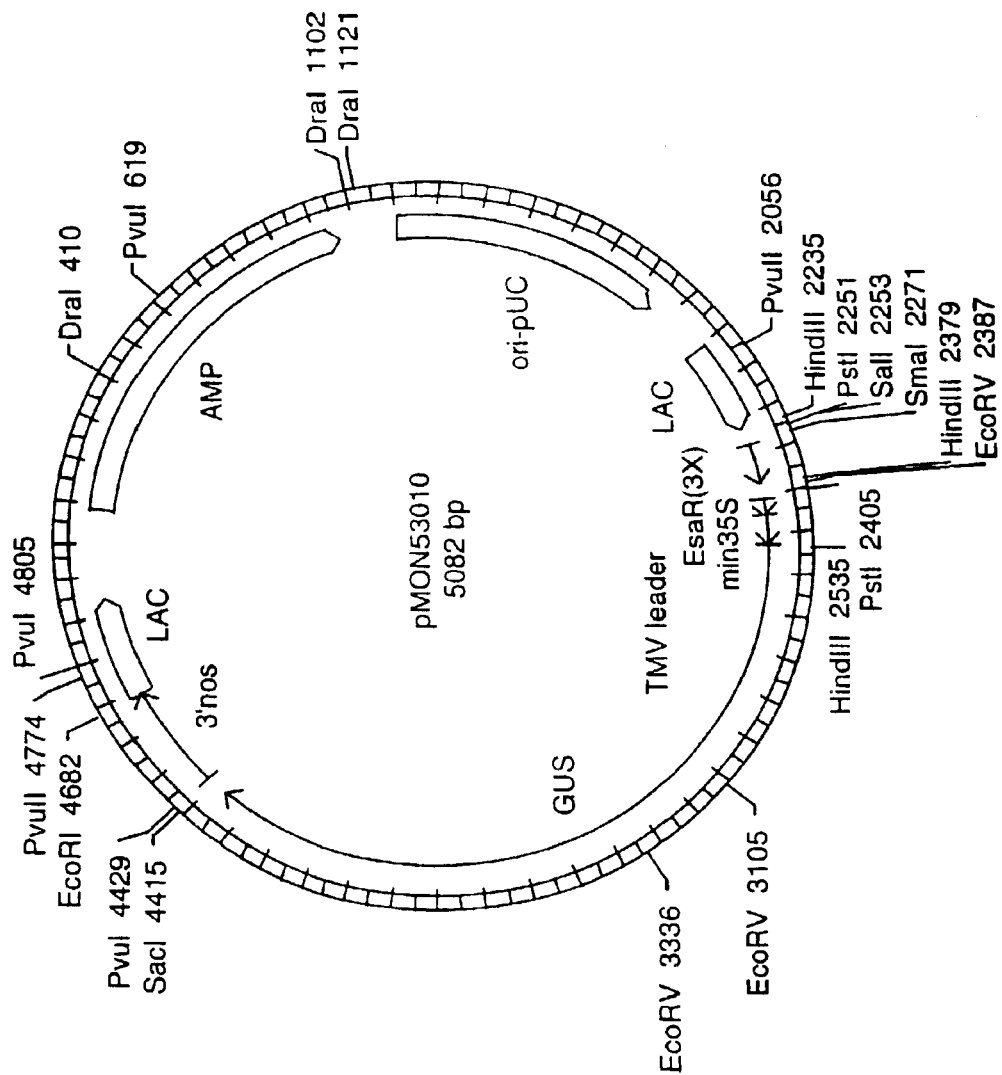
FIG. 5 provides a schematic representation of the expression construct pMON53010.

The construct pMON53008 contains two copies of the luxR box (5'-AACTTAACCTGTAGGATCGTACAGGTAACA-3'; SEQ ID NO:29) cloned upstream of the minimal 35S promoter (FIG. 3). The construct pMON53009 contains four copies of the esaR box (5'-AACTTAACCTGCACTATAGTACAGGTAACA-3'; SEQ ID NO:30) cloned upstream of the minimal 35S promoter (FIG. 4). The construct pMON53010 contains three copies of the esaR box (SEQ ID NO:31) (5'-AACTTAACCTGCACTATAGTACAGGTAACA-3') cloned upstream of the minimal 35S promoter (FIG. 5). The construct pMON53031 contains three copies of the traII box (5'-AACTTAACGTGCAGATCTGCACATAACA-3'; SEQ ID NO:32) cloned upstream of the minimal 35S promoter (FIG. 6).

Figure 6:
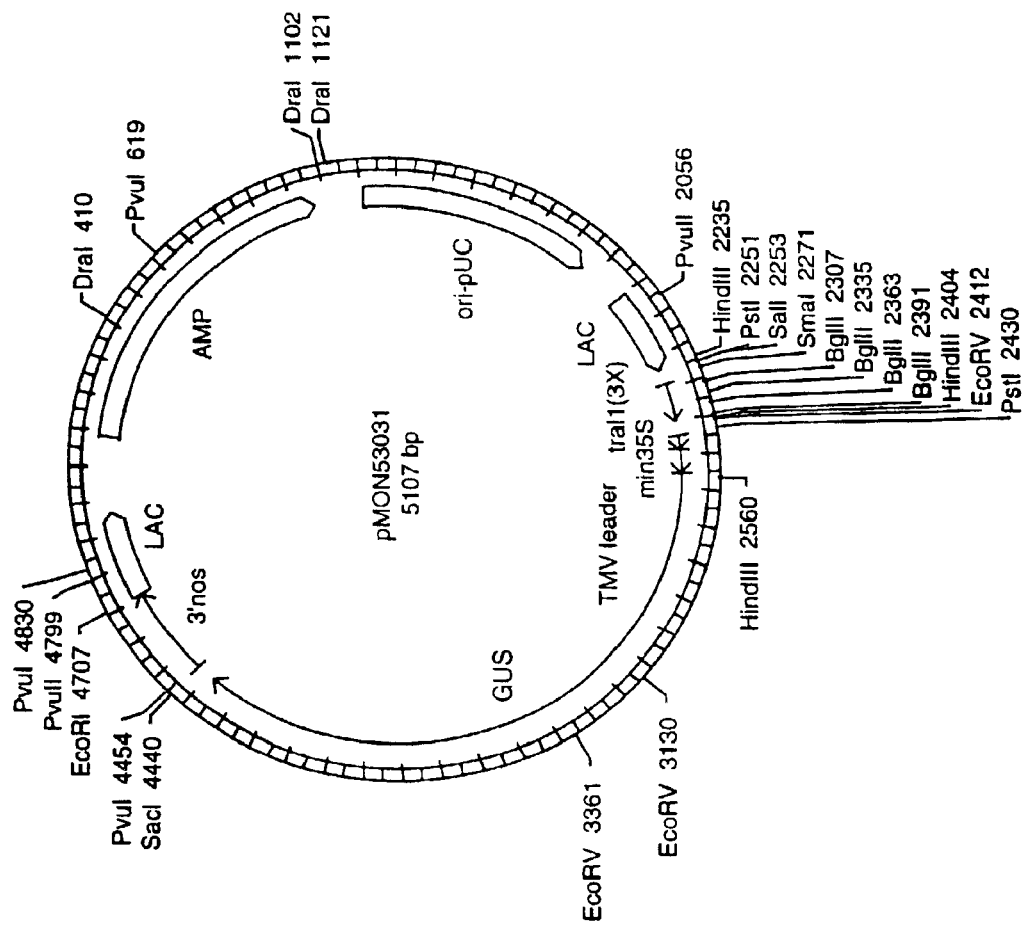
FIG. 6 provides a schematic representation of the expression construct pMON53031.

The construct pMON53032 contains six copies of the traII box (SEQ ID NO:33) (5'-AACTTAACGTGCAGATCTGCACATAACA-3') cloned upstream of the minimal 35S promoter (similar to FIG. 6, only having 6 copies of the traII box sequence).

Figure 7:
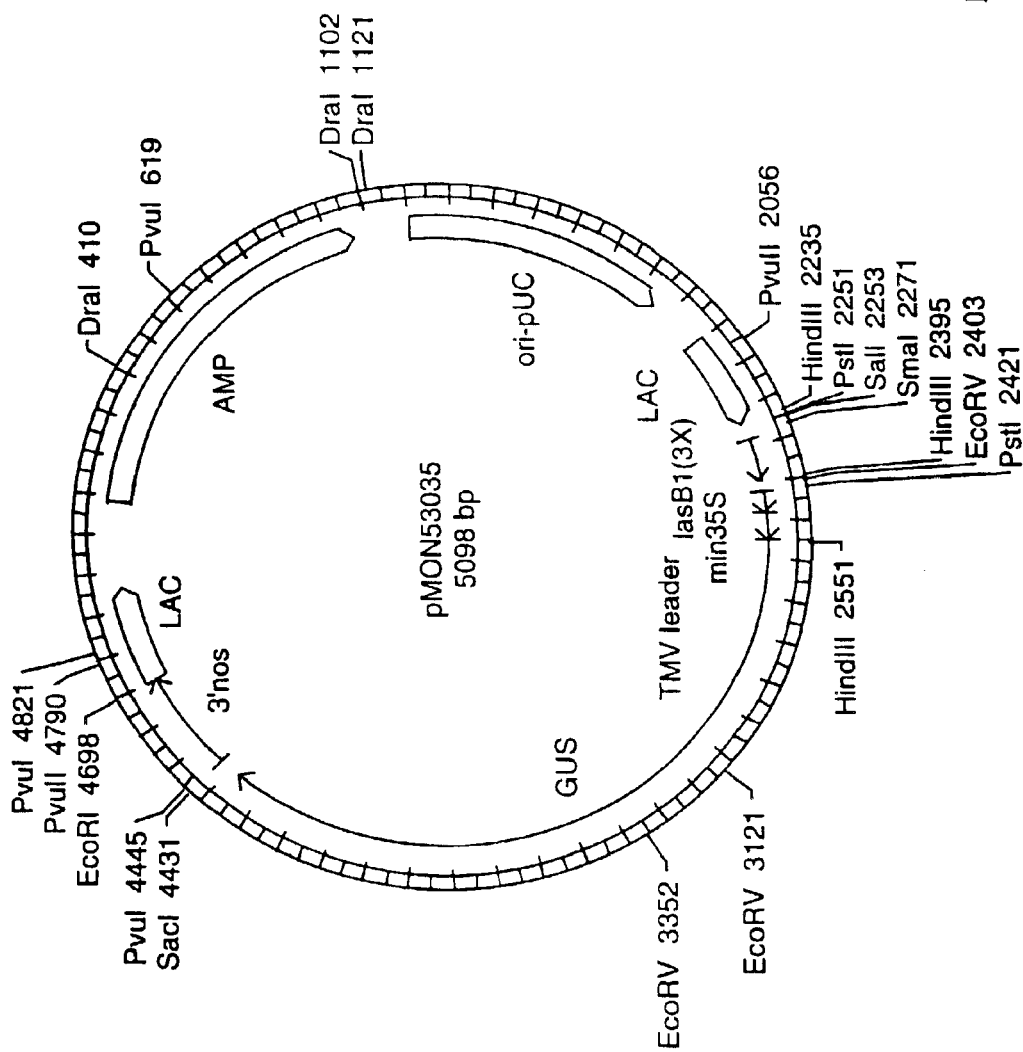
FIG. 7 provides a schematic representation of the expression construct pMON53035.

The construct pMON53035 contains three copies of the lasB box (5'-AACTTAACCTGCCAGTTCTGGCAGGTAACA-3'; SEQ ID NO:34) cloned upstream of the minimal 35S promoter (FIG. 7).

Figure 8:
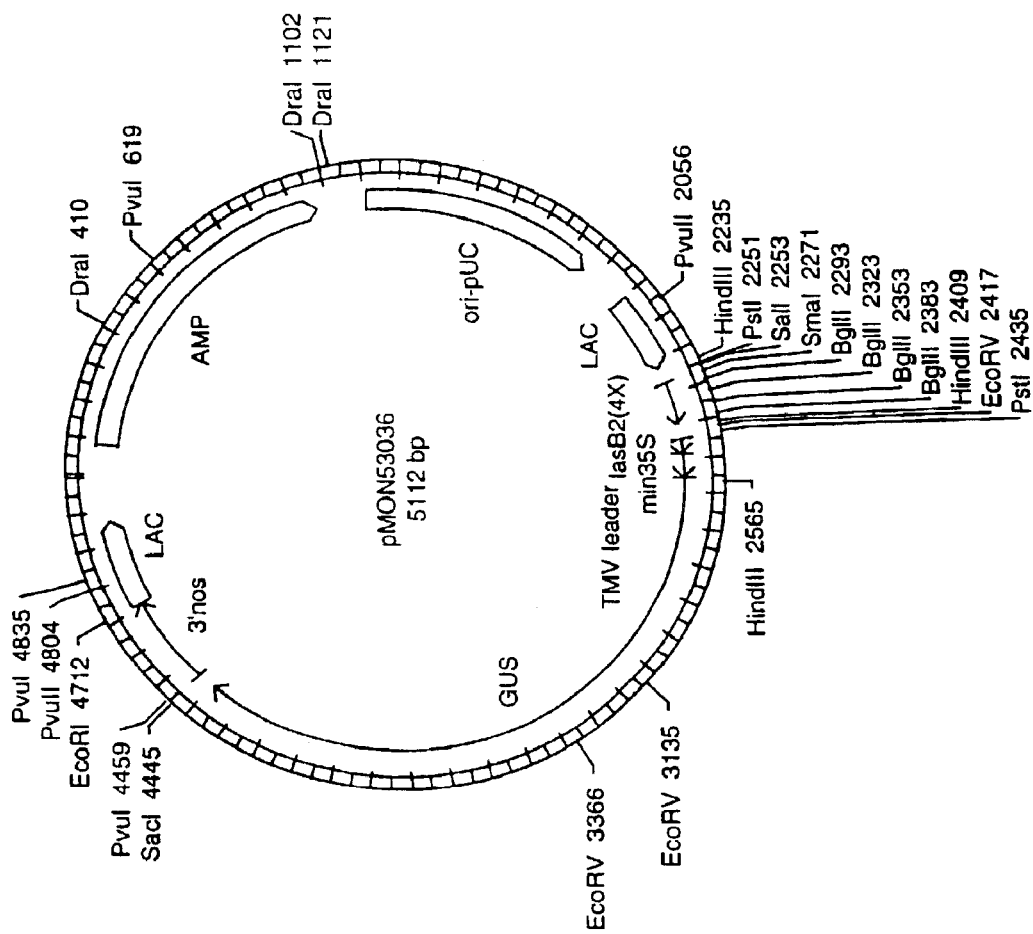
FIG. 8 provides a schematic representation of the expression construct pMON53036.

The construct pMON53036 contains four copies of the lasB box (5'-AACTTAACCTGCCAGTTCTGGCAGGTAACA-3'; SEQ ID NO:35) cloned upstream of the minimal 35S promoter (FIG. 8).

A series of effector constructs are prepared employing various bacterial regulators. LuxR, EsaR, LasR, RhlR and TraR open reading frames have been isolated from bacterial chromosomal DNA using PCR. The primers for amplification of the regulators are as follows: LuxR (LuxR-N 5'-TGAAAAAGATAAATGCCGACGACACATACAGAA; SEQ ID NO:36 and LuxR-Cla SEQ ID NO:37 5'-AGCTTTATCGATGTACTTAATTTTTAAAGTATGG from *Vibrio*), EsaR (EsaR-Nde 5'-GGAGCCCATATGTTTTCTTTTTTCCTTGAAAAT; SEQ ID NO:38 and EsaR-Cla 5'-ACGTACGATCGATCCGCCCGTCGCAGTCACTAC; SEQ ID NO:39), LasR (LasR-Nde 5'-GTAGCCATATGGCCTTGGTTGACGGTTTTC; SEQ ID NO:40 and LasR-Cla 5'-CATCGATCTGAGAGGCAAGATCAGAGAGTA; SEQ ID NO:41), RhlR (RhlR-Nde 5'-CTTACTCATATGAGGAATGACGGAGGCTTT; SEQ ID NO:42 and RhlR-C 5'-CTGCGCTTCAGATGAGGCCCAGCGCCGCGG; SEQ ID NO:43) and TraR (TraR25' 5'-CATATGCAGCACTGGCTGG; SEQ ID NO:44 and TraR13' 5'-GTCGACCTCAGATGAGTTTCCG; SEQ ID NO:45 from *Agrobacterium* strain A348). PCR fragments containing open reading frames are cloned into an expression construct. The vector construct contains a modified 35S promoter (double enhancer) followed by the TMV coat protein translational enhancer (W-leader), HA (hemoinfluenza) epitope (MGYPYDVPDYAH; SEQ ID NO:46) and the 3' untranslated region from nopaline synthase gene (3'NOS), which provides a transcriptional terminator and a polyadenylation signal. The 17 bp region of the 35S promoter (−17 to −1), which is immediately upstream of the start of transcription (pos. +1), is replaced with the sequence of the bacteriophage T7 promoter. The resulting chimeric 35S/T7 promoter has the advantage over the original 35S promoter in that it permits the use of the same construct in both plant in vivo assays (using 35S promoter elements) and in the in vitro transcription reactions (using T7 promoter and T7 RNA polymerase). The resulting transcript can be used to program a standard in vitro translation reaction and synthesize proteins in a cell-free system. Since the T7 promoter is downstream of the 35S promoter TATA box, the replacement of the short stretch of the native 35S promoter sequence with the phage sequence does not compromise the activity of the 35S promoter in plant cells.

Figure 11:
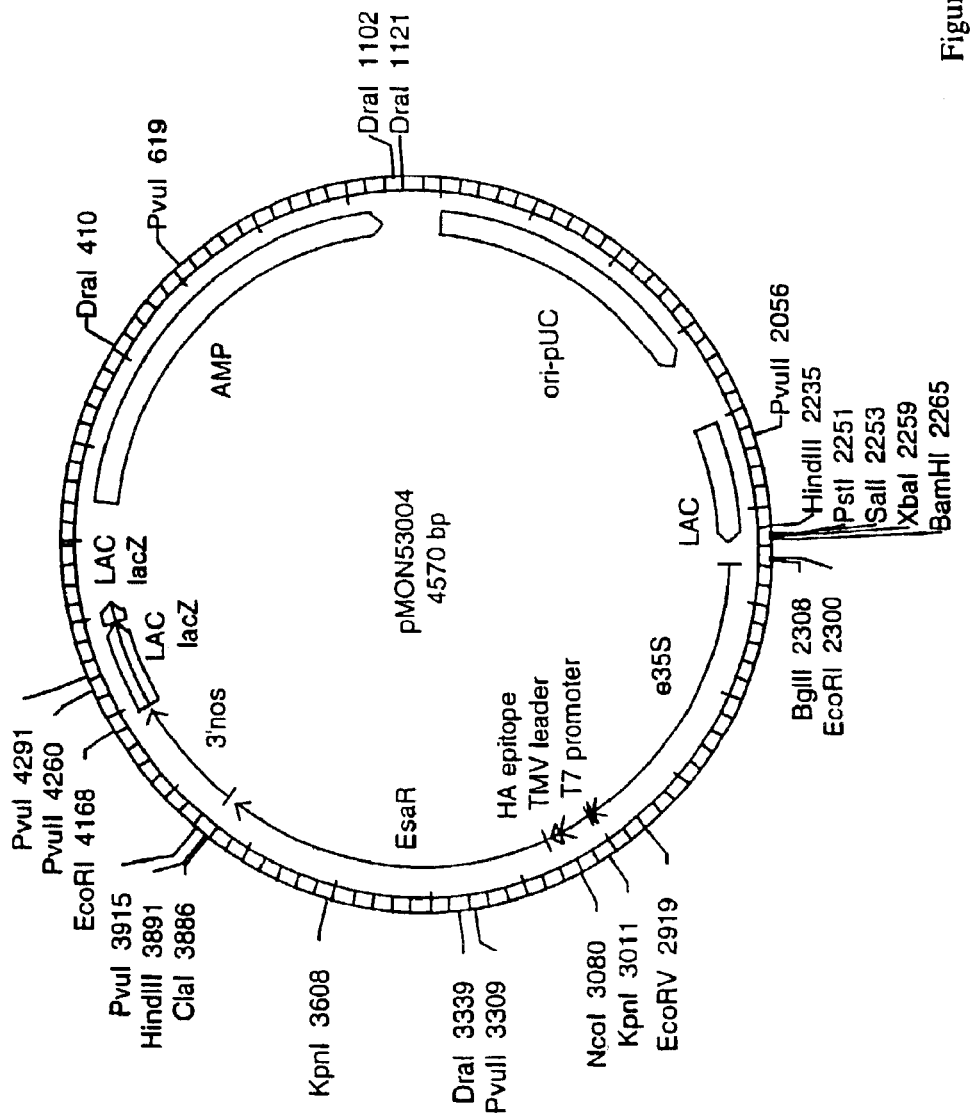
FIG. 11 provides a schematic representation of the expression construct pMON53004.
Figure 12:
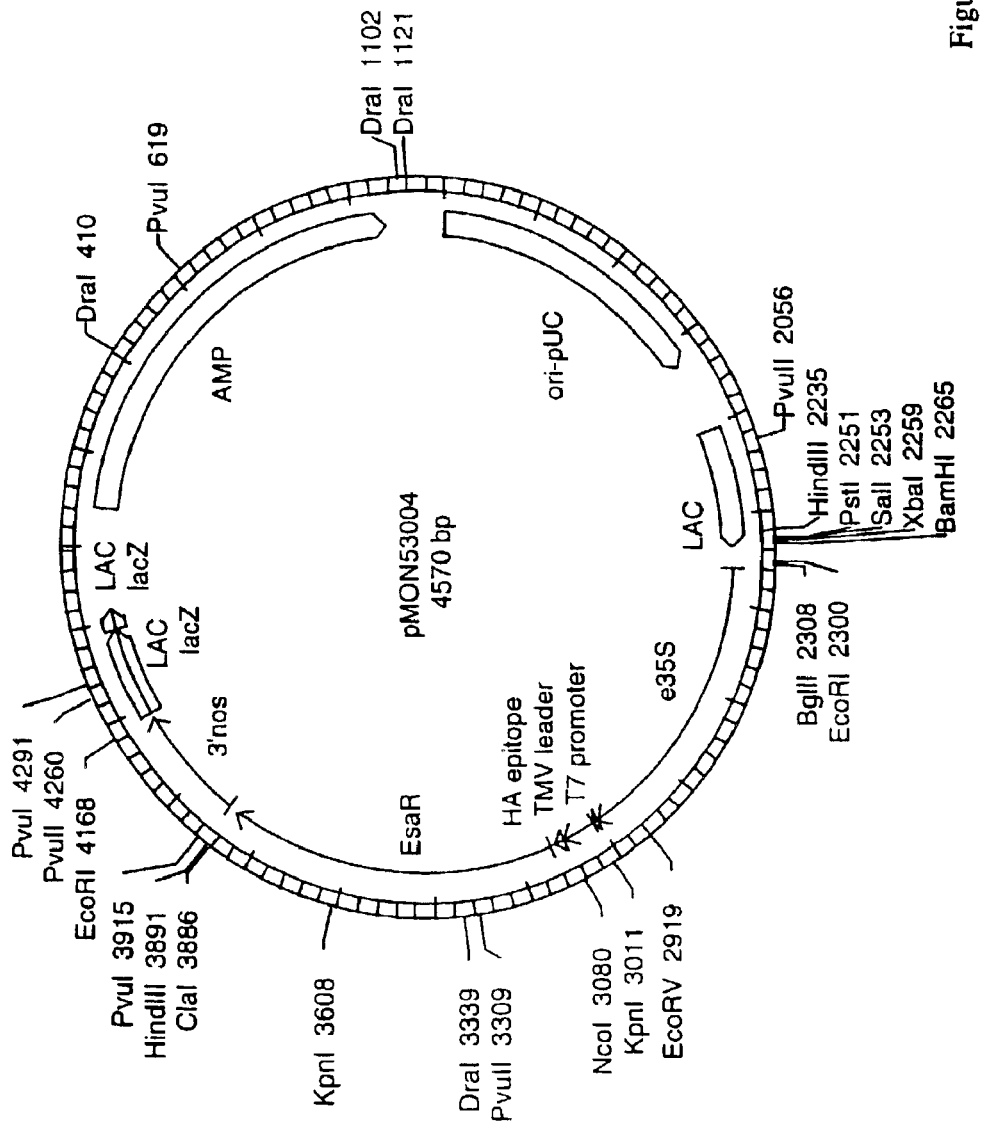
FIG. 12 provides a schematic representation of the expression construct pMON53005.

The examples of the dual-purpose expression construct, pMON53004 and pMON53005, are shown in FIGS. 11 and 12, respectively, for EsaR. The design of CaMV 35S-T7 constructs for other members of the LuxR family is the same except for the EsaR protein coding region.

In order to achieve activation of transcription in the nucleus, a potent activation domain is incorporated in a set of constructs. The source of the activation domain is from the Herpes simplex VP16 gene (amino acids 413–490 of the VP16 protein). This activation domain has been shown to function very efficiently in plants (Ma et al., *Nature* 334:631–633, 1988)

Thus, all effector constructs contain modified CaMV 35S promoter (duplicated enhancer, e35S with nucleotides −17 through −1 replaced by the T7 phage promoter. Promoter is followed by the tobacco mosaic virus (TMV) translational enhancer derived from TMV coat protein (also known as Ω-fragment) followed by NcoI site for cloning. If indicated, it is followed by a synthetic sequence encoding for influenza hemaglutinin (HA) epitope (MGYPYDVPDYAH; SEQ ID NO:46) fused in-frame to either VP16 activation domain or the open reading frame of the AHL receptor protein (also referred to herein as transcriptional regulator protein or element). Transcriptional termination and polyadenylation is provided by the nopaline synthase 3' region (3'NOS).

Figure 9:
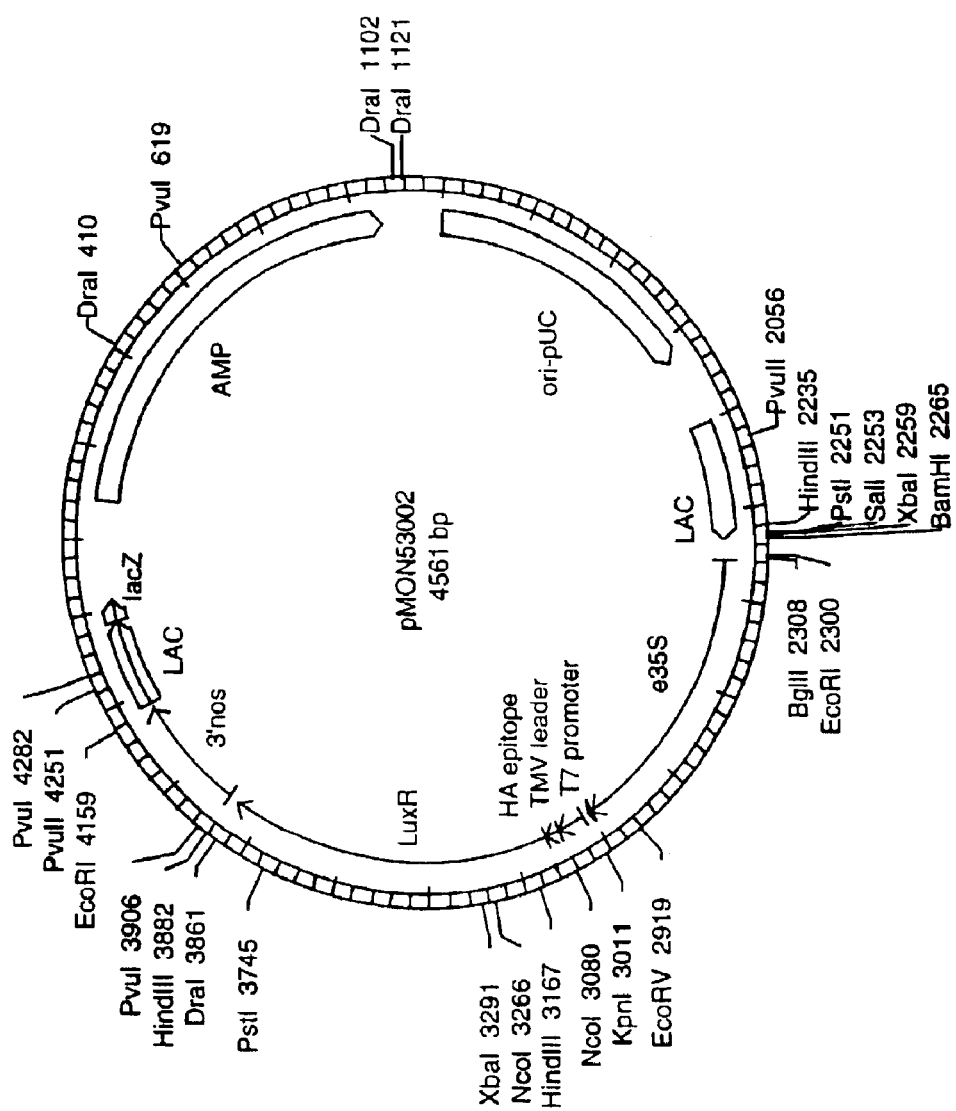
FIG. 9 provides a schematic representation of the expression construct pMON53002.

The construct pMON53002 contains the HA epitope tag operably cloned upstream to the LuxR open reading frame (ORF) fusion under the transcriptional control of a modified enhanced 35S promoter and 3'NOS (FIG. 9).

Figure 10:
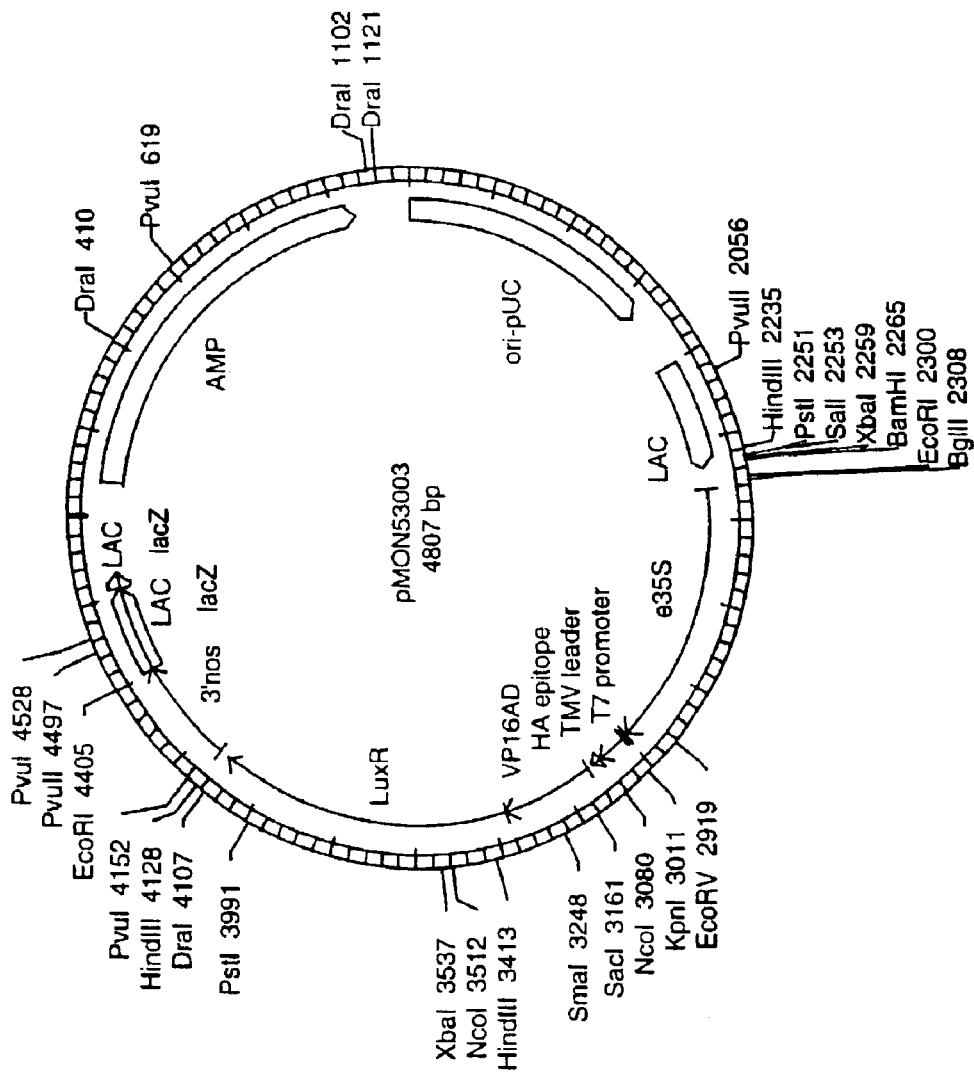
FIG. 10 provides a schematic representation of the expression construct pMON53003.

The construct pMON53003 contains the HA epitope tag operably cloned upstream to the VP16-LuxR open reading frame (ORF) fusion under the transcriptional control of a modified enhanced 35S promoter and 3'NOS (FIG. 10).

The construct pMON53004 contains the HA epitope tag operably cloned upstream to the EsaR open reading frame (ORF) fusion under the transcriptional control of a modified enhanced 35S promoter and 3'NOS (FIG. 11).

The construct pMON53005 contains the HA epitope tag operably cloned upstream to the VP16-EsaR open reading frame (ORF) fusion under the transcriptional control of a modified enhanced 35S promoter and 3'NOS (FIG. 12).

Figure 13:
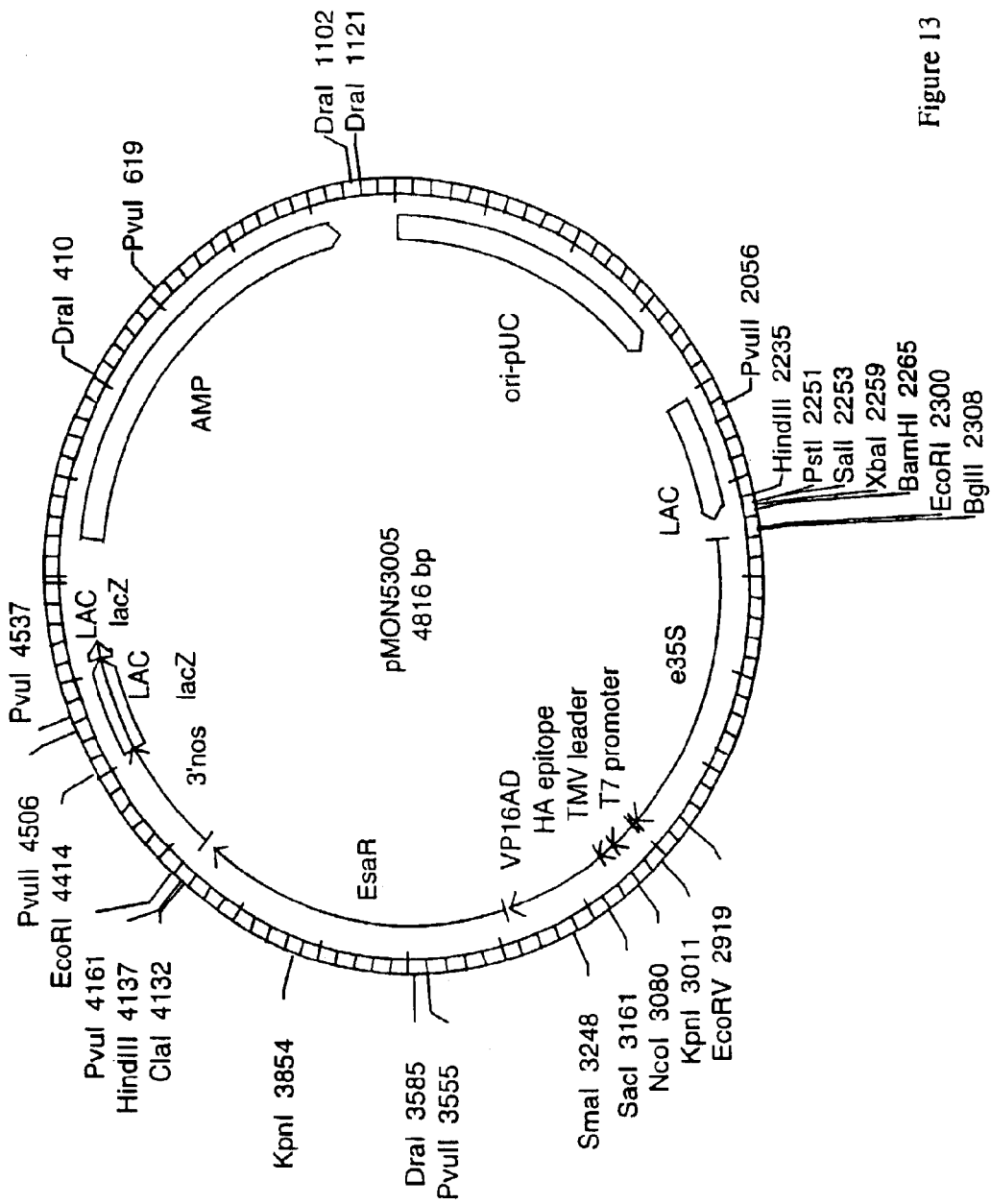
FIG. 13 provides a schematic representation of the expression construct pMON53015.

The construct pMON53015 contains the SV40 nuclear localization signal-VP16-EsaR open reading frame (ORF) fusion under the transcriptional control of a modified enhanced 35S promoter and 3'NOS (FIG. 13).

Figure 14:
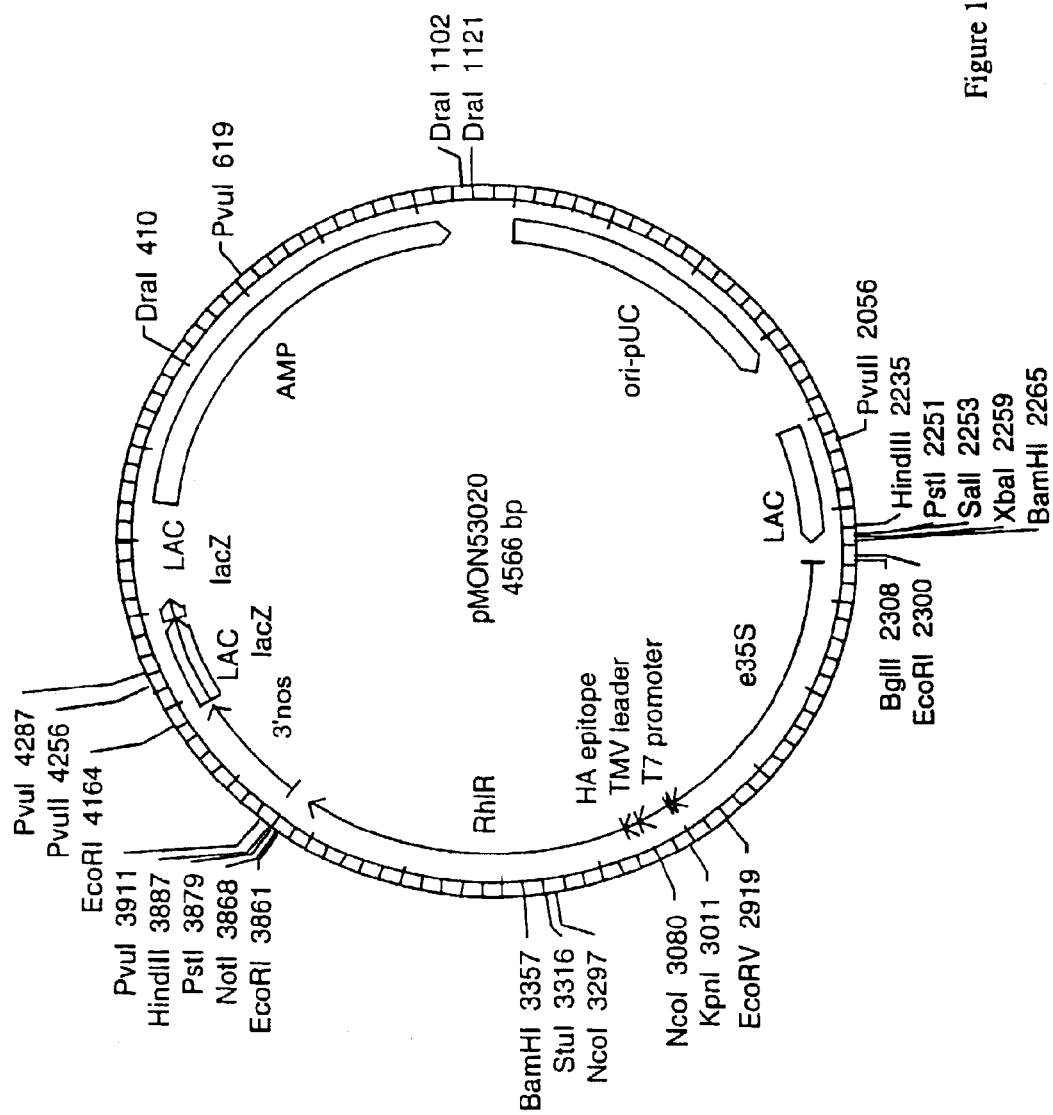
FIG. 14 provides a schematic representation of the expression construct pMON53020.

The construct pMON53020 contains the HA epitope tag operably cloned upstream to the RhlR open reading frame (ORF) fusion under the transcriptional control of a modified enhanced 35S promoter and 3'NOS (FIG. 14).

Figure 15:
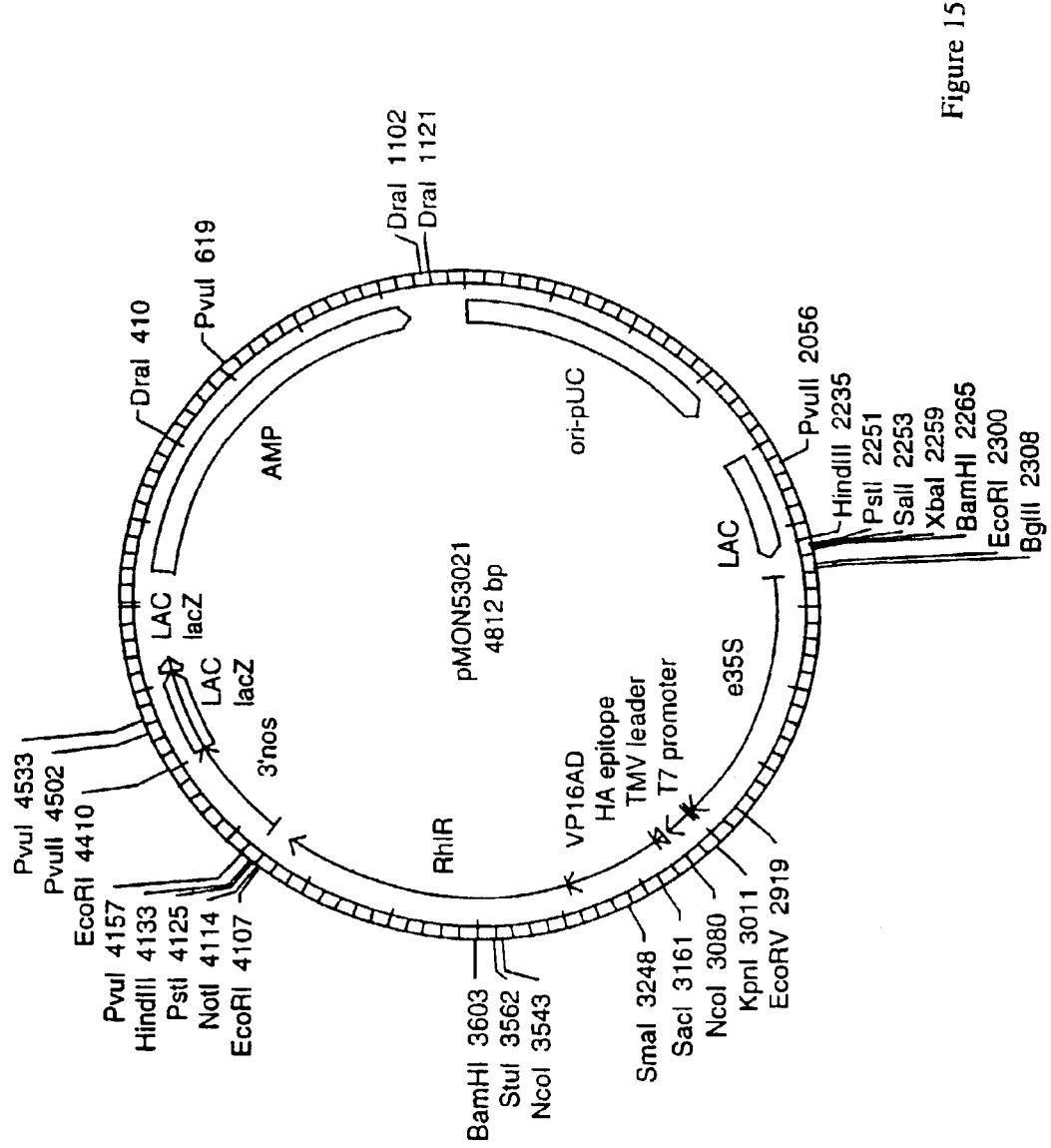
FIG. 15 provides a schematic representation of the expression construct pMON53021.

The construct pMON53021 contains the HA epitope tag operably cloned upstream to the VP16-RhlR open reading frame (ORF) fusion under the transcriptional control of a modified enhanced 35S promoter and 3'NOS (FIG. 15).

Figure 16:
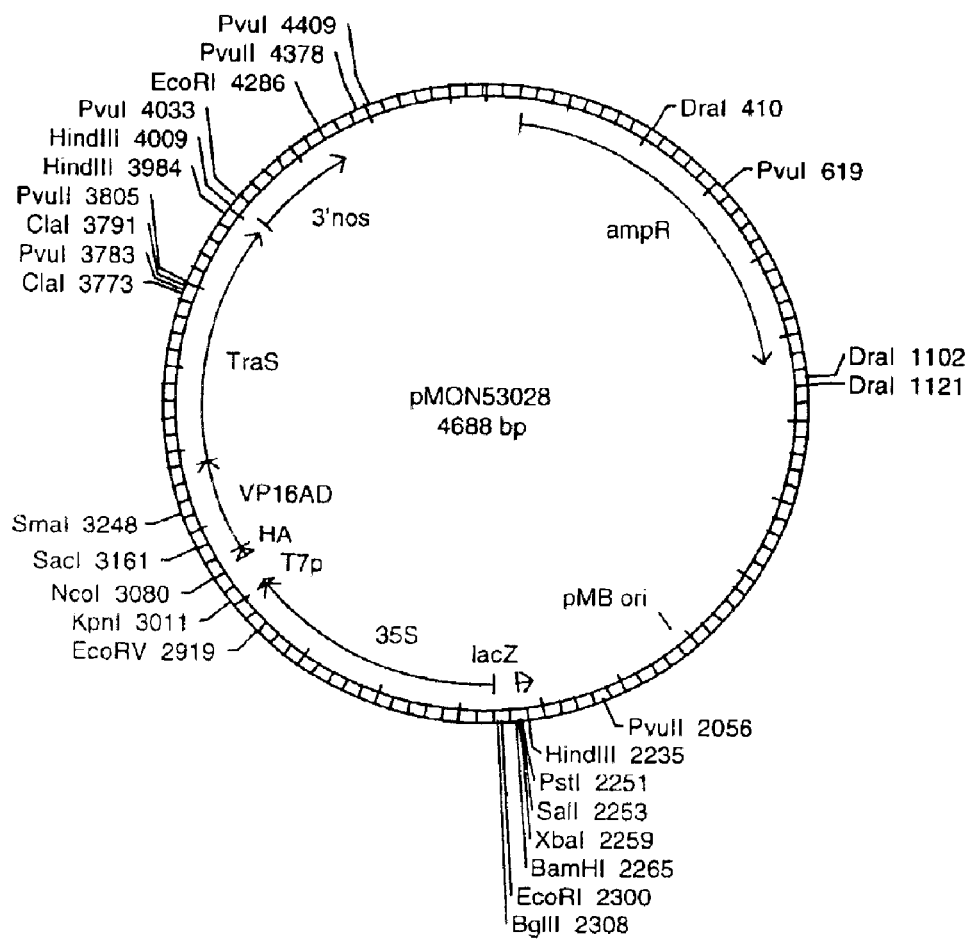
FIG. 16 provides a schematic representation of the expression construct pMON53028.

The construct pMON53028 contains the HA epitope tag operably cloned upstream to the VP16-TraS open reading frame (ORF) fusion under the transcriptional control of a modified enhanced 35S promoter and 3'NOS (FIG. 16).

Figure 17:
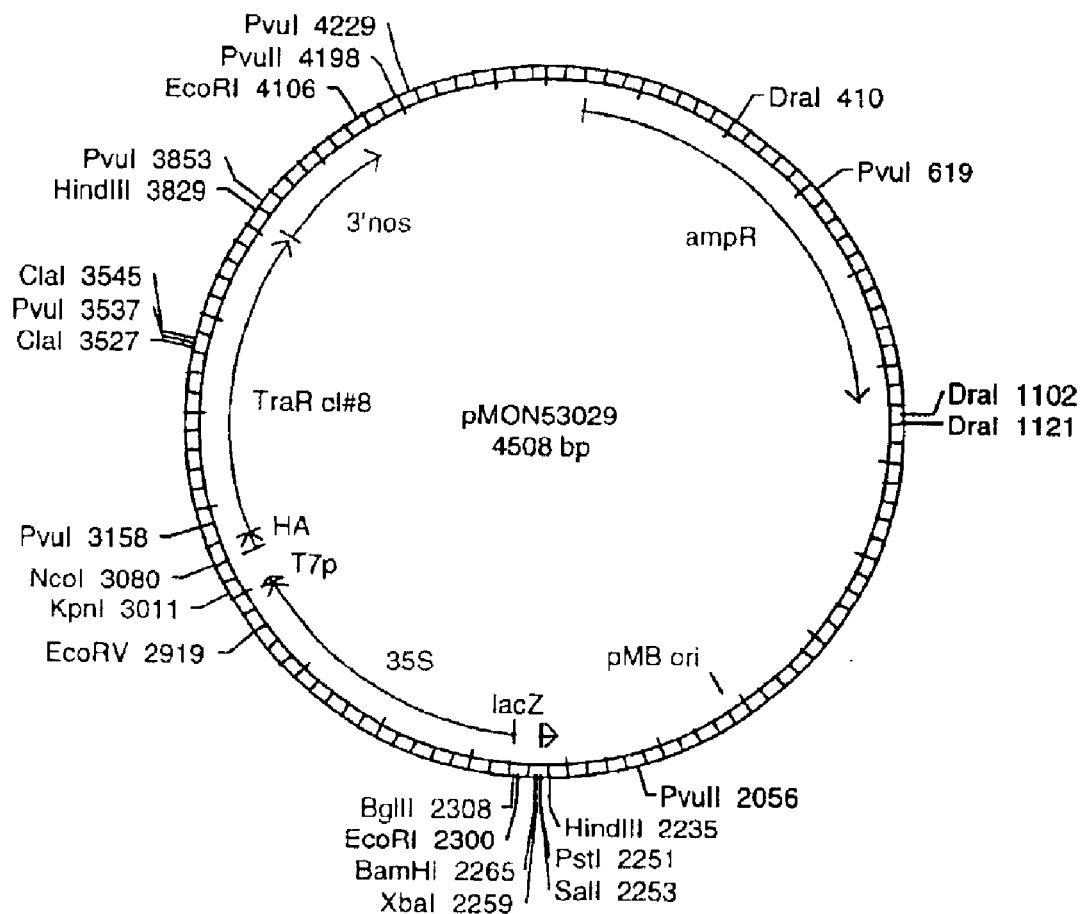
FIG. 17 provides a schematic representation of the expression construct pMON53029.

The construct pMON53029 contains the HA epitope tag operably cloned upstream to the TraR open reading frame (ORF) fusion under the transcriptional control of a modified enhanced 35S promoter and 3'NOS (FIG. 17).

Figure 18:
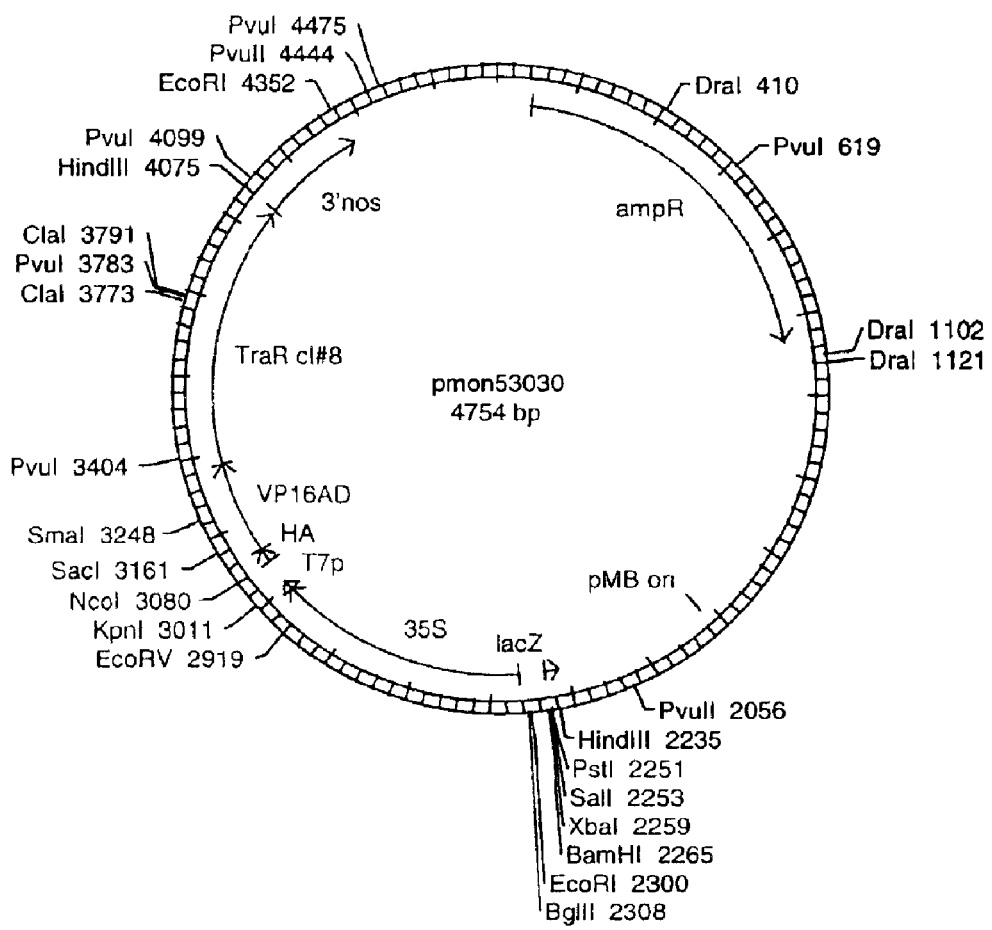
FIG. 18 provides a schematic representation of the expression construct pMON53030.

The construct pMON53030 contains the HA epitope tag operably cloned upstream to the VP16-TraR open reading frame (ORF) fusion under the transcriptional control of a modified enhanced 35S promoter and 3'NOS, thus creating the 35S-HA-VP16-TraR-nos3' expression construct (FIG. 18).

A series of double expression cassette constructs containing both the regulator and the reporter cassettes were prepared for plant transformation.

The construct pMON53071 contains the EsaR regulator fused to the VP16 activation domain under the control of the enhanced 35S promoter in the effector cassette and the iudA gene under the control of the minimal 35S promoter fused with four copies of the esaR cis elements in the reporter cassette.

The construct pMON53072 contains the EsaR regulator fused to the VP16 activation domain under the control of the enhanced 35S promoter in the effector cassette and the luciferase reporter gene under the control of the minimal 35S promoter fused with four copies of the esaR cis elements in the reporter cassette.

The construct pMON53073 contains the TraR regulator fused to the VP16 activation domain under the control of the enhanced 35S promoter in the effector cassette and the iudA reporter gene under the control of the minimal 35S promoter fused with three copies of the traI (see table 2 supra) cis elements in the reporter cassette.

The construct pMON53074 contains the TraR regulator fused to the VP16 activation domain under the control of the enhanced 35S promoter in the effector cassette and the luciferase reporter gene under the control of the minimal 35S promoter fused with three copies of the traI (see table 2 supra) cis elements in the reporter cassette.

The construct pMON53075 contains the TraR regulator fused to the VP16 activation domain under the control of the enhanced 35S promoter in the effector cassette and the iudA reporter gene under the control of the minimal 35S promoter fused with three copies of the traAI (see table 2 supra) cis elements in the reporter cassette.

The construct pMON53076 contains the TraR regulator fused to the VP16 activation domain under the control of the enhanced 35S promoter in the effector cassette and the luciferase reporter gene under the control of the minimal 35S promoter fused with three copies of the traAI (see table 2 supra) cis elements in the reporter cassette.

The construct pMON53077 contains the TraR regulator fused to the VP16 activation domain under the control of the enhanced 35S promoter in the effector cassette and the iudA reporter gene under the control of the minimal 35S promoter fused with three copies of the traA2 (see table 2 supra) cis elements in the reporter cassette.

The construct pMON53078 contains the TraR regulator fused to the VP16 activation domain under the control of the enhanced 35S promoter in the effector cassette and the luciferase reporter gene under the control of the minimal 35S promoter fused with three copies of the traA2 (see table 2 supra) cis elements in the reporter cassette.

The construct pMON53079 contains the TraR regulator fused to the VP16 activation domain under the control of the enhanced 35S promoter in the effector cassette and the iudA reporter gene under the control of the minimal 35S promoter fused with three copies of the traA8 (see table 2 supra) cis elements in the reporter cassette.

The construct pMON53080 contains the TraR regulator fused to the VP16 activation domain under the control of the enhanced 35S promoter in the effector cassette and the luciferase reporter gene under the control of the minimal 35S promoter fused with three copies of the traA8 (see table 2 supra) cis elements in the reporter cassette.

The expression constructs are used to in transformation experiments to obtain transgenic plants. Transgenic *Arabidopsis thaliana* plants can be obtained by *Agrobacterium*-mediated transformation as described by Valverkens et al., (*Proc. Nat. Acad. Sci.* (1988) 85:5536–5540), or as described by Bent et al. ((1994), *Science* 265:1856–1860), or Bechtold et al. ((1993), *C. R. Acad. Sci, Life Sciences* 316:1194–1199). Other plant species can be similarly transformed using related techniques.

2B. Plastid Expression Constructs

A series of constructs are prepared to permit the regulated transcription of nucleic acid sequences of interest in the plant cell plastid. Similar to the nuclear expression constructs described in Example 2A, reporter and effector constructs are prepared; however, the plastid constructs employ regulatory elements for expression in a plant cell plastid.

The Prrn/G10L sequence is constructed by annealing two oligonucleotide sequences, T7lead1 (SEQ ID NO:47) and T7lead2 (SEQ ID NO:48) to create the G10L plastid ribosome binding site.

T7lead1:
5'-AATTGTAGAAATAATTTTGTTTAACTTTAAGAA
GGAGATATACC-3'

T7lead2:
5'-CATGGGTATATCTCCTTCTTAAAGTTAAACAAA
ATTATTTCTAC-3'

The G10L sequence is ligated to the 3' terminus of the Prrn promoter sequence as an EcoRI/NcoI fragment to create the Prrn/G10L sequence.

A series of constructs are prepared that contain various Shine-Delgarno (SD) and downstream box (DB) sequences. PCR is employed using various primer combinations to amplify fragments containing the SD and DB sequences. Reactions using Oligonucleotide primers and plasmid pCGN5063 in pBluescript+(Stratagene) containing the GUS gene under the control of T7 promoter and T7gene10 leader (similar to pCGN4055 described in U.S. Pat. No. 5,576,198) are performed. The T7 promoter and T7gene10 leader is present as a HindIII/NcoI fragment. The primer pairs for each construct were designed to introduce HindIII and NcoI at the respective ends. The resulting PCR fragments are purified, digested with HindIII/NcoI, and ligated to HindIII/NcoI digested pCGN5063 vector backbone. The forward primer carrying the HindIII site is designed to prime at the T7 promoter region and is common for all the constructs (G10L5'
5'-ACGTAAGCTTCGAAATTAATACGACTCACTATA
GGG-3'; SEQ ID NO:49). The reverse primer contains the NcoI site introduced the downstream box and Shine-Dalgarno sequence variants for the various constructs and is listed in Table 3. The downstream box (DB) variants include (a) wildtype gene 10 DB (wt DB) which has 7 bases complementary to the plastidial 16S rRNA(7/15), (b) mutant DB with 15 bases complementary to the plastidial 16S rRNA(m1DB, 15/15), (c) mutant DB with 11 bases complementary to the plastidial 16S rRNA(m2DB, 11/15) and (d) mutant DB with 0 bases (m3DB, 0/15) that potentially can pair with the 15 basepair anti-DB sequence in the tobacco 16S rRNA. The Shine-Dalgarno sequence (SD) variants included wild-type SD AAGGAG (SEQ ID NO:50) (wt SD) and mutant SD UUCCUC (SEQ ID NO:51) (mSD).

TABLE 3

Plastid Expression Constructs

| CONSTRUCT | FEATURES | REVERSE PCR PRIMER |
|---|---|---|
| pCGN6376 | wt SD, wt DB (7/15) | SC123: (SEQ ID NO:52) 5'ACTGCCATGGCCATTTGCTGTC CACCAGTCATGCTAGCCATATGT ATATCTCCTTCTTAAAGTTAAAC |
| pCGN6115 | wt SD, Δ DB | |
| pCGN6377 | m SD, wt DB (7/15) | SC125: (SEQ ID NO:53) 5'ACTGCCATGGCCATTTGCTGTC CACCAGTCATGCTAGCCATATGT ATATGAGGAACTTAAAGTTAAAC AAAATTAT |
| pCGN6365 | wt SD, m1 DB (15/15) | SC126: (SEQ ID NO:54) 5'ACTGCCATGGCCATTTGCAAGG CAGGACTAATGATAGCCATATGT ATATCTCCTTCTTAAAGTTAAAC |

TABLE 3-continued

Plastid Expression Constructs

| CONSTRUCT | FEATURES | REVERSE PCR PRIMER |
|---|---|---|
| pCGN6367 | m SD, m1 DB (15/15) | SC127: (SEQ ID NO:55) 5'ACTGCCATGGCCATTTGCAAGG CAGGACTAATGATAGCCATATGT ATATGAGGAACTTAAAGTTAAAC |
| pCGN6368 | wt SD, m2 DB (11/15) | SC128: (SEQ ID NO:56) 5'ACTGCCATGGCCATTTGCTGTC GGCCTGACCACCTAGCCATATGT ATATCTCCTTCTTAAAGTTAAAC |
| pCGN6369 | wt SD, m3 DB (0/15) | SC129: (SEQ ID NO:57) 5'ACTGCCATGGCCATTTGCTGGG CAGCGGTAGTGCTAGCCATATGT ATATCTCCTTCTTAAAGTTAAAC |

Chimeric genes encoding regulator proteins are preferably inserted into the expression vector to direct their transcription from the Prrn promoter. Thus, in the plastid genome, chimeric genes encoding regulator proteins are transcribed from the Prrn/RBS promoter, or the Prrn/G10L promoter in the plant plastid.

A series of constructs are prepared to direct the expression of the GUS gene from a promoter containing lux box sequences (reporter constructs) as well as constructs for the expression of the regulatory protein from the Prrn/RBS and Prrn/G10L promoter sequences.

Figure 19:
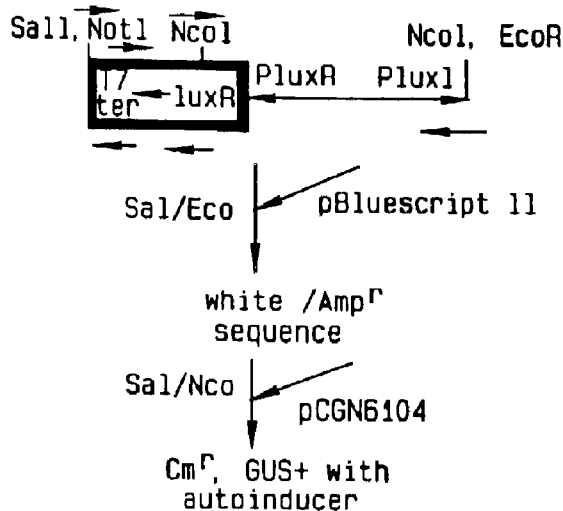
FIG. 19 provides a schematic for the preparation of the construct providing for the expression of the GUS encoding sequence from the luxI promoter and regulated by the LuxR transcriptional activator expressed under the control of the native luxR promoter.
Figure 19:
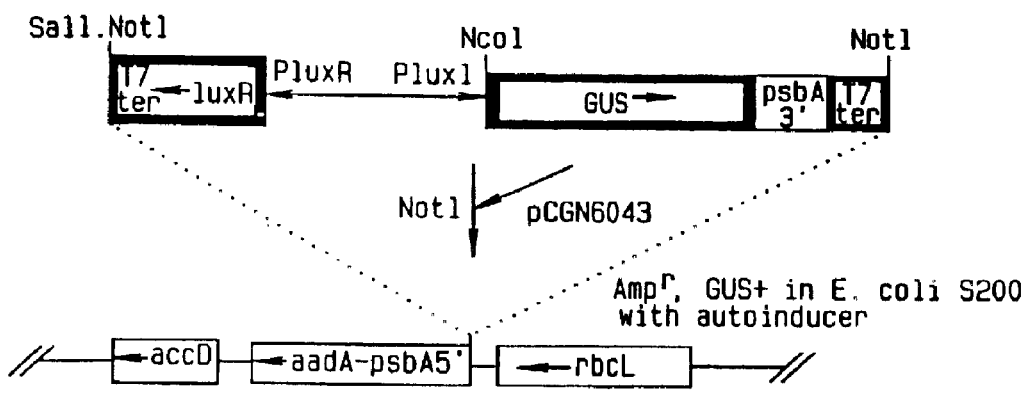

The luxR coding region and upstream sequences are amplified using polymerase chain reactions (PCR) and cloned 5' of the GUS coding sequence. A three step PCR reaction is used to amplify the luxI promoter/luxR promoter/luxR coding sequence to remove the luxR coding sequence NcoI site. An opposing oriented T7 terminator sequence is added 5' of the luxR coding sequence to prevent read through transcription and spurious activation of GUS gene expression. In addition, a SalI/NotI site is added to the 5' terminus of the terminator and an NcoI site is added at the start codon of the LuxI promoter along with an EcoRI site for cloning purposes. This fragment is cloned into pBluescript II and sequenced to confirm that the sequence amplified is correct. The luxI promoter/luxR promoter/luxR coding sequence/T7 terminator fragment is subcloned into pCGN6104 as a SalI/NcoI fragment. This vector creates the inducible expression system for the inducer regulated expression of GUS from the luxI promoter (FIG. 19). The NotI fragment from this plasmid is cloned into tobacco plastid homology vector pCGN6043 to provide for the expression of the GUS sequence under control of the luxI promoter and luxR protein. The resulting construct contains sequences for integration into the rbcL region via homologous recombination (Svab et al., *Proc. Natl. Acad. Sci. USA* 90:913–917, 1993).

Figure 20:
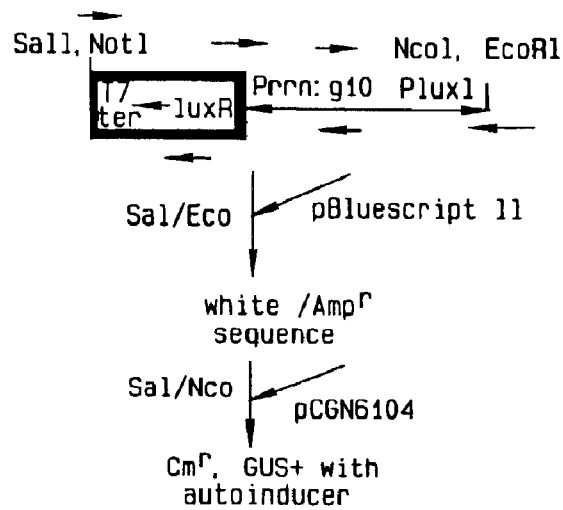
FIG. 20 provides a schematic for the preparation of the construct providing for the expression of the GUS encoding sequence from the luxI promoter and regulated by the LuxR transcriptional activator expressed under control of the Prrn/G10L promoter/leader sequences.
Figure 20:
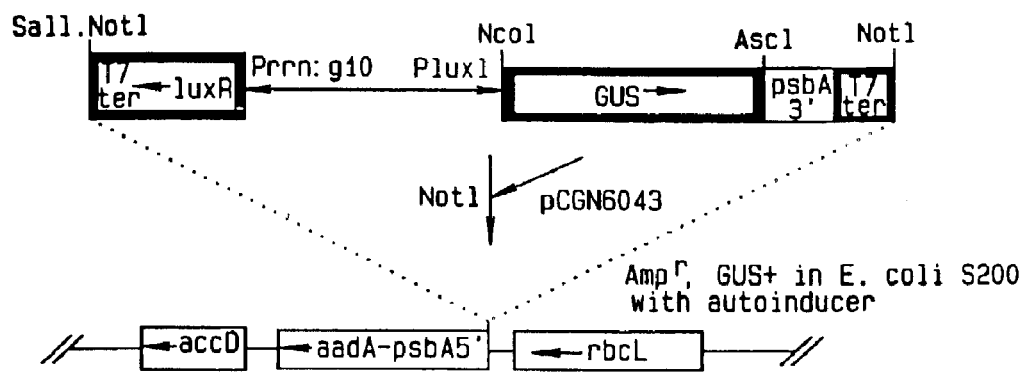

A second transformation construct for the expression of the GUS gene from the plant plastid is constructed. This construct contains the GUS coding sequence operably linked to the luxI promoter, as described above, and the luxR coding sequence under the control of the Prrn/G10L promoter/ribosome binding site. This construct also contains sequence to provide for the integration of the expression cassette into the chloroplast genome in the rbcL region (Svab et al. (1993), supra). The inclusion of the Prrn:G10L promoter/RBS in this expression construct provides for the high level expression of the inactive form of the luxR protein in plant cell plastids (FIG. 20).

Figure 21:
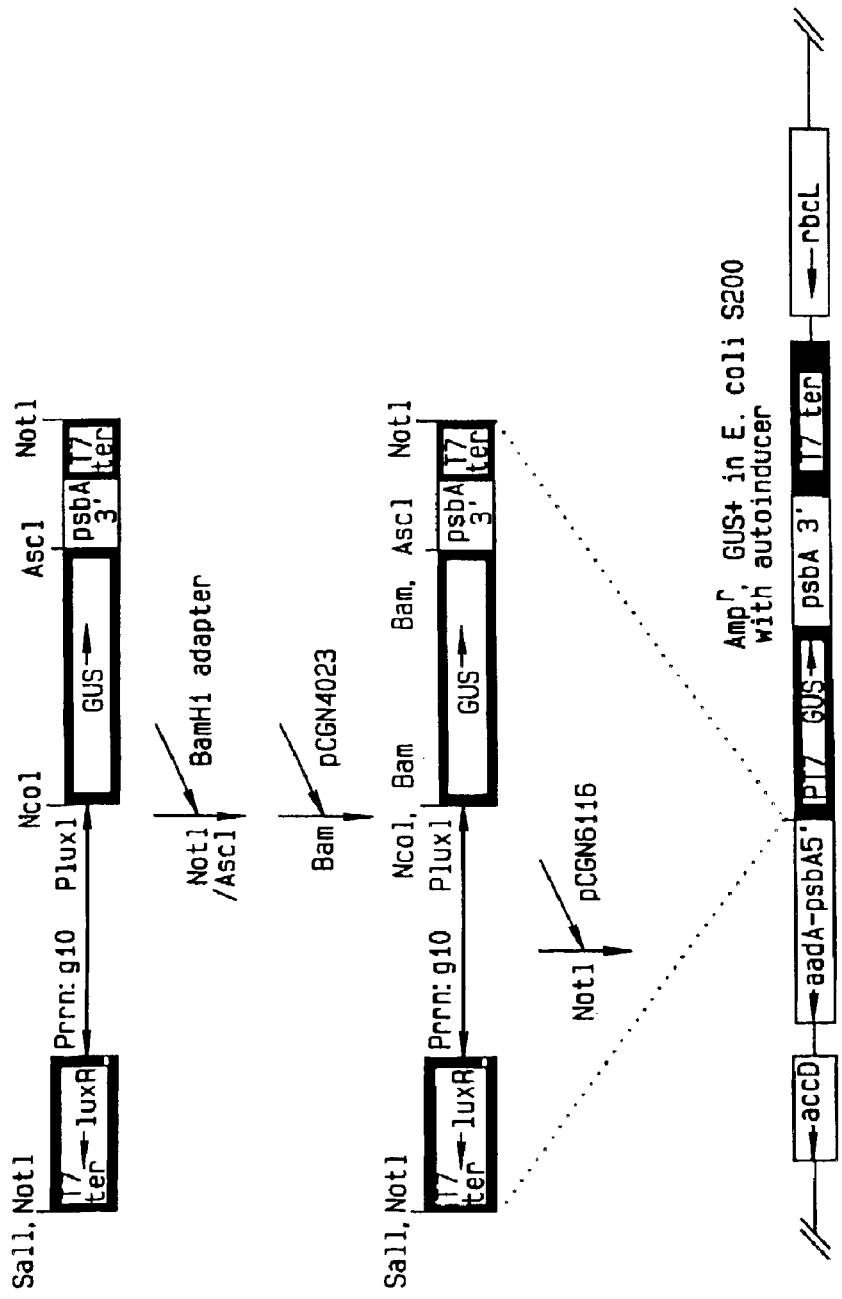
FIG. 21 provides a schematic for the preparation of the construct providing for the expression of the GUS encoding sequence from the viral T7 promoter. The T7 RNA polymerase controlling the expression from the T7 promoter is expressed from the luxI promoter and regulated by the LuxR transcriptional activator expressed under the control of the Prrn/G10L promoter/leader sequences.

A third expression cassette is prepared to test the ability of the system for controlling the T7 RNA polymerase and downstream target genes all from within the plastid. In this cassette, the luxR coding sequence is driven by the Prrn/G10L sequence (described above), which controls the expression of the T7 RNA polymerase under the control of the LuxI sequence. The GUS gene is in turn controlled by the T7 promoter. The Prrn/G10L:luxR/LuxI:T7 RNA Polymerase/T7/GUS cassette (FIG. 21) is cloned into the T7:GUS/rbcL homology cassette, pCGN6116.

Two expression constructs are prepared to test the esaR repression system for expressing DNA sequences of interest from the plant plastid.

Figure 22:
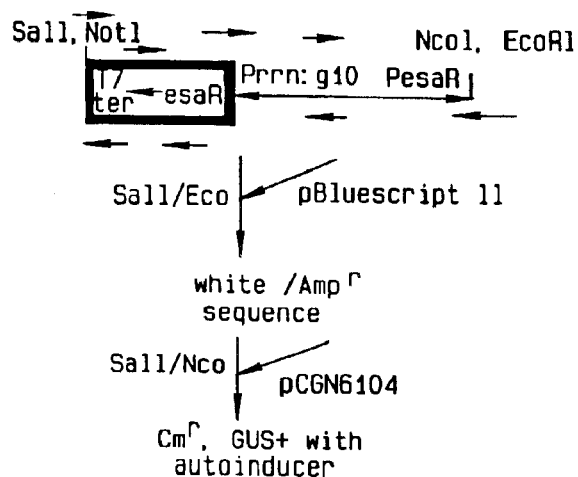
FIG. 22 provides a schematic for the preparation of the construct providing for the expression of the GUS encoding sequence from the esaR promoter and regulated by the EsaR transcriptional repressor expressed under the control of the Prrn/G10L promoter/leader sequences.
Figure 22:
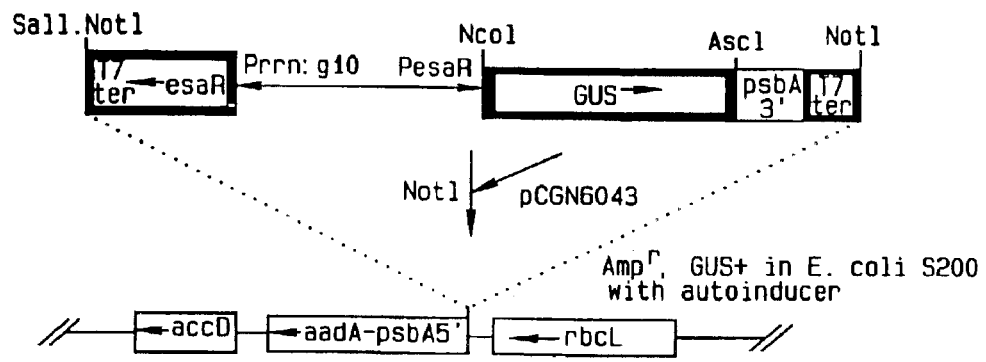

The esaR coding region is PCR amplified and ligated to the T7 polymerase terminator sequence and the Prrn:G10L. The esaR promoter sequence is cloned in a divergent expression orientation of the Prrn:G10L/esaR coding sequence/T7 terminator. A fragment containing the GUS coding sequence with the psbA 3' and T7 polymerase terminator are cloned so as to be transcribed from the esaR promoter sequence. The resulting fragment containing two divergently expressed cassettes, Prrn:G10L/esaR/T7 terminator and esaR/GUS/psbA 3'/T7 terminator (FIG. 22), are cloned into a vector to allow for the integration of the expression cassettes as well as containing sequences for the selection of transplastomic plants using spectinomycin (psbA 3'/aadA).

Figure 23:
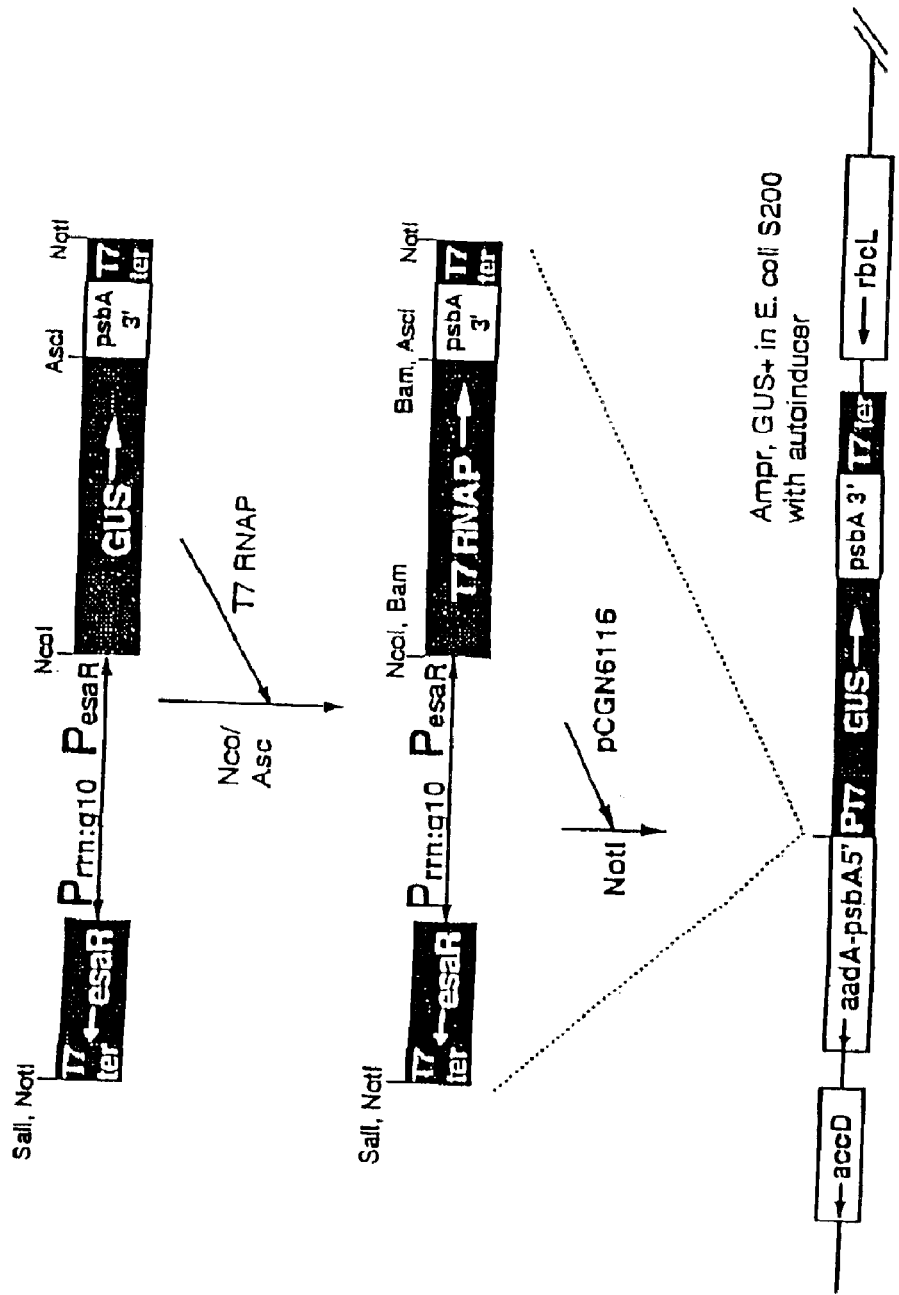
FIG. 23 provides a schematic for the preparation of the construct providing for the expression of the β-glucuronidase (GUS) encoding sequence from the viral T7 promoter. The T7 RNA polymerase controlling the expression from the T7 promoter is expressed from the esaR promoter and regulated by the EsaR transcriptional repressor expressed under the control of the Prrn/G10L promoter/leader sequences.
Figure 24:
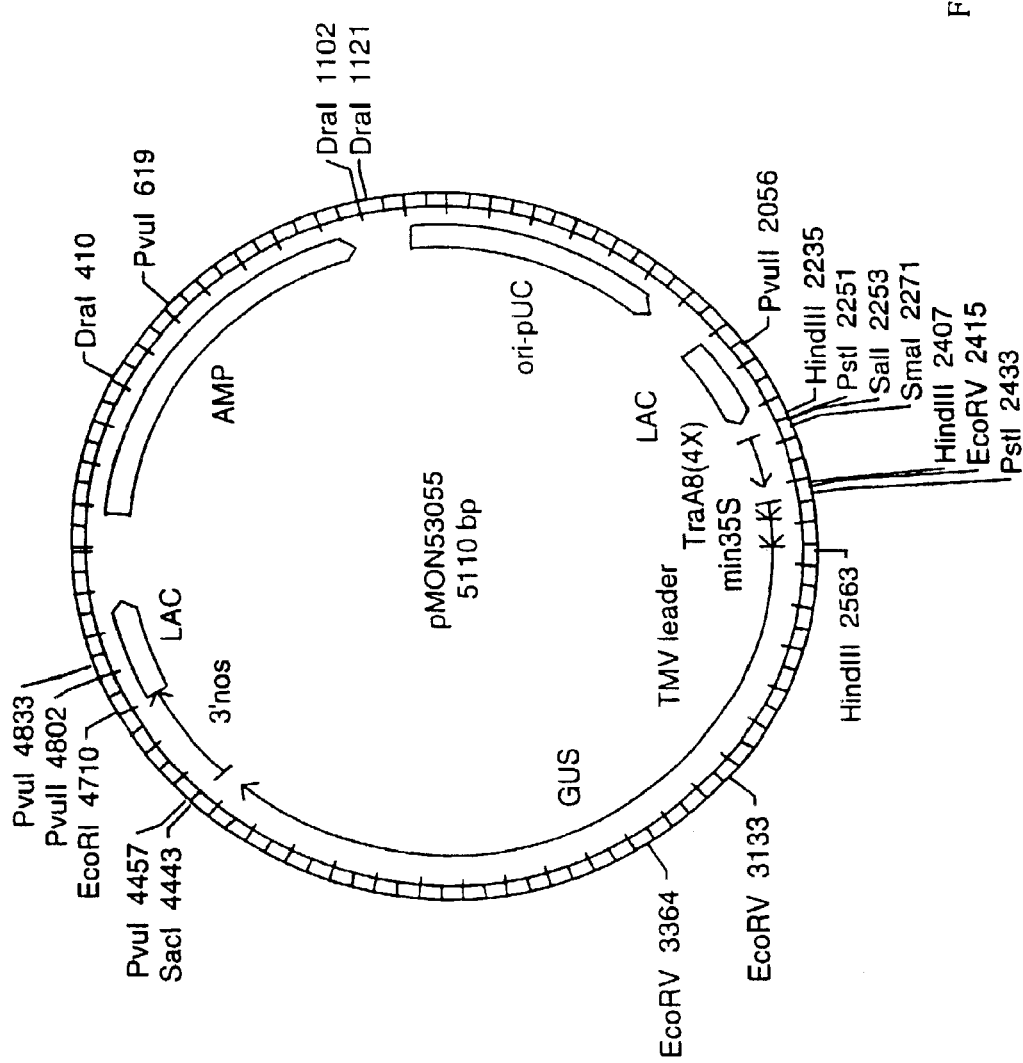
FIG. 24 provides a schematic representation of the expression construct pMON53055.

A plant expression vector is prepared to express the T7 RNA polymerase from the esaR promoter. The T7 RNA polymerase coding sequence is cloned to be expressed from the esaR promoter as described for the expression of the GUS coding sequence above. A fragment containing divergent transcription cassettes, Prrn:G10L/esaR/rps16 3'/T7 terminator (complementary strand) and PesaR/T7 RNA polymerase/psbA 3'/T7 terminator, is cloned as a NotI fragment into a vector containing elements for the integration of the expression sequences into the plastid genome. The vector also contains a GUS coding sequence expressed from a T7 polymerase promoter, and sequences for the expression of the aadA marker gene. This construct (FIG. 23) allows for inducer controlled expression of T7 RNA polymerase further regulating the expression of the GUS coding sequence from the T7 promoter.

Example 3

Induction of GUS Expression in E. coli

The nuclear constructs described in example 2A above are transformed in E. coli strain S10200. Positive transformed colonies, which are ampicillin resistant, are grown in medium cultures either lacking the AHL inducer or containing AHL. Cultured colonies are screened for the production of GUS by assaying cell lysate preparations for GUS enzyme activity to confirm inducer controlled expression. GUS assays are conducted as described by Jefferson et al. (*EMBO J.* 6:3901–3907, 1987).

Example 4

Plant Transformation

4A. Transfection into Plant Cells

Plasmids for transfection were isolated and purified using Megaprep plasmid DNA isolation kit (Qiagen). Carrot protoplasts for transfections were prepared from carrot cell suspension culture and transfected with purified DNA as described (Ulmasov et al., *Plant Cell* 7:1611–1623, 1995). Briefly, 10 μg of the reporter plasmid and 5 μg of the effector plasmid were incubated with $10^6$ protoplasts for five minutes at the room temperature in the presence of polyethylene glycol-calcium solution. After diluting approximately 10-fold with the culture medium, the protoplasts were incubated in the dark for 36 hours either in the presence or absence of the inducer 3-oxohexanoyl-homoserine lactone (OHHL, racemic mixture of the L- and D-isomers, purchased from Sigma Chemical Co., St Louis, Mo.). After incubation, protoplasts were collected by low-speed centrifugation, lysed and the level of GUS activity was measured using fluorometric GUS assay (Jefferson et al., *EMBO J.* 6:3901–3907, 1987). Every DNA/AHL combination was done in triplicates and the averages of the GUS activities were adjusted by subtracting the background from the "no DNA" transfection control.

4B. Plastid Transformation

Stable transformation of tobacco plastid genomes by particle bombardment is reported in Svab et. al. (1990, supra) and Svab et al. (1993, supra). The methods described therein may be employed to obtain plants transformed with the plastid expression constructs described herein. Such methods generally involve DNA bombardment of a target host explant, preferably an explant made from a tissue which is rich in metabolically active plastids, such as green plant tissues including leaves or cotyledons.

Tobacco seeds (*N. tabacum* v. *Xanthi* N/C) are surface sterilized in a 50% chlorox solution (2.5% sodium hypochlorite) for 20 minutes and rinsed 4 times in sterile $H_2O$. These are plated aseptically on a 0.2×MS salts media and allowed to germinate. The seedlings are grown on agar solidified MS media with 30 g/l sucrose (Murashige et al., *Physiol. Plant* 15:493–497, 1962).

Tungsten (1.0 μM) or gold microprojectiles (0.6 μM) are coated with plasmid DNA according to Maliga (*Methods in Plant Molecular Biology—A Laboratory Manual*, eds. Maliga et al., Cold Spring Harbor Press, 1993) and used to bombard mature leaves, placed abaxial side up on RMOP media; MS salts, 1 mg/l BAP, 0.1 mg/l NAA, 30 g/l sucrose and 0.7% phytagar (Svab et al., *Proc. Natl. Acad. Sci. USA* 87:8526–8530, 1990) using the Bio-Rad PDS 1000 He system (Sanford et al., *Technique* 3:3–16). Plasmids pZS223 and pZS224 are used as the coating plasmid DNA.

The bombarded tissue is then cultured for approximately 2 days on a cell division-promoting media, after which the plant tissue is transferred to a selective media containing an inhibitory amount of the particular selective agent. Transformed explants form green shoots in approximately 3–8 weeks. Leaves from these shoots are then subcultured on the same selective media to ensure production and selection of homoplasmic shoots.

Example 5

Analysis of Transgenic Plants

5A. Transfection Analysis

When the esaR box (4X)-GUS reporter construct, pMON53009, was transfected into carrot protoplasts along with the 35S-CAT ("neutral" effector construct to compensate for the total amount of DNA in the reaction), the GUS activity appeared to be about 34 fold higher than that of the minimal promoter. This is likely a result of a weak activation by endogenous transcription factors binding to multimerized esaR-box elements with low affinity. It is common to see higher background with cis-element multimers, as multimerization often promotes synergistic binding of transcription factors. It is also possible that the background is caused by cryptic plant cis-elements embedded into the esaR box or the 10 bp spacer region, which separates one esaR box from another. When the construct encoding for VP16-EsaR fusion (pMON53005) was used in the transfection experiment, the level of reporter gene expression was significantly (about 40–50 fold) higher than the expression level of the minimal promoter construct. This potent activation by the VP16-EsaR construct was diminished up to 3.3-fold by the addition of the inducer, (3-oxohexanoyl-L-homoserine lactone) in a dose-dependent manner.

This result indicates that the VP16-EsaR fusion protein is likely to bind to the cis-elements autonomously, in the absence of bacterial RNA polymerase, and that this binding can be reversed by its ligand, AHL. This result is also consistent with the hypothesis that, unlike some other members of the LuxR family, EsaR functions as a repressor, not the activator in bacterial cells. This mode of action was proposed by others based on the data from genetic experiments (von Bodman and Farrand, *J. Bacteriol.*, 177:5000–5008, 1995; von Bodman et al., *Proc. Natl. Acad USA* 95:7687–7692, 1998). The fact that EsaR-dependent transcription can be regulated in plant cells by low concentrations of its natural ligand suggests that this AHL compound is able to penetrate plant cell membranes and is stable enough to achieve its effect during the 36 hour experimental time period.

The activation by the VP16-EsaR construct was specifically restricted to esaR box-containing reporter construct. When it was used in combination with other reporters, GAL4(4X) (four copies of the GAL4 site) upstream of the minimal 35S promoter, or seven copies of the luxI box, no activation was observed, indicating that esaR DNA-binding domain does not recognize either unrelated (GAL4), or even closely related (luxI) sites with affinity sufficient enough to provide detectable activation.

Expression of the iudA gene from the traII box (pMON53031) using the TraR regulator (pMON53030) is also determined as described for the EsaR constructs above. The results are shown below in Table 4.

Ten µg of the reporter plasmid (pMON53031), and indicated amount of the 35S effector plasmid per reaction was used for transfection in triplicate. After transfection, protoplasts were incubated in the dark for 36 hrs either in the absence or presence of the 3-oxooctanoyl-L-homoserine lactone (OOHL). The "– inducer" and "+ inducer" columns are averages of the GUS activities.

TABLE 4

Induction of Expression of the iudA gene from the traI1 Box Using TraR

| Construct | – inducer | + inducer | [µM OOHL] | Fold induction |
|---|---|---|---|---|
| min35S-GUS | 7.9 | 6.1 | 25 | 0.8 |
| pMON53031 | 276.3 | 265 | 25 | 1 |
| pMON53030 (60 µg) | 318.3 | 1446.4 | 100 | 4.5 |
| pMON53030 (60 µg) | 350.2 | 1595.5 | 50 | 4.6 |
| pMON53030 (60 µg) | 281.7 | 1393.2 | 25 | 4.9 |
| pMON53030 (60 µg) | 291.3 | 1526.2 | 12.5 | 5.2 |
| pMON53030 (60 µg) | 284.1 | 1474.2 | 5 | 5.2 |
| pMON53030 (60 µg) | 384.6 | 1487.8 | 2.5 | 3.9 |
| pMON53030 (60 µg) | 178.7 | 458.2 | 1 | 2.6 |
| pMON53030 (60 µg) | 280.7 | 698 | 0.5 | 2.5 |
| pMON53030 (60 µg) | 264.9 | 355.9 | 0.1 | 1.3 |
| pMON53030 (60 µg) | 347.7 | 568.5 | 25 (C6) | 1.6 |
| pMON53030 (30 µg) + CAT | 186.5 | 215.7 | 25 | 1.2 |
| pMON53005 (60 µg) | 209.7 | 764.1 | 25 | 3.6 |
| pMON53035 + pMON53005 (60 µg) | 3.5 | 4.9 | 25 | 1.4 |

The results of the above plant cell assays demonstrates that at least a 5.2 fold induction of GUS using activation or repression constructs can be obtained using the methods of the present invention. Also, the reporter constructs showed up to 40-fold higher background when compared the minimal promoter, suggesting that the background was due to endogenous factors recognizing and binding to the tra-box elements. Finally, induction did not appear to occur in the absence of the inducer.

5B. Transplastomic Plant Analysis

Plastid transformed plants selected for aadA marker gene expression were analyzed to determine whether the entire plastid content of the plant has been transformed (homoplasmic transformants). Typically, following two rounds of shoot formation and spectinomycin selection, approximately 50% of the transgenic plantlets that were analyzed are homoplasmic as determined by Southern blot analysis of plastid DNA. Homoplasmic plantlets were selected for further cultivation.

Southern blot analysis was used to confirm the integration of the chimeric expression cassettes in the plastid genome. Preparation, electrophoresis, and transfer of DNA to filters was as described (Svab et al., 1993, supra)). Total plant cellular DNA was prepared as described by Dellaporta et al., *Plant Mol. Biol. Rep.* 1:19–21, 1983).

To measure AHL dependent transcription of the GUS gene, total cellular RNA samples from leaf tissue, treated or untreated with AHL, was subjected to Northern analysis with a GUS specific probe. Total plant RNA was prepared as described by Hughes et al. (*Plant Mol. Biol. Rep.* 6:253–257, 1988), or by using TRIzol Reagent (BRL Life Technologies, Gaithersburg, Md.) following the manufacturers protocol. A single abundant mRNA band of the expected size (2.1 kb) was present only in the RNA samples extracted from leaf tissue treated with AHL. This indicates that transcription of the GUS transgene is dependent on the application of AHL.

To demonstrate that the T7 GUS transcripts are translated in the transgenic plastids, B-glucuronidase specific activity was measured in various tissues. GUS assays were conducted as described by Jefferson et al. (*EMBO J.* 6:3901–3907, 1987).

5C. Transgenic *Arabidopsis* Analysis

Transgenic *Arabidopsis* plants containing TraA8(3X)-GUS reporter and 35S-VP16-TraR activator genes (pMON53077) were analyzed for induction of GUS activity. Eight plants demonstrated GUS activity in the presence of C8-HSL. Three of those eight demonstrated strong activation with very low levels of background activity. However, it was difficult to accurately determine fold induction because of the extremely low uninduced activity, but a preliminary estimate suggests that it is not less than a 75 to 150-fold induction. GUS assays were conducted as described by Jefferson et al. (supra).

| Plant | – Inducer | + Inducer | Fold Induction |
|---|---|---|---|
| wild-type | 105.22 | 2.48 | |
| s3553-1 | 22.37 | 556.56 | 24.88 |
| s3553-2 | 19.89 | 554.08 | 27.85 |
| s3554-1 | 158.17 | 3101.09 | 19.6 |
| s3554-2 | 155.69 | 3098.61 | 19.90 |
| s3559-1 | 5.13 | 599.93 | 116.94 |
| s3559-2 | 2.65 | 597.45 | 225.81 |
| s3562-1 | 0.61 | 75.93 | 124.48 |
| s3562-2 | 0.01 | 73.45 | 7344.96 |
| s3570-1 | 3461.84 | 4831.21 | 1.40 |
| s3570-2 | 3459.36 | 4828.73 | 1.4 |
| s3573-1 | 387.13 | 768.65 | 1.99 |
| s3573-2 | 384.65 | 766.17 | 1.99 |
| s3575-1 | 29.05 | 3453.00 | 118.86 |
| s3575-2 | 26.57 | 3450.52 | 129.89 |
| s3582-1 | 2.02 | 559.86 | 277.16 |
| s3582-2 | 0.01 | 557.38 | 55738.11 |

-continued

| Plant | − Inducer | + Inducer | Fold Induction |
|---|---|---|---|
| s3594-1 | 7.32 | 515.77 | 70.46 |
| s3594-2 | 4.84 | 513.29 | 106.02 |

Figure 25:
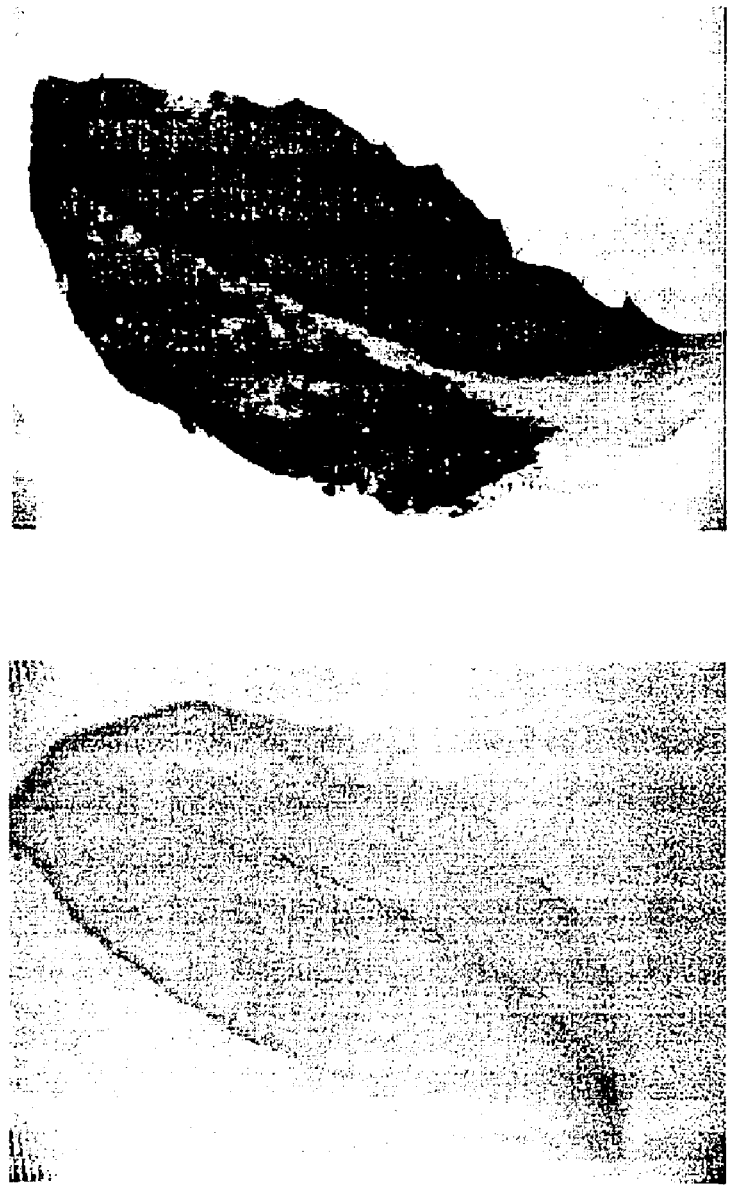
FIG. 25 provides the results of results of histochemical GUS staining of induced (treated with HSL) and uninduced of transgenic *Arabidopsis* plants containing the TraA8(3x)-GUS reporter and 35S-VP16-TraR activator genes (pMON53077).

In addition, detached leaves incubated for 24 hours in MS medium with or without 100 µM HSL were visualized for induction of GUS activity after staining. Caulline leaves treated with the inducer for 24 hours displayed uniform induced activity as revealed by histochemical GUS staining. Results of histochemical staining are provided in FIG. 25.

Example 6

Mutated tra Box Sequences Reduce Background Expression in Carrot Cells

In order to increase levels of inducibity of TraR system in carrot cells it was necessary to decrease levels of background activity of the tra box-GUS reporter gene. This gene, which contains three copies of the traII box upstream of the minimal 35S promoter, demonstrated quite high activity 10- to 50-fold greater activity than the minimal 35S promoter, even without VP16-TraR effector. This background activity is apparently a result of activation by an endogenous transcription factor that binds to a cryptic sequence(s) in the tra box and activates transcription independently of TraR. As no TraR or homologs thereof have been reported to date in plants, it is unlikely that the DNA-binding specificity of the endogenous factor is identical to that of TraR.

Starting with the hypothesis that not every nucleotide in the tra box is critically important for binding, we attempted to change the tra box sequence in a way that it will still be recognized by TraR, but not by the endogenous plant factor. Ten double stranded oligonucleotides containing one or two base alterations of the traA box, a naturally occuring perfectly palindromic traR binding site, were designed, as shown in Table 2 (traA1 to traA9 and traA-1). In traA variants traA1 to 9, two base pair changes were symmetrically arranged as shown in Table 2 (with changed bases in lower case).

The wild-type and variant tra boxes were cloned in multiple copies upstream of the 35S minimal promoter. The resulting plasmids are as follows (see Table 2 above for the sequence of the tra boxes used).

pMON53041: traA1-box (3X)-46GUS, cl.35 pMON53042: traA2-box (3X)-46GUS, cl.43 pMON53043: traA3-box (3X)-46GUS, cl.4 pMON53044: traA4-box (3X)-46GUS, cl.23 pMON53045: traA5-box (3X)-46GUS, cl.2 pMON53046 traA6-box (3X)-46GUS, cl.21 pMON53047 traA7-box (3X)-46GUS, cl.15 pMON53048 traA8-box (3X)-46GUS, cl.4 pMON53049 traA9-box (3X)-46GUS, cl.8 pMON53050 traA-box (3X)-46GUS, cl.17 pMON53051 traA-1-box (3X)-46GUS, cl.14

Each of the constructs contained three copies of a double mutant oligonucleotide with symmetrical mutations in both halves of the palindrome (marked lower case in Table 2). These constructs were tested for background GUS activity and TraR responsiveness in carrot protoplasts. Results from two independent transfection experiments (Tables 5 and 6) indicate that three constructs, pMON53041 (traA1), pMON53042 (traA2) and pMON53048 (traA8) have retained the ability to be activated by VP16-TraR fusion, while others lost their responsiveness to TraR. At the same time, the background activity of these constructs was significantly reduced, resulting in higher levels of inducibility (up to 17-fold induction with the traA1 construct, lane 4 in Table 6).

Although the second transfection was not as efficient as the first transfection, its results support the conclusion that mutations at positions 1, 2 and 8 in the canonical tra-box (counting from the first nucleotide) can be tolerated by TraR and produce higher inducibility levels after stimulation with C8-AHL.

TABLE 5

Transient Expression Levels in Carrot Protoplasts for Constructs with Three Copies of the tra Box and tra-Box Variants (First Transfection)

| | Construct | 1 | 2 | 3 | − inducer | + inducer | 4 | 5 | 6 | fold +/− |
|---|---|---|---|---|---|---|---|---|---|---|
| 1 | tra box (6X), cl.7 | 709.3 | 517.2 | 635.4 | 620.6 | 620.2 | 569.8 | 647.3 | 643.6 | 1.0 |
| 2 | +HA-VP16-TraR 0/12.5 µM C8-AHL | 624.9 | 463.7 | 636.6 | 575.1 | 987.4 | 933.8 | 1033.2 | 995.1 | 1.7 |
| 3 | traA1(3X), cl.35 | 180.4 | 126.2 | 125.4 | 144.0 | 124.8 | 110.8 | 118.5 | 145.2 | 0.9 |
| 4 | +HA-VP16-TraR | 149.2 | 143.6 | 153.5 | 148.8 | 1941.5 | 1896.4 | 1959.7 | 1968.4 | 13.1 |
| 5 | traA2(3X), cl.43 | 374.4 | 247.1 | 261.9 | 294.5 | 230.5 | 240.6 | 221.1 | 229.7 | 0.8 |
| 6 | +HA-VP16-TraR | 251.8 | 272.8 | 232.0 | 252.2 | 2281.6 | 2198.3 | 2341.9 | 2304.6 | 9.0 |
| 7 | traA3(3X), cl.4 | 107.0 | 84.3 | 105.2 | 98.8 | 95.6 | 89.3 | 94.4 | 103.2 | 1.0 |
| 8 | +HA-VP16-TraR | 109.2 | 128.7 | 96.8 | 111.6 | 116.5 | 117.3 | 121.2 | 111.1 | 1.0 |
| 9 | traA4(3X), cl.23 | 220.6 | 210.0 | 174.1 | 201.5 | 189.6 | 177.7 | 196.0 | 195.0 | 0.9 |
| 10 | +HA-VP16-TraR | 123.1 | 159.0 | 135.7 | 139.3 | 122.8 | 142.9 | 112.2 | 113.5 | 0.9 |
| 11 | traA5(3X), cl.2 | 26.5 | 17.6 | 10.3 | 18.1 | 16.6 | 20.6 | 16.2 | 13.1 | 0.9 |
| 12 | +HA-VP16-TraR | 26.1 | 25.3 | 11.6 | 21.0 | 20.5 | 21.3 | 18.5 | 21.8 | 1.0 |
| 13 | traA6(3X), cl.21 | 107.2 | 88.8 | 64.2 | 86.7 | 71.3 | 73.6 | 64.2 | 76.1 | 0.8 |
| 14 | +HA-VP16-TraR | 79.2 | 79.1 | 77.2 | 78.5 | 64.6 | 64.8 | 64.2 | 64.7 | 0.8 |
| 15 | traA7(3X), cl.15 | 228.9 | 242.2 | 223.7 | 231.6 | 217.9 | 215.1 | 200.0 | 238.6 | 0.9 |
| 16 | +HA-VP16-TraR | 208.7 | 200.6 | 216.4 | 208.6 | 234.8 | 237.5 | 226.8 | 240.1 | 1.1 |
| 17 | traA8(3X), cl.4 | 69.1 | 38.8 | 43.0 | 50.3 | 39.8 | 36.3 | 43.3 | 39.8 | 0.8 |
| 18 | +HA-VP16-TraR | 74.1 | 63.2 | 64.4 | 67.2 | 888.0 | 828.8 | 874.3 | 960.9 | 13.2 |
| 19 | traA9(3X), cl.8 | 52.3 | 51.3 | 41.4 | 48.3 | 34.7 | 32.4 | 35.6 | 36.2 | 0.7 |
| 20 | +HA-VP16-TraR | 45.1 | 38.0 | 53.6 | 45.6 | 63.7 | 65.4 | 65.3 | 60.5 | 1.4 |
| 21 | min-46GUS | 178.9 | 140.7 | 136.8 | 152.1 | 128.5 | 145.4 | 124.2 | 116.0 | 0.8 |

"+ inducer" samples contained 12.5 µM C8-AHL. 35S-CAT was used in "reporter construct alone" transfections to compensate for TraR effector DNA.

TABLE 6

Transient Expression Levels in Carrot Protoplasts for Constructs with
Three Copies of the tra Box and tra-Box Variants (Second Transfection)

| Construct | 1 | 2 | 3 | − inducer | + inducer | 4 | 5 | 6 | fold +/− |
|---|---|---|---|---|---|---|---|---|---|
| 1 Tra box(3X), cl.5 + CAT | 312.0 | 244.8 | 290.5 | 282.4 | 249.1 | 264.6 | 251.9 | 230.9 | 0.9 |
| 2 +HA-VP16-TraR | 553.8 | 406.1 | 533.5 | 497.8 | 1576.2 | 1350.6 | 1542.2 | 1835.6 | 3.2 |
| 3 TraA1(3X), cl.35 + CAT | 89.3 | 52.6 | 61.0 | 67.6 | 55.9 | 70.7 | 54.2 | 42.8 | 0.8 |
| 4 +HA-VP16-TraR | 98.8 | 86.8 | 92.3 | 92.6 | 1560.4 | 1426.4 | 1490.9 | 1763.9 | 16.8 |
| 5 TraA2(3X), cl.43 + CAT | 115.7 | 117.6 | 140.4 | 124.6 | 112.8 | 125.2 | 103.0 | 110.2 | 0.9 |
| 6 +HA-VP16-TraR | 139.7 | 205.5 | 212.0 | 185.8 | 2057.1 | 1757.9 | 2255.2 | 2158.0 | 11.1 |
| 7 TraA3(3X), cl.4 + CAT | 61.1 | 58.3 | 58.6 | 59.3 | 56.1 | 59.2 | 62.8 | 46.4 | 0.9 |
| 8 +HA-VP16-TraR | 61.1 | 79.8 | 86.4 | 75.8 | 100.1 | 106.3 | 98.0 | 96.1 | 1.3 |
| 9 TraA4(3X), cl.23 + CAT | 78.2 | 72.5 | 74.8 | 75.1 | 86.7 | 87.9 | 86.4 | 85.9 | 1.2 |
| 10 +HA-VP16-TraR | 98.6 | 97.0 | 111.7 | 102.4 | 109.6 | 108.1 | 108.3 | 112.6 | 1.1 |
| 11 TraA5(3X), cl.2 + CAT | 80.8 | 67.1 | 45.9 | 64.6 | 77.2 | 72.5 | 68.2 | 90.9 | 1.2 |
| 12 +HA-VP16-TraR | 65.8 | 87.5 | 82.0 | 78.4 | 82.3 | 91.6 | 72.7 | 82.6 | 1.0 |
| 13 TraA6(3X), cl.21 + CAT | 8.5 | 7.0 | 10.3 | 8.6 | 3.9 | 4.8 | 5.4 | 1.6 | 0.5 |
| 14 +HA-VP16-TraR | 3.3 | 1.2 | 0.7 | 1.7 | 3.2 | 1.4 | 1.9 | 6.3 | 1.8 |
| 15 TraA7(3X), cl.15 + CAT | 248.5 | 239.3 | 205.4 | 231.1 | 235.6 | 241.3 | 197.1 | 268.5 | 1.0 |
| 16 +HA-VP16-TraR | 230.7 | 178.1 | 147.7 | 185.5 | 236.8 | 216.9 | 217.5 | 275.9 | 1.3 |
| 17 TraA8(3X), cl.4 + CAT | 169.4 | 126.8 | 128.7 | 141.7 | 128.7 | 121.2 | 148.8 | 115.9 | 0.9 |
| 18 +HA-VP16-TraR | 131.3 | 143.5 | 102.7 | 125.8 | 1759.1 | 1774.0 | 1839.9 | 1663.3 | 14.0 |
| 19 TraA9(3X), cl.8 + CAT | 101.2 | 85.7 | 89.5 | 92.1 | 94.6 | 97.4 | 96.7 | 89.6 | 1.0 |
| 20 +HA-VP16-TraR | 109.5 | 136.6 | 147.7 | 131.3 | 229.7 | 307.2 | 197.9 | 183.9 | 1.7 |
| 21 TraA10(3X), cl.17 + CAT | 59.6 | 54.6 | 54.4 | 56.2 | 45.1 | 47.1 | 44.2 | 44.1 | 0.8 |
| 22 +HA-VP16-TraR | 67.7 | 61.5 | 63.2 | 64.1 | 641.1 | 621.1 | 629.5 | 672.7 | 10.0 |
| 23 TraA-1(3X). cl.14 + CAT | 18.9 | 21.4 | 24.6 | 21.6 | 20.1 | 19.7 | 23.6 | 17.0 | 0.9 |
| 24 +HA-VP16-TraR | 28.7 | 16.7 | 22.1 | 22.5 | 26.7 | 25.1 | 25.0 | 30.0 | 1.2 |
| 25 min35S-46-GUS | 27.2 | 45.6 | 46.1 | 39.6 | 38.7 | 39.6 | 32.1 | 44.5 | 1.0 |

"+ inducer" samples contained 12.5 μM C8-AHL. 35S-CAT was used in "reporter construct alone" transfections to compensate for TraR effector DNA.

We have also tested constructs that contain four copies of the traA8-box (pMON53055, TraA8 (4X)-46GUS, cl.16), and achieved 25.7-fold induction (Table 7).

TABLE 7

Transient Expression Levels in Carrot Protoplasts for Constructs with
Three or Four Copies of the tra8 Box

| Construct (0/12.5 μM C8-AHL) | 1 | 2 | 3 | − inducer | + inducer | 4 | 5 | 6 | fold +/− |
|---|---|---|---|---|---|---|---|---|---|
| 1 S2-46GUS | 30.7 | 16.1 | 19.4 | 22.1 | 22.4 | 27.2 | 22.7 | 17.4 | 1.0 |
| 2 TraA8(4X), cl.16 + CAT | 28.0 | 27.9 | 34.4 | 30.1 | 21.3 | 20.3 | 25.1 | 18.7 | 0.7 |
| 3 +HA-VP16-TraR | 41.1 | 39.8 | 37.8 | 39.5 | 1015.3 | 1190.9 | 991.1 | 863.8 | 25.7 |
| 4 TraA8(3X), cl.4 (60 μg) + CAT | 66.4 | 87.3 | 61.6 | 71.8 | 70.0 | 76.6 | 75.1 | 58.1 | 1.0 |
| 5 +TraR | 121.5 | 122.4 | 111.5 | 118.4 | 1665.3 | 1867.2 | 1559.0 | 1569.7 | 14.1 |
| 6 +TraM | 111.5 | 115.8 | 116.6 | 114.6 | 98.0 | 105.0 | 102.1 | 86.8 | 0.9 |
| 7 +TraS | 152.1 | 143.8 | 139.6 | 145.1 | 135.7 | 143.6 | 128.8 | 134.8 | 0.9 |
| 8 TraA8(3X), cl.4 (25 μg) + TraR + TraM | 11.7 | 22.4 | 12.7 | 15.6 | 11.8 | 13.5 | 9.6 | 12.1 | 0.8 |
| 9 TraA8(3X), cl.4 (25 μg) + TraR + TraS | 32.4 | 50.5 | 29.7 | 37.5 | 248.3 | 279.4 | 224.4 | 241.0 | 6.6 |
| 10 TraA8(3X), cl.4 (25 μg) + TraR + CAT | 58.2 | 56.3 | 70.1 | 61.5 | 762.2 | 698.2 | 680.1 | 908.4 | 12.4 |

Table 7 also contains data that indicates that TraM and TraS can be used to downregulate TraR-mediated activation in plant cells, in a manner that is similar to what occurs in the natural host. This can be useful if it is desirable to prevent inducibility by AHL in certain organs, tissues or cell types. For example, by expressing TraM (which works very efficiently, compare lanes 8 and 10 of Table 7) under the control of appropriate tissue-specific promoter, the whole system can be kept inactive in the presence of ligand.

Example 7

Yeast AHL-Responsive Constructs

The functionality of AHL-responsive constructs was tested in yeast (*Saccharomyces cerevisiae*). In order to produce yeast reporter constructs, three copies of an AHL-responsive element, the tra and esa boxes, were cloned in pLacZi (a component of the "MATCHMAKER One-Hybrid System," cat.# K1603-1, Clontech Laboratories, Inc., Palo Alto, Calif.), a yeast integration and reporter vector, upstream of the minimal promoter of the yeast iso-1-cytochrome C gene ($P_{CYC1}$), with lacZ serving as the reporter gene. pLacZi is an integrative vector that can be stably integrated into the yeast genome after linearization. Effector plasmid constructs were produced by cloning TraR and EsaR into pGAL415 from a GAL1 galactose inducible promoter. When transformed into yeast cells, such activator/reporter pairs are useful for performing genetic screens for new alleles of AHL receptors with changed or improved characteristics, for screening for variant AHL molecules that are active as inducers, for tra-box mutations, etc. AHL-responsive yeast constructs are generally useful for regulating expression of foreign polypeptides in yeast cells.

*S. cerevisia* strain 204142, a non-pathogenic uracil, leucine, and tryptophan auxotroph (MATa ura3-52 leu2-delta1 trp1-delta63 [RF45527]) was transformed by the Lithium Acetate method with pLacZi-traA8(6X) to create a reporter strain with traA8(6X) LacZi:: ura3 (204142A). 204142A was then transformed with either pGAL415 carrying a leucine marker to create a control strain (204142B) or pGAL415TraR carrying a leucine marker to create a test strain (204142C). Beta-galactosidase activity was measured using the Galacto-Star chemiluminescent assay system (Tropix, Inc., Bedford, Mass.) following the manufacturers protocol, and summarized here.

All yeast strains were grown on solid medium plates (SD medium; 6.7 mg/ml yeast nitrogen and 40 mg/ml glucose plus agar), supplemented with the appropriate amino acids, tryptophan (0.4 mg/ml) and leucine (0.6 mg/ml) for 204142A, and supplemented with tryptophan (0.4 mg/ml) for 204142B and 204142C. Cells were grown overnight at 30° C. and used to inoculate SR growth liquid medium (6.7 mg/ml yeast nitrogen and 40 mg/ml glucose) supplemented with the appropriate amino acids. Inoculated cultures were put at 30° C. with shaking at 300 rpm in a flask or tube with an approximate 0.1 liquid to air ratio. Cells were grown to an absorbance of $A_{600}$ between 0.2 and 0.5.

Yeast cells were distributed in 450 ul allocates into 2 ml wells of 96-deep well plates. A 20% Glucose (repressor) or 20% Galactose (inducer) solution was distributed by 50 ul allocates to each well to produce a final concentration of 2%. Homoserine lactone (hsl) was added at various concentrations from a 100 mM stock solution in 100% DMSO. Control samples without hsl were supplemented with equal volumes of 100% DMSO.

Plates were put at 30° C. on a titer plate shaker set at speed 8 for 5 hours before removing 100 µl from each well for $A_{600}$ measurement. The remaining 400 µl of cells were lysed by adding 200 µl of 3× lysis solution (3× stock: 50 mM Potassium Phosphate (pH 7.8), 0.1% Triton X-100, 1 mg/ml CTAB, 1 mg/ml Sodium Desoxycholate, 1 mM DTT) and put at 4° C. overnight on a titer plate shaker set at speed 8.

The following day plates were brought to room temperature and 75 µl aliquots of cells were pipetted into black 96 well microtiter plates containing 75 µl of 2× substrate solution (Tropix, Inc, Bedford, Mass.), warmed to room temperature. The lysed cells and substrate solution were incubated at room temperature for 45 minutes before light emission was measured using a Victor® multilabel counter.

The remaining protein (525 µl) was harvested in the supernatant after centrifugation (4K15 Sigma® plate centrifuge, 6,000 rpm for 15 minutes at 4° C.). Protein concentration was measured using a Pierce BCA-200 Protein Assay Kit by mixing 25 µl of supernatant with 200 µl of the BCA working reagent in a clear 96 well microtiter plate. The mixture was incubated at 37° C. for 30 minutes before the $A_{562}$ was measured. A blank containing 1× lysis solution was subtracted from the sample readings and protein concentration was determined using a standard curve from BSA samples measured in the same assay.

Light emission was measured as counts per second (CPS). A row of blank CPS readings obtained from a mixture consisting of 1× lysis solution and 1× substrate solution was averaged and subtracted from each test CPS reading. Total protein calculated from BCA assay was divided into CPS to yield β-galactosidase activity (CPS/mg protein). To obtain fold increase between the samples, they were divided by the basal level of β-galactosidase activity seen in the control strain (204142B) under repressing conditions.

Figure 26:
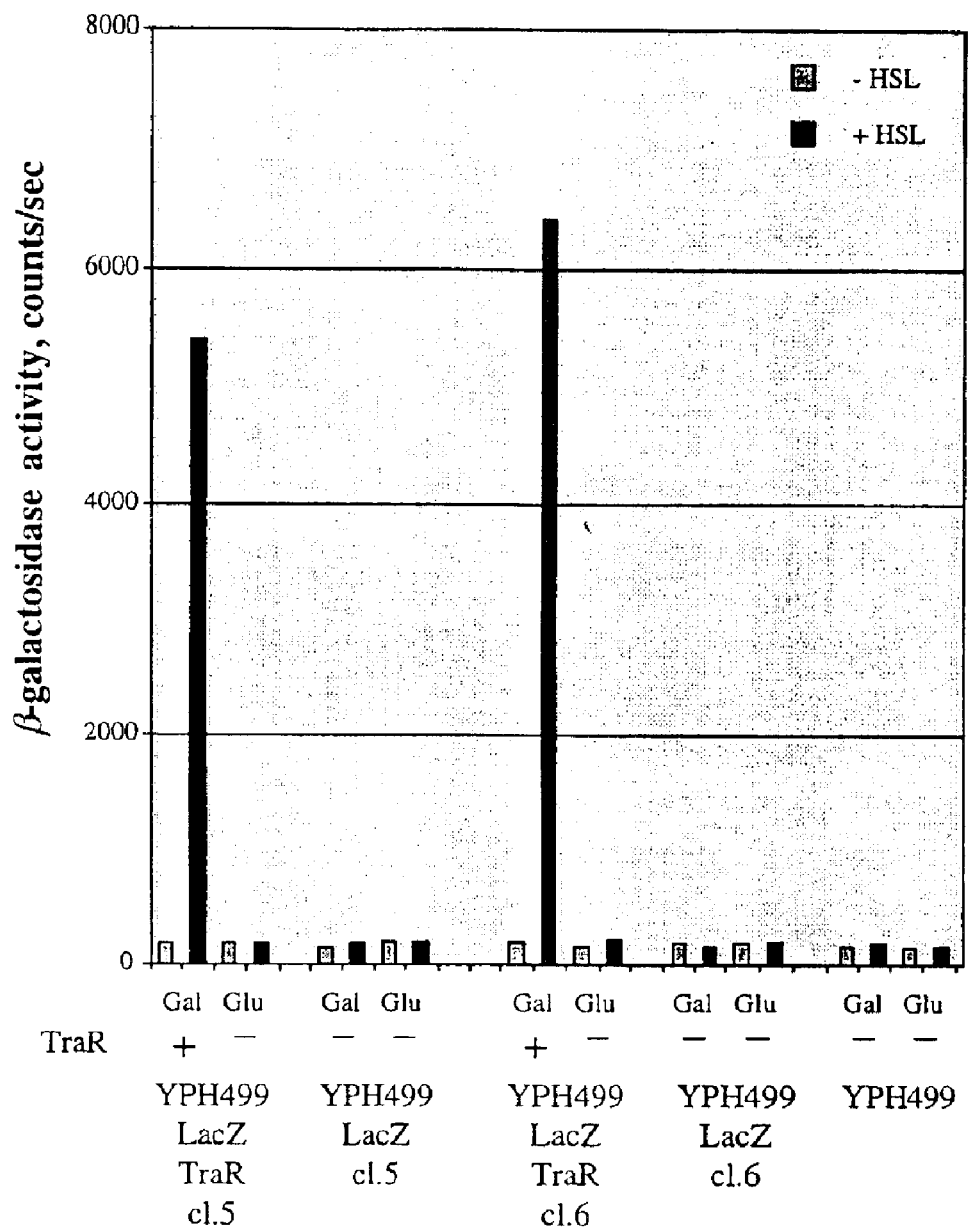
FIG. 26 provides the β-galactosidase activity in cell extracts from two independent lines (strain YPH499, cl.5 and cl.6) containing the β-galactosidase reporter gene driven by a minimal promoter with 3 copies of the TraA8 element.

The results of the reporter gene inducibility are shown in FIG. 26. A strong induction was observed in the presence of C8-HSL when yeast cells were grown on galactose, while in the absence of the inducer, or TraR (cells grown on glucose), the activity was below detection limits (indistinguishable from strains lacking TraR and/or lacZ reporter gene altogether). Cell extracts from two independent lines (strain YPH499, cl.5 and 6) containing β-galactosidase reporter gene driven by a minimal promoter with 3 copies of TraA8 element were tested for β-gal activity using chemiluminescent assay demonstrated strong induction after 5 hrs of growth on galactose in the presence of 50 µM C8-HSL. In the absence of AHL or TraR (5 hrs of growth on glucose), the activity detected in the extracts was as low as in YPH499 strain lacking LacZ reporter gene.

Example 8

Synthesis of AHL Analogs b-Ketoesters were prepared by a previously reported method Wierenga, et al. (1979) *J. Org. Chem.* 44(2):310–311.

General Procedure for the Preparation of 2-Azidobutyrolactones: The 2-bromobutyrolactones were prepared according to a previously reported procedure and were used without further purification (2). Crude 2-bromobutyrolactone (20–50 mmol) was dissolved in $CH_2Cl_2$ (20–40 ML). A phase transfer catalyst (Aliquat® 336, 10–20 drops) and a solution of sodium azide (4.8 equiv) dissolved in water (30–60 mL) were added to the $CH_2Cl_2$ solution. The biphase was vigorously stirred for 16–28 h, then water (50–75 mL) was added and the organic layer separated. The aqueous layer was washed with $CH_2Cl_2$ (3×40 mL). The combined organic layers were dried ($MgSO_4$), filtered and concentrated to afford a yellow liquid. All four diastereomers were observed. The crude products were purified and the cis isomers separated from the trans isomers by silica gel chromatography.

2(S)-Azido-2-methylbutyrolactone and 2(R)-Azido-2-methylbutyrolactone: The azidation reaction was carried out with 2-bromo-2-methylbutyrolactone (31.2 mmol). Purification was carried out by silica gel column chromatography (EtOAc:hexane, 7:93) to afford the products as a colorless liquids (2.1 g, 47%). $^1$H NMR (400 MHz, $CDCl_3$) d 4.32 (m, 2H), 2.25 (m, 2H), 1.62 (s, 3H); $^{13}$C NMR (100 MHz, $CDCl_3$) d 175.0, 65.1, 61.1, 35.3, 19.7.

2-Azido-3-methylbutyrolactones: 3-Methylbutyrolactone, required for preparation of the corresponding bromolactone, was prepared as previously reported (3,4), except methanol rather than ethanol was used in the hydrogenation reaction (Note: the crude product contained a significant amount of the methylester of the ring-opened product that arises from addition of methanol to the lactone. This sideproduct, however, was quantitatively converted to the desired product during distillation). The azidation reaction was carried out with 2-bromo-3-methylbutyrolactone (19.6 mmol). Purification was carried out by silica gel column chromatography (EtOAc:hexane, 15:85) to afford the products as a colorless liquids (1.52 g, 55%, cis:trans (isolated)=1:1.5). Cis isomers: $^1$H NMR (400 MHz, $CDCl_3$) d 4.36 (dd, J=9.1, 6.2 Hz, 1H), 4.28 (d, J=7.3 Hz, 1H), 4.02 (dd, J=9.1, 4.3 Hz, 1H), 2.75 (m, 1H), 1.12 (d, J=7.0 Hz, 3H); $^{13}$C NMR (100 MHz, $CDCl_3$) d 172.9, 72.3, 60.4, 34.4, 12.2. Trans isomers: $^1$H NMR (400 MHz, $CDCl_3$)

d 4.47 (dd, J=9.1, 7.8 Hz, 1H), 3.85 (d, J=9.4 Hz, 1H), 3.84 (t, J=8.1 Hz, 1H), 2.46 (m, 1H), 1.24 (d, J=6.7 Hz, 3H); $^{13}$C NMR (100 MHz, CDCl$_3$) d 173.2, 71.2, 63.3, 37.3, 14.6.

2-Azido-4-methylbutyrolactones: The azidation reaction was carried out with 2-bromo-4-methylbutyrolactone (Aldrich, 23.7 mmol). Purification was carried out by silica gel column chromatography (EtOAc:hexane, 15:85) to afford the cis products as a white crystalline solid and the trans products as a colorless liquid (2.8 g, 83%, cis:trans (isolated)=1.8:1). Cis isomers: $^1$H NMR (400 MHz, CDCl$_3$) d 4.56 (m, 1H), 4.36 (dd, J=11.0, 8.6 Hz, 1H), 2.69 (ddd, J=13.0, 8.5, 5.3 Hz, 1H), 1.76 (dt, J=12.9, 10.5 Hz, 1H), 1.47 (d, J=6.2 Hz, 3H); $^{13}$C NMR (100 MHz, CDCl$_3$) d 173.1, 74.3, 58.1, 36.5, 20.7. Trans isomers: $^1$H NMR (400 MHz, CDCl$_3$) d 4.76 (m, 1H), 4.33 (dd, J=8.1, 5.6 Hz, 1H), 2.27 (ddd, J=13.4, 7.0, 6.1 Hz, 1H), 2.13 (ddd, J=13.7, 8.1, 5.8 Hz, 1H), 1.42 (d, J=6.4 Hz, 3H); $^{13}$C NMR (100 MHz, CDCl$_3$) d 172.9, 75.5, 57.4, 35.6, 20.9.

2-Azido-4-ethylbutyrolactones: The azidation reaction was carried out with 2-bromo-4-ethylbutyrolactone (43.0 mmol). Purification was carried out by silica gel column chromatography (EtOAc:hexane, 10:90) to afford the products as a colorless liquids (3.2 g, 47%, cis:trans (isolated)=2.8:1). Cis isomers: $^1$H NMR (400 MHz, CDCl$_3$) d 4.37 (m, 1H), 4.35 (dd, J=11.1, 8.7 Hz, 1H), 2.64 (ddd, J=12.9, 8.7, 5.5 Hz, 1H), 1.74 (m, 3H), 1.02 (t, J=7.5 Hz, 3H); $^{13}$C NMR (100 MHz, CDCl$_3$) d 173.1, 79.1, 57.8, 34.4, 28.2, 9.1. Trans isomers: $^1$H NMR (400 MHz, CDCl$_3$) d 4.55 (m, 1H), 4.30 (dd, J=8.1, 6.2 Hz, 1H), 2.23 (ddd, J=13.7, 7.3, 6.4 Hz, 1H), 2.17 (ddd, J=14.0, 8.2, 5.6 Hz, 1H), 1.85–1.58 (m, 2H), 1.01 (t, J=7.4 Hz, 3H); $^{13}$C NMR (100 MHz, CDCl$_3$) d 172.9, 80.4, 57.2, 33.5, 28.2, 9.3.

2-Azido-4-butylbutyrolactones: The azidation reaction was carried out with 2-bromo-4-butylbutyrolactone (31.6 mmol). Purification was carried out by silica gel column chromatography (EtOAc:hexane, 10:90) to afford the products as a colorless liquids (2.9 g, 50%, cis:trans (isolated)=3.1:1). Cis isomers: $^1$H NMR (400 MHz, CDCl$_3$) d 4.42 (m, 1H), 4.36 (dd, J=11.0, 8.6 Hz, 1H), 2.66 (ddd, J=13.4, 8.1,4.7 Hz, 1H), 1.82–1.72 (m, 1H), 1.77 (dt, J=13.2, 10.6 Hz, 1H), 1.65 (m, 1H), 1.49–1.30 (m, 4H), 0.92 (t, J=7.0 Hz, 3H); $^{13}$C NMR (100 MHz, CDCl$_3$) d 173.1, 77.9, 57.8, 34.83, 34.80, 26.9, 22.2, 13.7. Trans isomers: $^1$H NMR (400 MHz, CDCl$_3$) d 4.60 (m, 1H), 4.29 (dd, J=8.1, 5.9 Hz, 1H), 2.23 (ddd, J=13.4, 7.1, 6.1 Hz, 1H), 2.15 (ddd, J=13.8, 8.0, 5.8 Hz, 1H), 1.77–1.55 (m, 2H), 1.48–1.30 (m, 4H), 0.92 (t, J=7.1 Hz, 3H); $^{13}$C NMR (100 MHz, CDCl$_3$) d 172.9, 79.2, 57.2, 35.0, 34.1, 27.2, 22.2, 13.7.

2-Azido-4-phenylbutyrolactones: The azidation reaction was carried out with 2-bromo-4-phenylbutyrolactone (21.7 mmol). Purification was carried out by silica gel column chromatography (EtOAc:hexane, 15:85) to afford the products as a colorless liquids (2.4 g, 54%, cis:trans (isolated)=3.7:1). Cis isomers: $^1$H NMR (400 MHz, CDCl$_3$) d 7.42–7.32 (m, 5H), 5.39 (dd, J=10.6, 5.5 Hz, 1H), 4.49 (dd, J=11.3, 8.6 Hz, 1H), 2.94 (ddd, J=13.2, 8.3, 5.3 Hz, 1H), 2.12 (dt, J=12.9, 11.0 Hz, 1H); $^{13}$C NMR (100 MHz, CDCl$_3$) d 172.8, 137.3, 129.1, 128.9, 125.7, 78.3, 58.1, 37.3. Trans isomers: $^1$H NMR (400 MHz, CDCl$_3$) d 7.43–7.26 (m, 5H), 5.64 (t, J=6.6 Hz, 1H), 4.36 (dd, J=7.7, 6.0 Hz, 1H), 2.55 (ddd, J=13.4, 7.0, 6.3 Hz, 1H), 2.48 (ddd, J=13.6, 7.7, 6.0 Hz, 1H); $^{13}$C NMR (100 MHz, CDCl$_3$) d 172.7, 138.0, 128.9, 128.8, 125.0, 79.2, 57.0, 36.8.

General Procedure for the Preparation of Homoserine Lactones Hydrochlorides: (Note: 2-Azido-4-phenylbutyrolactones were not reduced using this procedure). The corresponding 2-azidobutyrolactone (2–20 mmol) dissolved in methanol (2–10 mL/mmol, typically 5 mL/mmol), concentrated HCl (10–30 drops), and 10% Pd/C (dry, 3–10 mol %, typically 5 mol %) were stirred under an atmosphere of H$_2$ for 24 h or until TLC indicated no starting azide remained. The reaction was filtered through celite and concentrated in vacuo to remove methanol. The crude products were dissolved in 4N HCl (generally 1 mL/mmol), then frozen and lyotholized to afford the products as a white or off-white solids.

2-Methyl-(S)-homoserine lactone and 2-methyl-(R)-homoserine lactone hydrochlorides: The reaction was carried out using 2-azido-2-methylhomoserine lactone (6.1 mmol, cis isomers) to afford the products as an off-white hydroscopic solid (1.21 g, 131%). $^1$H NMR (400 MHz, CD$_3$OD) d 4.56 (td, J=9.5, 1.9Hz, 1H), 4.46 (td, J=9.9, 6.4 Hz, 1H), 2.64 (dt, J=12.9, 9.8 Hz, 1H), 2.52 (ddd, J=13.0, 6.5, 1.7 Hz, 1H), 1.64 (s, 3H); $^{13}$C NMR (100 MHz, CD$_3$OD) d 176.2, 66.8, 56.8, 34.4, 20.8.

3(R)-Methyl-(S)-homoserine lactone and 3(S)-methyl-(R)-homoserine lactone hydrochlorides: The reaction was carried out using 2-azido-3-methylhomoserine lactone (3.3 mmol, cis isomers) to afford the products as an amber hydroscopic solid (500 mg, 101%). The stereochemistry was assigned based on previous work (5). $^1$H NMR (400 MHz, CD$_3$OD) d 4.53 (m, 2H), 4.18 (d, J=9.1 Hz, 1H), 3.01 (m, 1H), 1.16 (d, J=7.3 Hz, 3H); $^{13}$C NMR (100 MHz, CD$_3$OD) d 173.5, 74.2, 53.3, 33.9, 13.0.

3(S)-Methyl-(S)-homoserine lactone and 3(R)-methyl-(R)-homoserine lactone hydrochlorides: The reaction was carried out using 2-azido-3-methylhomoserine lactone (2.2 mmol, trans isomers) to afford the products as an off-white solid (290 mg, 87%). The stereochemistry was assigned based on previous work (5). $^1$H NMR (400 MHz, CD$_3$OD) d 4.56 (t, J=8.5 Hz, 1H), 4.03 (d, J=11.5 Hz, 1H), 3.96 (t, J=9.7 Hz, 1H), 2.74 (m, 1H), 1.31 (d, J=6.5Hz, 3H); $^{13}$C NMR (100 MHz, CD$_3$OD) d 173.8, 72.9, 55.8, 37.1, 14.0.

4(S)-Methyl-(R)-homoserine lactone and 4(R)-methyl-(S)-homoserine lactone hydrochlorides: The reaction was carried out using 2-azido-4-methylhomoserine lactone (10.4 mmol, cis isomers) to afford the products as a off-white solid (1.6 g, 102%). $^1$H NMR (400 MHz, CD$_3$OD) d 4.85 (m, 1H), 4.54 (dd, J=12.0, 8.7 Hz, 1H), 2.94 (ddd, J=12.8, 8.4, 4.8 Hz, 1H), 2.07 (q, J=11.8 Hz, 1H), 1.50 (d, J=6.2 Hz, 3H); $^{13}$C NMR (100 MHz, CD$_3$OD) d 174.1, 77.3, 50.2, 34.6, 19.7.

4(S)-Methyl-(S)-homoserine lactone and 4(R)-methyl-(R)-homoserine lactone hydrochlorides: The reaction was carried out using 2-azido-4-methylhomoserine lactone (6.2 mmol, trans isomers) to afford the products as an off-white solid (910 mg, 98%). $^1$H NMR (400 MHz, CD$_3$OD) d 4.87 (bm, 1H), 4.42 (bt, J=9.4 Hz, 1H), 2.40 (bm, 2H), 1.28 (bd, J=4.8 Hz, 3H); $^{13}$C NMR (100 MHz, CD$_3$OD) d 174.3, 77.5, 48.2, 32.1, 20.1.

4(S)-Ethyl-(R)-homoserine lactone and 4(R)-ethyl-(S)-homoserine lactone hydrochlorides: The reaction was carried out using 2-azido-4-ethylhomoserine lactone (7.9 mmol, cis isomers) to afford the products as a white solid (1.3 g, 97%). $^1$H NMR (400 MHz, CD$_3$OD) d 4.55 (m, 1H), 4.43 (dd, J=12.1, 8.9 Hz, 1H), 2.82 (ddd, J=12.4, 8.6, 5.1 Hz, 1H), 1.96 (td, J=12.2, 10.5 Hz, 1H), 1.79 (m, 2H), 1.04 (t, J=7.5 Hz, 3H); $^{13}$C NMR (100 MHz, CD$_3$OD) d 173.4, 81.3, 50.8, 34.1, 28.9, 9.5.

4(S)-Ethyl-(S)-homoserine lactone and 4(R)-ethyl-(R)-homoserine lactone hydrochlorides: The reaction was carried out using 2-azido-4-ethylhomoserine lactone (4.9 mmol, trans isomers) to afford the products as an off-white hydroscopic solid (760 mg, 94%). $^1$H NMR (400 MHz, CD$_3$OD) d 4.69 (m, 1H), 4.43 (t, J=9.8 Hz, 1H), 2.52 (m, 2H), 1.75 (m, 2H), 1.02 (t, J=7.4 Hz, 3H); $^{13}$C NMR (100 MHz, CD$_3$OD) d 173.6, 81.8, 49.0, 31.8, 29.1, 9.9.

4(S)-Butyl-(R)-homoserine lactone and 4(R)-butyl-(S)-homoserine lactone hydrochlorides: The reaction was carried out using 2-azido-4-butylhomoserine lactone (12.0 mmol, cis isomers) to afford the products as a white solid (2.1 g, 91%). $^1$H NMR (400 MHz, CD$_3$OD) d 4.61 (m, 1H), 4.42 (dd, J=12.1, 8.6 Hz, 1H), 2.82 (ddd, J=12.3, 8.7, 5.1 Hz, 1H), 1.96 (td, J=12.1, 10.7 Hz, 1H), 1.85–1.66 (m, 2H), 1.54–1.29 (m, 4H), 0.95 (t, J=7.1 Hz, 3H); $^{13}$C NMR (100 MHz, CD$_3$OD) d 173.4, 80.2, 50.8, 35.7, 34.6, 28.3, 23.4, 14.2.

4(S)-Butyl-(S)-homoserine lactone and 4(R)-butyl-(R)-homoserine lactone hydrochlorides: The reaction was carried out using 2-azido-4-butylhomoserine lactone (3.9 mmol, trans isomers) to afford the products as an off-white hydroscopic solid (690 mg, 92%). $^1$H NMR (400 MHz, CD$_3$OD) d 4.74 (m, 1H), 4.42 (t, J=9.8 Hz, 1H), 2.49 (m, 2H), 1.86–1.63 (m, 2H), 1.54–1.28 (m, 4H), 0.95 (t, J=6.9 Hz, 3H); $^{13}$C NMR (100 MHz, CD$_3$OD) d 173.6, 80.6, 53.6, 35.8, 32.2, 28.6, 23.3, 14.2.

4(S)-Phenyl-(R)-homoserine lactone and 4(R)-phenyl-(S)-homoserine lactone hydrochlorides: The phenyl substituted compounds were reduced by the method described by Bloch and coworkers (6). The reaction was carried out using 2-azido-4-phenylhomoserine lactone (8.8 mmol, cis isomers, addition/stirring over 0.75 h, heat 2 h) to afford the products as a white solid (2.3 g, 117%). The products also contained PPh$_3$ and P(O)Ph$_3$ impurities as determined by NMR spectroscopy. Integration of the products and the impurities indicated the mixture was 65.9% by weight products (1.6 g, 85% product yield) and were used without further purification. $^1$H NMR (400 MHz, CD$_3$OD) d 7.66–7.39 (m, 5H), 5.62 (dd, J=10.8, 5.4 Hz, 1H), 4.62 (dd, J=12.1, 8.6 Hz, 1H), 3.11 (ddd, J=12.5, 8.5, 5.2 Hz, 1H), 2.33 (td, J=12.2, 11.0 Hz, 1H); $^{13}$C NMR (100 MHz, CD$_3$OD) d 173.2, 138.8, 130.0, 129.9, 127.3, 80.7, 51.2, 37.1.

4(S)-Phenyl-(S)-homoserine lactone and 4(R)-phenyl-(R)-homoserine lactone hydrochlorides: The phenyl substituted compounds were reduced by the method described by Bloch and coworkers (6). The reduction was carried out using 2-azido-4-phenylhomoserine lactone (2.4 mmol, trans isomers, addition/stirring over 3.5 h, heat 3 h) to afford the products as a white solid (680 mg, 135%). Under these conditions, racemization was observed at the 2-position to afford a 2:1 mixture trans:cis isomers. The products also contained PPh$_3$ and P(O)Ph$_3$ impurities as determined by NMR spectroscopy. Integration of the products and the impurities indicated the mixture was 73.2% by weight products (498 mg, 99% product yield) and were used without further purification. $^1$H NMR (400 MHz, CD$_3$OD) d 7.66–7.39 (m, 5H), 5.87 (dd, J=8.5, 2.6 Hz, 1H), 4.42 (t, J=9.7 Hz, 1H), 2.88 (ddd, J=13.3, 10.2, 8.5 Hz, 1H), 2.80 (ddd, J=13.0, 9.6, 3.2 Hz, 1H); $^{13}$C NMR (100 MHz, CD$_3$OD) d 173.5, 139.8, 130.1, 129.8, 126.3, 80.2, 51.2, 34.8.

General Procedure for the Preparation of N-Acylhomoserine Lactones: A mixture of ethyl ester (1–5 mmol) and 5% sodium hydroxide (1.7 equiv) was stirred at 35° C. for 1–1.5 hour and then was added to dichloromethane (75–100 mL). The mixture was cooled in an ice bath, vigorously stirred, then concentrated hydrochloric acid (1.8 equiv) was added dropwise (Note: significant excess acid or heat results in decarboxylation of b-ketocarboxylic acid products). The dichloromethane layer was separated, dried (MgSO$_4$), and concentrated in vacuo at ambient temperature. The white solid residue was taken up in anhydrous THF (10–15 mL) and was added to a stirred suspension of homoserine lactone hydrobromide or hydrochloride (0.8 equiv), benzotriazole-1-yl-oxy-tris-pyrrolidino-phosphonium hexafluorophosphate (0.9 equiv), and diisopropyl ethylamine (1.8 equiv) in anhydrous THF (15 mL). The reaction mixture was stirred at ambient temperature for 18–24 hours. The resulting solution was concentrated in vacuo, dissolved in ethyl acetate and again concentrated to afford an amber oil. The crude product was purified by silica gel chromatography to afford a white solid. In most cases, two chromatographic separations were required to obtain pure material.

N-(b-Ketooctanoyl)-2-methyl-(S)-homoserine lactone and N-(b-ketooctanoyl)-2-methyl-(R)-homoserine lactone: The reaction was carried out with ethyl 3-oxooctanoate (3.3 mmol) and 3-methylhomoserine lactone hydrochloride (2.6 mmol). Purification was carried out by radial silica gel chromatography in two sequential runs (EtOAc:hexane, 1:1 then EtOAc:CH$_2$Cl$_2$, 25:75) to afford the product as a white solid (37 mg, 6%). $^1$H NMR (400 MHz, CDCl$_3$) d 7.70 (bs, 1H), 4.50 (td, J=9.4, 2.4 Hz, 1H), 4.25 (td, J=9.3, 7.4 Hz, 1H), 3.45 (d, J=17.7, Hz, 1H), 3.22 (d, J=17.7, Hz, 1H), 2.52 (t, J=7.4 Hz, 2H), 2.28 (ddd, J=12.8, 7.3, 2.6 Hz, 1H), 1.60–1.50 (m, 2H), 1.53 (s, 3H), 1.36–1.21 (m, 4H), 0.89 (t, J=7.0 Hz, 3H); $^{13}$C NMR (100 MHz, CDCl$_3$) d 206.8, 177.1, 165.6, 65.2, 55.6, 48.2, 43.7, 34.2, 31.0, 22.9, 22.5, 22.3, 13.8; HRMS Calcd for M+H C$_{13}$H$_{22}$NO$_4$: 256.1549. Found: 256.1562.

N-(b-Ketooctanoyl)-3(S)-methyl-(R)-homoserine lactone and N-(b-ketooctanoyl)-3(R)-methyl-(S)-homoserine lactone: The reaction was carried out with ethyl 3-oxooctanoate (2.6 mmol) and 3-methylhomoserine lactone hydrochloride (1.9 mmol, cis isomers). Purification was carried out by silica gel column chromatography followed by radial silica gel chromatography (EtOAc:hexane, 1:1; then EtOAc:CH$_2$Cl$_2$, 1:3) to afford the product as a white solid (100 mg, 22%). $^1$H NMR (400 MHz, CDCl$_3$) d 7.73 (bd, J=5.1 Hz, 1H), 4.77 (t, J=6.9 Hz, 1H), 4.43 (dd, J=9.1, 5.1 Hz, 1H), 4.11 (d, J=9.4 Hz, 1H), 3.50 (s, 2H), 2.98 (m, 1H), 2.54 (t, J=7.4 Hz, 2H), 1.64–1.56 (m, 2H), 1.36–1.24 (m, 4H), 1.01 (d, J=7.3 Hz, 3H), 0.89 (t, J=7.0 Hz, 3H); $^{13}$C NMR (100 MHz, CDCl$_3$) d 206.1, 174.6, 166.5, 72.6, 53.1, 48.3, 43.8, 33.8, 31.1, 28.1, 23.0, 22.3, 13.8, 12.8; HRMS Calcd for M+H C$_{13}$H$_{22}$NO$_4$: 256.1549. Found: 256.1550.

N-(b-Ketooctanoyl)-3(S)-methyl-(S)-homoserine lactone and N-(b-ketooctanoyl)-3(R)-methyl-(R)-homoserine lactone: The reaction was carried out with ethyl 3-oxooctanoate (2.4 mmol) and 3-methylhomoserine lactone hydrochloride (1.8 mmol, trans isomers). Purification was carried out by silica gel column chromatography followed by radial silica gel chromatography (EtOAc:hexane, 1:1) to afford the product as a white solid (260 mg, 43%). $^1$H NMR (400 MHz, CDCl$_3$) d 7.57 (bd, J=7.8 Hz, 1H), 4.45 (t, J=8.5 Hz, 1H), 4.38 (dd, J=11.6, 8.1 Hz, 1H), 3.85 (dd, J=10.7, 9.1 Hz, 1H), 3.49 (s, 2H), 2.61 (m, 1H), 2.54 (t, J=7.4 Hz, 2H), 1.63–1.56 (m, 2H), 1.35–1.23 (m, 4H), 1.21 (d, J=6.7 Hz, 3H), 0.89 (t, J=7.0 Hz, 3H); $^{13}$C NMR (100 MHz, CDCl$_3$) d 206.6, 174.6, 166.6, 71.4, 55.2, 48.3, 43.7, 37.8, 31.1, 28.1, 23.0, 22.3, 14.7, 13.8; HRMS Calcd for M+H C$_{13}$H$_{22}$NO$_4$: 256.1549. Found: 256.1551.

N-(b-Ketooctanoyl)-4(R)-methyl-(S)-homoserine lactone and N-(b-ketooctanoyl)-4(S)-methyl-(R)-homoserine lactone: The reaction was carried out with ethyl 3-oxooctanoate (0.95 mmol) and 4-methylhomoserine lactone hydrochloride (0.40 mmol, cis isomers). Purification was carried out by radial silica gel chromatography twice (first using EtOAc:hexane, 3:2, then using iPrOH:CH$_2$Cl$_2$, 1:20) to afford the product as a clear colorless liquid (67 mg, 71%). $^1$H NMR (400 MHz, CDCl$_3$) d 7.55 (bd, J=5.4 Hz, 1H), 4.62 (ddd, J=12.2, 8.4, 6,8 Hz, 1H), 4.49 (m, 1H), 3.39 (s, 2H), 2.78 (ddd, J=12.6, 8.1, 4.8 Hz, 1H), 2.45 (t, J=7.4 Hz, 2H), 1.74 (t,d, J=12.1, 10.9 Hz, 1H), 1.52 (m, 2H), 1.40 (d, J=6.2 Hz, 3H), 1.30–1.15 (m, 4H), 0.82 (t, J=6.7 Hz, 3H); $^{13}$C NMR (100 MHz, CDCl$_3$) d 206.5, 174.4, 166.3, 74.6, 50.7, 48.2, 43.8, 37.8, 31.1, 23.0, 22.3, 20.6, 13.8; HRMS Calcd for M+H C$_{13}$H$_{22}$NO$_4$: 256.1549. Found: 256.1539.

N-(b-Ketooctanoyl)-4(R)-methyl-(R)-homoserine lactone and N-(b-ketooctanoyl)-4(S)-methyl-(S)-homoserine lactone: The reaction was carried out with ethyl 3-oxooctanoate (0.58 mmol) and 4-methylhomoserine lactone hydrochloride (0.43 mmol, trans isomers). Purification was carried out by radial silica gel chromatography twice (first using EtOAc:CH$_2$Cl$_2$:hexane, 6:1:3; then iPrOH:EtOAc:CH$_2$Cl$_2$, 1:1:20) to afford the product as a white solid (31 mg, 27%). $^1$H NMR (400 MHz, CDCl$_3$) d 7.60 (bd, J=5.6 Hz, 1H), 4.77 (m, 1H), 4.59 (td, J=9.7, 6.7 Hz, 1H), 3.39 (s, 2H), 2.45 (t, J=7.4 Hz, 2H), 2.39–2.22 (m, 2H), 1.52 (m, 2H), 1.36 (d, J=6.5 Hz, 3H), 1.30–1.15 (m, 4H), 0.82 (t, J=7.1 Hz, 3H); $^{13}$C NMR (100 MHz, CDCl$_3$) d 206.7, 174.5, 166.2, 74.8, 48.3, 48.0, 43.9, 35.4, 31.1, 23.0, 22.4, 21.3, 13.8; HRMS Calcd for M+H C$_{13}$H$_{22}$NO$_4$: 256.1549. Found: 256.1556.

N-(b-Ketooctanoyl)-4(R)-ethyl-(S)-homoserine lactone and N-(b-ketooctanoyl)-4(S)-ethyl-(R)-homoserine lactone: The reaction was carried out with ethyl 3-oxooctanoate (3.2 mmol) and 4-ethylhomoserine lactone hydrochloride (2.4 mmol, cis isomers). Purification was carried out by silica gel column chromatography followed by radial silica gel chromatography (EtOAc:hexane, 1:1; then EtOAc:CH$_2$Cl$_2$, 10:90) to afford the product as a white solid (310 mg, 48%). $^1$H NMR (400 MHz, CDCl$_3$) d 7.62 (bd, J=6.2 Hz, 1H), 4.69 (ddd, J=12.1, 8.3, 6.7 Hz, 1H), 4.38 (m, 1H), 3.47 (s, 2H), 2.80 (ddd, J=12.4, 8.3, 5.0 Hz, 1H), 2.53 (t, J=7.4 Hz, 2H), 1.88–1.55 (m, 6H), 1.36–1.22 (m, 4H), 1.01 (t, J=7.5 Hz, 3H), 0.89 (t, J=7.0 Hz, 3H); $^{13}$C NMR (100 MHz, CDCl$_3$) d 206.4, 174.5, 166.2, 79.4, 50.4, 48.3, 43.7, 35.6, 31.1, 28.1, 23.0, 22.3, 13.8, 9.1; HRMS Calcd for M+H C$_{14}$H$_{24}$NO$_4$: 270.1705. Found: 270.1692.

N-(b-Ketooctanoyl)-4(R)-ethyl-(R)-homoserine lactone and N-(b-ketooctanoyl)-4(S)-ethyl-(S)-homoserine lactone: The reaction was carried out with ethyl 3-oxooctanoate (2.4 mmol) and 4-ethylhomoserine lactone hydrochloride (1.8 mmol, trans isomers). Purification was carried out by silica gel column chromatography (EtOAc:hexane, 1:1) to afford the product as a white solid (300 mg, 62%). $^1$H NMR (400 MHz, CDCl$_3$) d 7.70 (bd, J=6.4 Hz, 1H), 4.60 (m, 2H), 3.46 (s, 2H), 2.53 (t, J=7.4 Hz, 2H), 2.48–2.41 (m, 1H), 2.35–2.27 (m, 1H), 1.80–1.55 (m, 6H), 1.36–1.22 (m, 4H), 1.01 (t, J=7.4 Hz, 3H), 0.89 (t, J=6.9 Hz, 3H); $^{13}$C NMR (100 MHz, CDCl$_3$) d 206.5, 174.8, 166.3, 79.9, 48.4, 48.2, 43.7, 33.4, 31.1, 28.4, 23.0, 22.3, 13.8, 9.5; HRMS Calcd for M+H C$_{14}$H$_{24}$NO$_4$: 270.1705. Found: 270.1700.

N-(b-Ketooctanoyl)-4(R)-butyl-(S)-homoserine lactone and N-(b-ketooctanoyl)-4(S)-butyl-(R)-homoserine lactone: The reaction was carried out with ethyl 3-oxooctanoate (1.0 mmol) and 4-butylhomoserine lactone hydrochloride (1.2 mmol, cis isomers). Purification was carried out by radial silica gel chromatography (EtOAc:CH$_2$Cl$_2$:hexane, 3:2:5) to afford the product as a white solid (204 mg, 68%). $^1$H NMR (400 MHz, CDCl$_3$) d 7.59 (bd, J=5.6 Hz, 1H), 4.66 (ddd, J=12.1, 8.2, 6.6 Hz, 1H), 4.42 (m, 1H), 3.46 (s, 2H), 2.83 (ddd, J=12.6, 8.2, 4.7 Hz, 1H), 2.52 (t, J=7.4 Hz, 2H), 1.86–1.74 (m, 3H), 1.72–1.54 (m, 2H), 1.50–1.20 (m, 8H), 0.92 (t, J=7.1 Hz, 3H), 0.89 (t, J=6.8 Hz, 3H); $^{13}$C NMR (100 MHz, CDCl$_3$) d 206.5, 174.4, 166.2, 78.3, 50.4, 48.1, 43.9, 36.3, 34.8, 31.1, 27.1, 23.0, 22.3, 13.9, 13.8; HRMS Calcd for M+H C$_{16}$H$_{28}$NO$_4$: 298.2018. Found: 298.2016.

N-(b-Ketooctanoyl)-4(R)-butyl-(R)-homoserine lactone and N-(b-ketooctanoyl)-4(S)-butyl-(S)-homoserine lactone: The reaction was carried out with ethyl 3-oxooctanoate (2.3 mmol) and 4-butylhomoserine lactone hydrochloride (1.1 mmol, trans isomers). Purification was carried out by by radial silica gel chromatography (EtOAc:CH$_2$Cl$_2$:hexane, 3:2:5) twice to afford the product as a white solid (210 mg, 64%). $^1$H NMR (400 MHz, CDCl$_3$) d 7.64 (bd, J=6.2 Hz, 1H), 4.63 (m, 2H), 3.46 (s, 2H), 2.52 (t, J=7.4 Hz, 2H), 2.46 (ddd, J=12.8, 9.7, 2.8 Hz, 1H), 2.29 (ddd, J=13.0, 10.1, 8.5 Hz, 1H), 1.78–1.66 (m, 1H), 1.66–1.54 (m, 3H), 1.48–1.22 (m, 8H), 0.91 (t, J=7.1 Hz, 3H), 0.89 (t, J=7.0 Hz, 3H); $^{13}$C NMR (100 MHz, CDCl$_3$) d 206.7, 174.6, 166.1, 78.6, 48.4, 47.9, 43.9, 35.1, 34.0, 31.1, 27.4, 23.0, 22.35, 22.29, 13.9, 13.8; HRMS Calcd for M+H C$_{16}$H$_{28}$NO$_4$: 298.2018. Found: 298.2024.

N-(b-Ketooctanoyl)-4(R)-phenyl-(S)-homoserine lactone and N-(b-ketooctanoyl)-4(S)-phenyl-(R)-homoserine lactone: The reaction was carried out with ethyl 3-oxooctanoate (1.3 mmol) and 4-phenylhomoserine lactone hydrochloride (1.2 mmol, cis isomers). Purification was carried out by radial silica gel chromatography (EtOAc:CH$_2$Cl$_2$, 1:9) twice to afford the product as a white solid (273 mg, 71%). $^1$H NMR (400 MHz, CDCl$_3$) d 7.77 (bd, J=6.2 Hz, 1H), 7.40–7.35 (m, 5H), 5.41 (dd, J=11.0, 5.4 Hz, 1H), 4.80 (ddd, J=12.1, 8.2, 6.9 Hz, 1H), 3.48 (s, 2H), 3.07 (ddd, J=12.6, 8.3, 5.4 Hz, 1H), 2.52 (t, J=7.4 Hz, 2H), 2.24 (q, J=11.9 Hz, 1H), 1.62–1.55 (m, 2H), 1.36–1.21 (m, 4H), 0.88 (t, J=7.0 Hz, 3H); $^{13}$C NMR (100 MHz, CDCl$_3$) d 206.5, 174.0, 166.3, 137.8, 128.9, 128.8, 125.9, 78.8, 50.8, 48.1, 43.8, 38.2, 31.1, 23.0, 22.3, 13.8; HRMS Calcd for M+H C$_{18}$H$_{24}$NO$_4$: 318.1705. Found: 318.1707.

N-(b-Ketooctanoyl)-4(R)-phenyl-(R)-homoserine lactone and N-(b-ketooctanoyl)-4(S)-phenyl-(S)-homoserine lactone: The reaction was carried out with ethyl 3-oxooctanoate (1.0 mmol) and 4-phenylhomoserine lactone hydrochloride (1.1 mmol, trans:cis=2:1). Purification and separation of the trans isomers was carried out by radial silica gel chromatography (EtOAc:CH$_2$Cl$_2$, 1:9) three times to afford the product as a white solid (144 mg, 41%). $^1$H NMR (400 MHz, CDCl$_3$) d 7.77 (bd, J=6.7 Hz, 1H), 7.41–7.28 (m, 5H), 5.75 (dd, J=8.3, 2.7 Hz, 1H), 4.58 (td, J=9.6, 6.8 Hz, 1H), 3.47 (s, 2H), 2.77 (ddd, J=12.7, 9.3, 3.2 Hz, 1H), 2.68 (ddd, J=12.9, 10.1, 8.5 Hz, 1H), 2.52 (t, J=7.4 Hz, 2H), 1.63–1.55 (m, 2H), 1.36–1.22 (m, 4H), 0.89 (t, J=7.0 Hz, 3H); $^{13}$C NMR (100 MHz, CDCl$_3$) d 206.7, 174.6, 166.2, 139.0, 128.9, 128.4, 124.9, 78.4, 48.2, 48.0, 43.9, 36.4, 31.1, 23.0, 22.3, 13.8; HRMS Calcd for M+H C$_{18}$H$_{24}$NO$_4$: 318.1705. Found: 318.1695.

N-(α-Methyl-b-ketooctanoyl)-(S)-homoserine: The reaction was carried out with ethyl 2-methyl-3-oxooctanoate (0.57 mmol) and (S)-homoserine lactone hydrobromide (0.85 mmol). Purification was carried out by radial silica gel column chromatography (EtOAc:CH$_2$Cl$_2$, 1:4, then iPrOH:CH$_2$Cl$_2$, 1:20) to afford the product as a white solid (69 mg, 47%). $^1$H NMR (400 MHz, CDCl$_3$) d 6.95 (bs, 1H), 4.57–4.44 (m, 2H), 4.30–4.22 (m, 1H), 3.50–3.42 (m, 1H), 2.81–2.70 (m, 1H), 2.58–2.52 (m, 2H), 2.25–2.10 (m, 1H), 1.60–1.52 (m, 2H), 1.45–1.38 (m, 3H), 1.25–1.19 (m, 4H), 0.87 (t, J=7.2 Hz, 3H); $^{13}$C NMR (100 MHz, CDCl$_3$) d 210.56, 210.52, 175.73, 175.72, 171.42, 171.39, 66.91, 66.86, 54.59, 54.55, 50.26, 50.19, 42.79, 42.54, 32.2, 30.9, 24.0, 23.4, 16.33, 16.25, 14.9; HRMS Calcd for M+H $C_{13}H_{21}NO_4$: 256.1549. Found: 256.1560.

N-(α,α-Dimethyl-b-ketooctanoyl)-(S)-homoserine: After ester hydrolysis the reaction was carried out with 2,2-dimethyl-3-oxooctanoic acid (0.46 mmol) and (S)-homoserine lactone hydrobromide (0.85 mmol). Purification was carried out by radial silica gel column chromatography ($EtOAc:CH_2Cl_2$, 1:4, then $CH_2Cl_2:EtOAc:hexane$, 1:1:3) to afford the product as a white solid (51 mg, 41%). $^1$H NMR (400 MHz, $CDCl_3$) d 6.45 (bs, 1H), 4.53–4.43 (m, 2H), 4.32–4.23 (m, 1H), 2.81–2.72 (m, 1H), 2.52 (t, J=7.2 Hz, 2H), 2.21–2.09 (m, 1H), 1.60–1.51 (m, 2H), 1.41 (d, J=2.4 Hz, 6H), 1.30–1.19 (m, 4H), 0.87 (t, J=7.2 Hz, 3H); $^{13}$C NMR (100 MHz, $CDCl_3$) d 211.1, 174.9, 173.2, 66.0, 55.7, 49.5, 38.3, 31.4, 29.9, 23.5, 22.7, 22.6, 14.0; HRMS Calcd for M+H $C_{14}H_{23}NO_4$: 270.1705. Found: 270.1700.

N-(α-Ethyl-b-ketooctanoyl)-(S)-homoserine: After ester hydrolysis the reaction was carried out with 2-ethyl-3-oxooctanoic acid (0.81 mmol) and (S)-homoserine lactone hydrobromide (0.77 mmol). Purification was carried out by radial silica gel column chromatography ($EtOAc:CH_2Cl_2$, 1:4, then EtOAc:hexane, 1:1) to afford the product as a white solid (155 mg, 74%). $^1$H NMR (400 MHz, $CDCl_3$) d 6.97 (bd, J=35.5 Hz, 1H), 4.58–4.50 (m, 1H), 4.50–4.42 (m, 1H), 4.30–4.21 (m, 1H), 3.37 (q, J=8.0 Hz, 1H), 2.81–2.68 (m, 1H), 2.58–2.50 (m, 2H), 2.23–2.10 (m, 1H), 1.98–1.80 (m, 2H), 1.62–1.52 (m, 4H), 1.36–1.20 (m, 4H), 0.96 (q, J=5.6 Hz, 3H), 0.87 (t, J=7.2 Hz, 3H); $^{13}$C NMR (100 MHz, $CDCl_3$) d 209.90, 209.83, 174.7, 169.6, 169.5, 66.0, 65.9, 61.3, 61.2, 49.3, 49.2, 43.2, 42.9, 31.3, 30.05, 30.01, 24.96, 24.94, 23.0, 22.5, 14.0, 11.93, 11.90; HRMS Calcd for M+H $C_{14}H_{23}NO_4$: 270.1705. Found: 270.1692.

N-(α-Butyl-b-ketooctanoyl)-(S)-homoserine: After ester hydrolysis the reaction was carried out with 2-butyl-3-oxooctanoic acid (0.23 mmol) and (S)-homoserine lactone hydrobromide (0.36 mmol). Purification was carried out by radial silica gel column chromatography (EtOAc:hexane, 1:1, then $EtOAc:CH_2Cl_2$, 1:4) to afford the product as a white solid (36 mg, 52%). $^1$H NMR (400 MHz, $CDCl_3$) d 6.89 (bd, J=35.5 Hz, 1H), 4.56–4.41 (m, 2H), 4.33–4.21 (m, 1H), 3.42 (q, J=7.4 Hz, 1H), 2.80–2.70 (m, 1H), 2.56–2.48 (m, 2H), 2.22–2.08 (m, 1H), 1.96–1.72 (m, 2H), 1.63–1.50 (m, 2H), 1.38–1.20 (m, 8H), 0.93–0.84 (m, 6H); $^{13}$C NMR (100 MHz, $CDCl_3$) d 207.2, 207.1, 174.8, 169.69, 169.62, 66.0, 65.9, 60.82, 60.80, 49.4, 49.3, 31.6, 30.85, 30.83, 29.9, 29.8, 29.6, 29.14, 29.13, 27.38, 27.36, 22.6, 14.1; HRMS Calcd for M+H $C_{16}H_{27}NO_4$: 298.2018. Found: 298.2020.

N-(α-Hexyl-b-ketobutanoyl)-(S)-homoserine: After ester hydrolysis the reaction was carried out with 2-hexyl-3-oxobutanoic acid (0.83 mmol) and (S)-homoserine lactone hydrobromide (0.65 mmol). Purification was carried out by radial silica gel column chromatography (EtOAc:hexane, 1:1, then $EtOAc:CH_2Cl_2$, 1:3) to afford the product as a white solid (147 mg, 84%). $^1$H NMR (400 MHz, $CDCl_3$) d 6.87 (bd, J=21.3 Hz, 1H), 4.58–4.43, (m, 2H), 4.30–4.22 (m, 1H), 3.40 (q, J=8.0 Hz, 1H), 2.80–2.70 (m, 1H), 2.25 (d, J=2.4 Hz, 3H), 2.23–2.12 (m, 1H), 1.91–1.78 (m, 2H), 1.35–1.20 (m, 6H), 0.92–0.82 (m, 3H), 0.85 (t, J=6.8 Hz, 3H); $^{13}$C NMR (100 MHz, $CDCl_3$) d 209.8, 174.7, 169.7, 169.6, 66.0, 65.9, 65.32, 65.30, 65.2, 60.0, 49.3, 49.2, 43.2, 42.9, 31.35, 31.33, 31.27, 31.24, 30.0, 29.6, 29.5, 23.1, 22.5, 14.0, 13.9.

Figure 27:
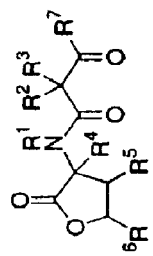
FIG. 27 provides the generic structure for the AHL analogs, as well as the various substitutions for the analogs.

The generic structure of the AHL molecule and the substitutions made to the structure are provided in FIG. 27.

Example 9

Analysis of AHL Analogs

Carrot protoplasts are prepared as described in Example 4A above.

Carrot protoplasts were transfected with the TraA8 (4X)-GUS reporter construct with the 35S-VP16-TraR activator gene and tested for GUS induction by application of wild type AHL and the various AHL analogs described in Example 8.

TABLE 8

Transient assays in carrot protoplasts of AHL analogs

| | Construct 10/28/99 | 1 | 2 | 3 | – inducer | + inducer | 4 | 5 | 6 | fold +/– |
|---|---|---|---|---|---|---|---|---|---|---|
| 1 | min-46GUS | 68.1 | 87.4 | 42.5 | 66.0 | 141.8 | 89.7 | 95.4 | 240.2 | 2.1 |
| 2 | TraA8(4X) + CAT (0/25 μM C8-HSL) | 855.8 | 971.3 | 962.9 | 930.0 | 988.1 | 1101.9 | 791.0 | 1071.3 | 1.1 |
| 3 | +TraR (C8-HSL) (0/25 μM) | 285.3 | 224.6 | 305.8 | 271.9 | 7523.9 | 7034.5 | 8005.8 | 7531.5 | 27.7 |
| 4 | +TraR (C8-HSL) natural (1/2.5 μM) | 1317.9 | 1364.0 | 1107.9 | 1263.2 | 3248.6 | 3249.9 | 3804.6 | 2691.3 | 2.6 |
| 5 | +TraR (C8-HSL) natural (5/12.5 μM) | 2820.7 | 3124.7 | 3110.7 | 3018.7 | 4142.8 | 4386.9 | 4031.2 | 4010.3 | 1.4 |
| 6 | +TraR (C8-HSL) natural (25/75 μM) | 8183.1 | 7890.1 | 6855.5 | 7642.9 | 7975.7 | 8036.8 | 7647.1 | 8243.2 | 1.0 |
| 7 | +TraR 7 (6512572) Methyl (1/2.5 μM) | 74.4 | 242.8 | 223.4 | 180.2 | 316.1 | 374.5 | 292.4 | 281.5 | 1.8 |
| 8 | +TraR 7 (6512572) Methyl (5/12.5 μM) | 916.4 | 1099.1 | 1198.8 | 1071.5 | 2746.0 | 2263.6 | 3016.8 | 2957.5 | 2.6 |
| 9 | +TraR 7 (6512572) Methyl (25/75 μM) | 2276.2 | 2621.4 | 2561.2 | 2486.3 | 3209.7 | 2934.4 | 3011.2 | 3683.6 | 1.3 |
| 10 | +TraR 16 (6512584) Dimethyl (1/2.5 μM) | 100.1 | 139.4 | 95.9 | 111.8 | 316.1 | 230.5 | 194.0 | 523.8 | 2.8 |
| 11 | +TraR 16 (6512584) Dimethyl (5/12.5 μM) | 328.7 | 200.9 | 159.5 | 229.7 | 509.8 | 340.0 | 867.3 | 322.0 | 2.2 |
| 12 | +TraR 16 (6512584) Dimethyl (25/75 μM) | 1154.9 | 1661.5 | 1463.4 | 1426.6 | 4719.8 | 4493.1 | 4685.7 | 4980.7 | 3.3 |
| 13 | +TraR 19 (6512591) Ethyl (1/2.5 μM) | 415.5 | 528.7 | 464.5 | 469.6 | 1310.1 | 1313.0 | 1191.5 | 1425.8 | 2.8 |
| 14 | +TraR 19 (6512591) Ethyl (5/12.5 μM) | 2212.9 | 2543.5 | 1961.9 | 2239.4 | 5377.3 | 5862.9 | 5174.1 | 5094.9 | 2.4 |
| 15 | +TraR 19 (6512591) Ethyl (25/75 μM) | 6750.4 | 7223.4 | 6223.2 | 6732.3 | 7569.1 | 8191.5 | 7437.5 | 7078.3 | 1.1 |
| 16 | +TraR 25 (6630906) Butyl (1/2.5 μM) | 335.2 | 218.9 | 216.8 | 256.9 | 534.7 | 403.7 | 773.0 | 427.3 | 2.1 |
| 17 | +TraR 25 (6630906) Butyl (5/12.5 μM) | 269.9 | 316.3 | 341.6 | 309.3 | 284.7 | 276.2 | 267.4 | 310.4 | 0.9 |
| 18 | +TraR 25 (6630906) Butyl (25/75 μM) | 233.7 | 249.4 | 189.6 | 224.2 | 252.9 | 254.1 | 267.1 | 237.7 | 1.1 |
| 19 | +TraR 26 (6630903) C4-n-hexyl (1/2.5 μM) | 191.4 | 210.8 | 151.9 | 184.7 | 214.0 | 210.1 | 242.3 | 189.7 | 1.2 |
| 20 | +TraR 26 (6630903) C4-n-hexyl (5/12.5 μM) | 382.0 | 407.6 | 373.1 | 387.6 | 1812.5 | 2145.8 | 1764.6 | 1527.0 | 4.7 |

TABLE 8-continued

Transient assays in carrot protoplasts of AHL analogs

| | Construct 10/28/99 | 1 | 2 | 3 | − inducer | + inducer | 4 | 5 | 6 | fold +/− |
|---|---|---|---|---|---|---|---|---|---|---|
| 21 | +TraR 26 (6630903) C4-n-hexyl (25/75 μM) | 1658.7 | 1300.7 | 1586.6 | 1515.3 | 2879.9 | 2585.3 | 3238.5 | 2815.8 | 1.9 |
| 22 | +TraR 22 (6512594) racemic (1/2.5 μM) | 828.3 | 734.9 | 700.5 | 754.6 | 1512.2 | 1465.7 | 1755.7 | 1315.3 | 2.0 |
| 23 | +TraR 22 (6512594) racemic (5/12.5 μM) | 4175.5 | 4210.8 | 3804.9 | 4063.7 | 7819.7 | 8203.4 | 7911.2 | 7344.4 | 1.9 |
| 24 | +TraR 22 (6512594) racemic (25/75 μM) | 10318.1 | 10253.1 | 9537.9 | 10036.4 | 10121.4 | 10679.0 | 10583.6 | 9101.7 | 1.0 |

TABLE 9

Transient assays in carrot protoplasts of AHL analogs

Figure 28:
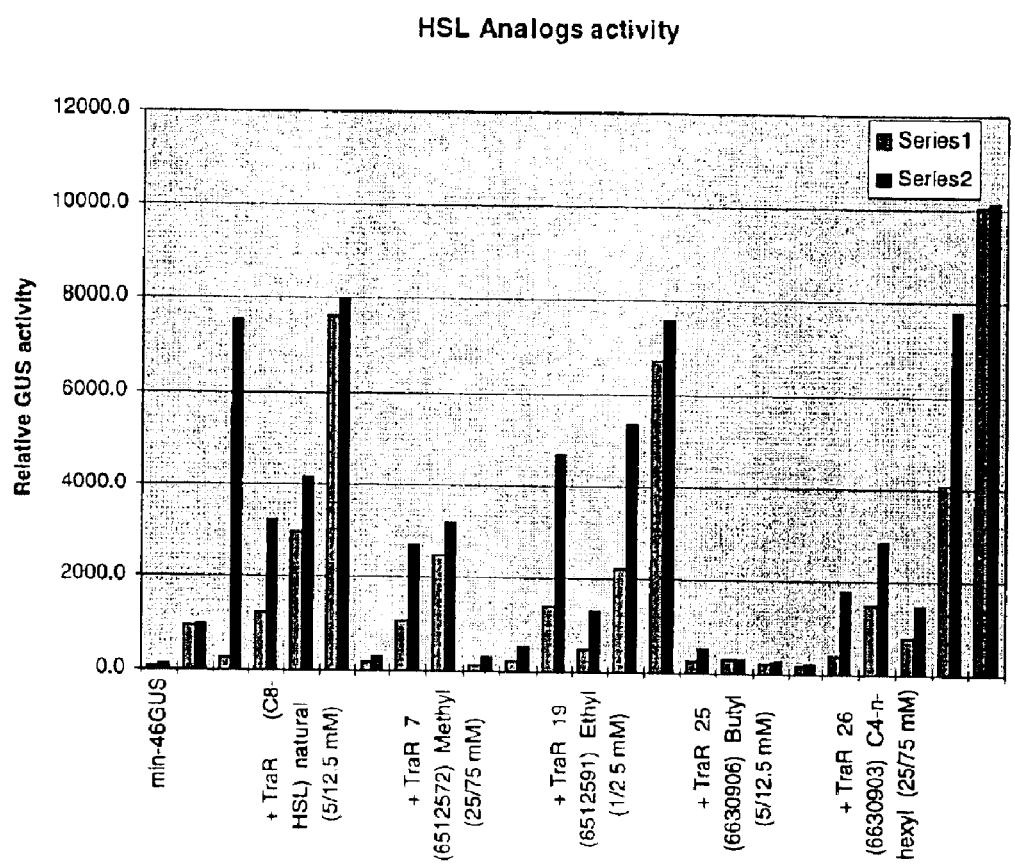
FIG. 28 provides the β-galactosidase activity in induced and non-induced carrot protoplasts containing the TraA8 (4X)-GUS reporter and the 35S-VP16-TraR activator gene constructs. Induction of β-galactosidase activity was performed using the AHL analogs.
Figure 29:
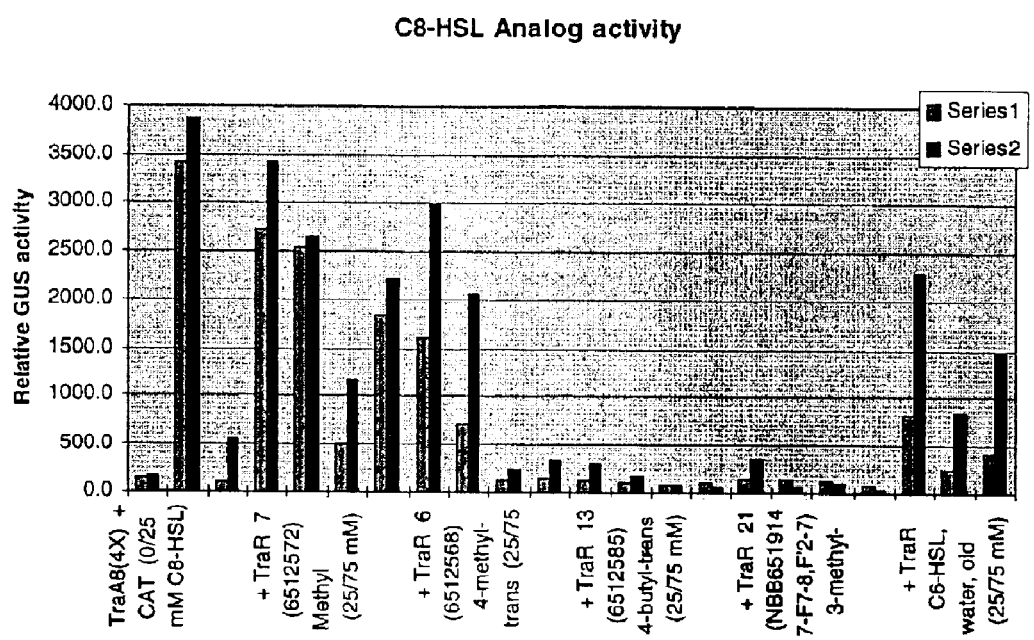
FIG. 29 provides a graphic representation of the data presented in Table 9.

| | Construct 10/19/99 | C (μg/μl) | 60/C | 30/C |
|---|---|---|---|---|
| 1 | min-46GUS (0/25 μM C8-HSL) | 1.40 | 42.9 | 21.4 |
| 2 | TraA8(4X) + CAT (0/25 μM C8-HSL) | 1.46 | 41.1 | 20.5 |
| 3 | +TraR (C8-HSL) (S) (25/75 μM) | 3.22 | 18.6 | 9.3 |
| 4 | +TraR 24 (6512598) (R) (25/75 μM) | 3.22 | 18.6 | 9.3 |
| 5 | +TraR 22 (6512594) racemic (25/75 μM) | 3.22 | 18.6 | 9.3 |
| 6 | +TraR 7 (6512572) Methyl (25/75 μM) | 3.22 | 18.6 | 9.3 |
| 7 | +TraR 16 (6512584) Dimethyl (25/75 μM) | 3.22 | 18.6 | 9.3 |
| 8 | +TraR 19 (6512591) Ethyl (25/75 μM) | 3.22 | 18.6 | 9.3 |
| 9 | +TraR 5 (6512565) 4-methyl-cis (25/75 μM) | 3.22 | 18.6 | 9.3 |
| 10 | +TraR 6 (6512568) 4-methyl-trans (25/75 μM) | 3.22 | 18.6 | 9.3 |
| 11 | +TraR 17 (NBP6519137-F3,F'1-6) 4-ethyl-cis (25/75 μM) | 3.22 | 18.6 | 9.3 |
| 12 | +TraR 18 (NBP6519138-F4) 4-ethyl-trans (25/75 μM) | 3.22 | 18.6 | 9.3 |
| 13 | +TraR 10 (6512586) 4-butyl-cis (25/75 μM) | 3.22 | 18.6 | 9.3 |
| 14 | +TraR 13 (6512585) 4-butyl-trans (25/75 μM) | 3.22 | 18.6 | 9.3 |
| 15 | +TraR 14 (6512586) 4-phenyl-cis (25/75 μM) | 3.22 | 18.6 | 9.3 |
| 16 | +TraR 15 (6512585) 4-phenyl-trans (25/75 μM) | 3.22 | 18.6 | 9.3 |
| 17 | +TraR 20 (NBP6519146-F3,F'3-7) 3-methyl-cis (25/75 μM) | 3.22 | 18.6 | 9.3 |
| 18 | +TraR 21 (NBB6519147-F7-8, F'2-7) 3-methyl-trans (25/75 μM) | 3.22 | 18.6 | 9.3 |
| 19 | +TraR 9 (6512565) 2-methyl (25/75 μM) | 3.22 | 18.6 | 9.3 |
| 20 | +TraR 23 (6512568) N-methyl (25/75 μM) | 3.22 | 18.6 | 9.3 |
| 21 | +TraR (solR C8-HSL) (25/75 μM) | 3.22 | 18.6 | 9.3 |
| 22 | +TraR C6-HSL, water, old (25/75 μM) | 3.22 | 18.6 | 9.3 |
| 23 | +TraR C6-HSL, DMSO. new (25/75 μM) | 3.22 | 18.6 | 9.3 |

β-galactosidase activity in induced and non-induced carrot protoplasts containing the TraA8(4X)-GUS reporter and the 35S-VP16-TraR activator gene constructs induced using various AHL analogs shown in Tables 8 and 9 are provided in graphic form in FIGS. 28 and 29.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claim.

What is claimed is:

1. At least one isolated polynucleotide selected from the group consisting of: a promoter that is functional in a eukaryotic cell, comprising an N-acylhomoserine lactone (AHL)-response element; a promoter that is functional in a eukaryotic cell operably linked to a sequence encoding an AHL synthase; and a promoter that is functional in a eukaryotic cell operably linked to a sequence encoding an AHL receptor.

2. The polynucleotide of claim 1 comprising a promoter that is functional in a eukaryotic cell, comprising an AHL-response element.

3. The polynucleotide of claim 1 comprising a promoter that is functional in a eukaryotic cell operably linked to a sequence encoding an AHL synthase.

4. The polynucleotide of claim 3 comprising a promoter that is functional in a eukaryotic cell, comprising an AHL-response element operably linked to the sequence encoding an AHL synthase.

5. The polynucleotide of claim 1 comprising a promoter that is functional in a eukaryotic cell operably linked to a sequence encoding an AHL receptor.

6. The polynucleotide of claim 1 comprising:
a first sequence comprising a first promoter that is functional in a eukaryotic cell, comprising an AHL-response element, and
a second sequence comprising a second promoter that is functional in the eukaryotic cell operably linked to a sequence encoding an AHL receptor, wherein the AHL receptor binds to the AHL-response element and modulates transcription of the first promoter.

7. The polynucleotide of claim 1 comprising:
a first sequence comprising a first promoter that is functional in a eukaryotic cell, comprising an AHL-response element,
a second sequence comprising a second promoter that is functional in a eukaryotic cell, comprising an AHL-response element operably linked to a sequence encoding an AHL synthase that, when expressed in the eukaryotic cell, synthesizes an AHL, and a third sequence comprising a third promoter that is functional in the eukaryotic cell operably linked to a sequence encoding an AHL receptor, wherein binding of the AHL by the AHL receptor causes the AHL receptor to bind to the AHL-response element and modulate transcription of the first promoter.

8. An organism comprising the polynucleotide of claim 1 selected from the group consisting of a yeast, and a plant.

9. A eukaryotic cell comprising a first sequence comprising a first promoter that is functional in the eukaryotic cell, comprising an AHL-response element operably linked to a gene of interest; and a second sequence comprising a second promoter that is functional in the eukaryotic cell operably linked to a sequence encoding an AHL receptor, wherein binding of an AHL by the AHL receptor causes the AHL receptor to bind to the AHL-response element and modulate transcription of the first promoter.

10. The eukaryotic cell of claim 9 wherein at least one of the first or second promoters is a non-constitutive promoter.

11. The eukaryotic cell of claim 9 wherein the gene of interest is a selectable or screenable marker.

12. A eukaryotic cell comprising a nucleus;

an organelle;

a first sequence comprising a promoter that is functional in the organelle, comprising an AHL-response element operably linked to a gene of interest; and a second sequence comprising a second promoter that is functional in the nucleus operably linked to a sequence that encodes a polypeptide comprising (i) an organelle-transport peptide and (ii) an AHL receptor, wherein the AHL receptor binds to the AHL-response element and modulates transcription of the first promoter upon binding of an AHL.

13. The eukaryotic cell of claim 12 wherein the organelle is a plastid and the organelle-transport peptide is a plastid-transport peptide.

14. The eukaryotic cell of claim 13 wherein the plastid is a chloroplast and the plastid-transport peptide is a chloroplast-transport peptide.

15. A eukaryotic cell comprising an organelle, the organelle comprising:

a first sequence comprising a promoter that is functional in the organelle, comprising an AHL-response element operably linked to a gene of interest; and a second sequence comprising a promoter that is functional in the organelle operably linked to a sequence that encodes a polypeptide comprising an AHL receptor, wherein the AHL receptor binds to the AHL-response element and modulates transcription of the first promoter upon binding of an AHL.

16. The eukaryotic cell of claim 15 wherein the organelle is a plastid.

17. The eukaryotic cell of claim 16 wherein the plastid is a chloroplast.

* * * * *